United States Patent
Bauer et al.

(10) Patent No.: US 10,253,041 B2
(45) Date of Patent: Apr. 9, 2019

(54) 7-PHENYLETHYLAMINO-4H-PYRIMIDO [4,5-D][1,3]OXAZIN-2-ONE COMPOUNDS AND THEIR USE AS MUTANT IDH1 INHIBITORS

(71) Applicant: Eli Lilly and Company, Indianapolis, IN (US)

(72) Inventors: Renato A. Bauer, Indianapolis, IN (US); Serge Louis Boulet, Fishers, IN (US); Timothy Paul Burkholder, Carmel, IN (US); Santiago Carballares Martin, Madrid (ES); James Ronald Gillig, Indianapolis, IN (US); Raymond Gilmour, Indianapolis, IN (US); Wenceslao Lumeras, Madrid (ES); Zhipei Wu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/570,759

(22) PCT Filed: Jul. 21, 2016

(86) PCT No.: PCT/US2016/043264
§ 371 (c)(1),
(2) Date: Oct. 31, 2017

(87) PCT Pub. No.: WO2017/019429
PCT Pub. Date: Feb. 2, 2017

(65) Prior Publication Data
US 2018/0118759 A1    May 3, 2018

(30) Foreign Application Priority Data

Jul. 27, 2015   (EP) .................... 15382386
Dec. 4, 2015    (EP) .................... 15382606

(51) Int. Cl.
| | |
|---|---|
| *A61K 31/519* | (2006.01) |
| *A61K 31/5365* | (2006.01) |
| *C07D 498/04* | (2006.01) |
| *C07D 519/00* | (2006.01) |
| *A61P 35/02* | (2006.01) |
| *A61P 35/00* | (2006.01) |

(52) U.S. Cl.
CPC ............ *C07D 498/04* (2013.01); *A61P 35/00* (2018.01); *A61P 35/02* (2018.01); *C07D 519/00* (2013.01)

(58) Field of Classification Search
CPC . A61K 31/519; A61K 31/5365; C07D 498/04
USPC .......................................... 514/230.5; 544/91
See application file for complete search history.

(56) References Cited

FOREIGN PATENT DOCUMENTS

| WO | 2013/046136 A1 | 4/2013 |
|---|---|---|
| WO | 2014/141104 A1 | 9/2014 |
| WO | 2014/141153 A1 | 9/2014 |
| WO | 2014/147586 A1 | 9/2014 |

OTHER PUBLICATIONS

Balss et al., "Analysis of the IDH1 codon 132 mutation in brain tumors", Acta Neuropathol, 116(2008) pp. 597-602.
Balss et al., "Enzymatic assay for quantitative analysis of (D)-2-hydroxyglutarate", Acta Neuropathol, 124(2012) pp. 883-891.
Cairns et al., "Oncogenic Isocitrate Dehydrogenase Mutations: Mechanisms, Models, and Clinical Opportunities", Jun. 24, 2013.
Dang et al., "Cancer-associated IDH1 mutations produce 2-hydroxyglutarate", Nature, 462(2009) pp. 739-744.
Dang, et al, Nature Supplemental Info S1, 2009.
Dang et al., "IDH mutations in glioma and acute myeloid leukemia", Trends in Molecular Medicine 16(9)(2010) pp. 387-397.
Reitman et al., "Isocitrate Dehydrogenase 1 and 2 Mutations in cancer: Alterations at a Crossroads of Cellular Metabolism", 102(13)(2010).
Shibata et al., "Mutant IDH1 Confers an in Vivo Growth in a Melanoma Cell Line with BRAF Mutation", The American Journal of Pathology, 178(3)(2011).
Ward et al., "Identification of additional IDH mutations associated with oncometabolite R(-)-2-hydroxyglutarate production", (2012) pp. 2491-2498.
Ward et al., Supplementary Table 2 2011.
Carmi, et al., "Clinical perspectives for irreversible tyrosine kinase inhibitors in cancer" Biochemical Pharmacology, 84(2012), pp. 1388-1399.

*Primary Examiner* — Brenda L Coleman
(74) *Attorney, Agent, or Firm* — Grant E Reed

(57) ABSTRACT

Phenylethylamino-4H-pyrimido[4,5-d][1,3]oxazin-2-one compounds of Formula I, formulations containing those compounds, and their use as mutant isocitrate dehydrogenase 1 enzyme inhibitors.

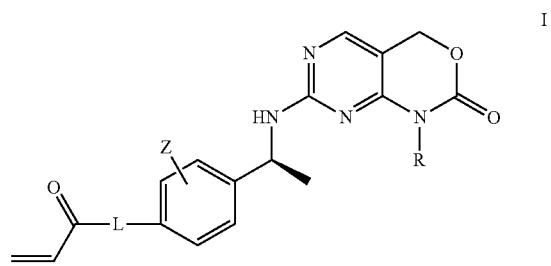

10 Claims, No Drawings

7-PHENYLETHYLAMINO-4H-PYRIMIDO[4,5-D][1,3]OXAZIN-2-ONE COMPOUNDS AND THEIR USE AS MUTANT IDH1 INHIBITORS

The isocitrate dehydrogenase (IDH) protein is an important enzyme in the citric acid (tricarboxylic acid or Krebs) cycle. The citric acid cycle is centrally important to many biochemical pathways and is one of the earliest established components of cellular metabolism.

Isocitrate dehydrogenases catalyze the oxidative decarboxylation of isocitrate to α-ketoglutarate (2-oxoglutarate). These enzymes belong to two distinct subclasses, one of which utilizes nicotinamide adenine dinucleotide (NAD(+)) as the electron acceptor and the other nicotinamide adenine dinucleotide phosphate (NADP(+)). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a dimer. The protein encoded by the IDH1 gene is the NADP(+)-dependent isocitrate dehydrogenase found in the cytoplasm and peroxisomes. The cytoplasmic enzyme serves a significant role in cytoplasmic NADPH production. IDH1 is expressed in a wide range of species and in organisms that lack a complete citric acid cycle.

Recently, mutations in IDH1, and the related isoform IDH2, have been found in several types of cancers. Mutations were found to occur at specific amino acids along the protein sequence and to be heterozygously expressed, consistent with a gain of function. These mutations occur at functionally conserved residues and biochemical studies of the mutant forms of IDH1 demonstrated a loss of normal function of IDH1, the reversible conversion of isocitrate to α-ketoglutarate. The result of these mutations is to allow a new (or neomorphic) conversion of α-ketoglutarate (αKG) to 2-hydroxyglutarate (2HG). As a result, cancers cells that harbor mutant forms of IDH1 or IDH2 form substantially higher concentrations of 2HG. High levels of 2HG result in a block in cell differentiation that can be reversed by mutant IDH1 or IDH2 inhibition.

There is a need for compounds that selectively inhibit mutant IDH1 enzyme over wild type IDH2 for the treatment of various cancers. There is a further need for compounds that selectively inhibit mutant IDH1 enzyme demonstrating neomorphic activity over wild type IDH1 for the treatment of various cancers.

One aspect of the invention is to provide mutant IDH1 enzyme inhibitor compounds of the Formula:

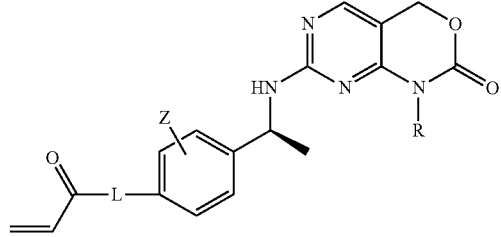

I wherein
L is a linker selected from the group consisting of
—N-azetidine-3-$CH_2$—O—, —N-azetidine-3-O—($CH_2$)—, —N-2,6-diazaspiro[3.3]heptane-6-($CH_2$)—, —N-piperazine-4-($CH_2$)—, —N-piperazine-, —N-azetidine-3-($CH_2CH_2$)—, -7-N-(2,7-diazaspiro[3.5]nonane)-2-($CH_2$)—, —N-azetidine-3-(NMe)$CH_2$—, —N-piperidine-4-(NMe)$CH_2$— and —N-2,5-dihydropyrrol-3-($CH_2$)—O—;

Z is selected from the group consisting of H and F;
R is selected from the group consisting of $C_1$-$C_4$ alkyl, —CH($CH_3$)$CH_2$—OH, —$CH_2CH_2$F, and —$CH_2CHF_2$; or a pharmaceutically acceptable salt thereof.

A further aspect of the present invention provides a compound of Formula I wherein: L is a linker selected from the group consisting of —N-piperazine-4-($CH_2$)—, —N-piperazine-, —N-azetidine-3-(NMe)$CH_2$—, —N-azetidine-3-$CH_2$—O—, —N-azetidine-3-O—($CH_2$)—, —N-azetidine-3-($CH_2CH_2$)—, and —N-piperidine-4-(NMe)$CH_2$—;
Z is H;
R is $C_1$-$C_4$ alkyl; or a pharmaceutically acceptable salt thereof.

Another aspect of the present invention provides a compound of Formula I wherein: L is a linker selected from the group consisting of —N-piperazine-4-($CH_2$)—, —N-piperazine-, —N-azetidine-3-O—($CH_2$)—, —N-azetidine-3-($CH_2CH_2$)—, —N-azetidine-3-(NMe)$CH_2$—, and —N-piperidine-4-(NMe)$CH_2$—;
Z is H;
R is selected from —$CH_2CH_3$, —CH($CH_3$)$_2$; or a pharmaceutically acceptable salt thereof.

A further aspect of the invention is a compound 1-isopropyl-7-[[(1S)-1-[4-[(4-prop-2-enoylpiperazin-1-yl)methyl]phenyl]ethyl]amino]-4H-pyrimido[4,5-d][1,3]oxazin-2-one, or a pharmaceutically acceptable salt thereof.

Another aspect of the invention is a compound 1-ethyl-7-[[(1S)-1-[4-[(4-prop-2-enoylpiperazin-1-yl)methyl]phenyl]ethyl]amino]-4H-pyrimido[4,5-d][1,3]oxazin-2-one, or a pharmaceutically acceptable salt thereof.

A further aspect of the invention is a compound selected from:
1-isopropyl-7-[[(1S)-1-[4-(4-prop-2-enoylpiperazin-1-yl)phenyl]ethyl]amino]-4H-pyrimido[4,5-d][1,3]oxazin-2-one, or a pharmaceutically acceptable salt thereof;
1-ethyl-7-[[(1S)-1-[4-(4-prop-2-enoylpiperazin-1-yl)phenyl]ethyl]amino]-4H-pyrimido[4,5-d][1,3]oxazin-2-one, or a pharmaceutically acceptable salt thereof;
1-ethyl-7-[[(1S)-1-[4-[(1-prop-2-enoylazetidin-3-yl)oxymethyl]phenyl]ethyl]amino]-4H-pyrimido[4,5-d][1,3]oxazin-2-one, or a pharmaceutically acceptable salt thereof;
1-ethyl-7-[[(1S)-1-[4-[2-(1-prop-2-enoylazetidin-3-yl)ethyl]phenyl]ethyl]amino]-4H-pyrimido[4,5-d][1,3]oxazin-2-one, or a pharmaceutically acceptable salt thereof;
1-isopropyl-7-[[(1S)-1-[4-[(1-prop-2-enoylazetidin-3-yl)methoxy]-phenyl]ethyl]amino]-4H-pyrimido[4,5-d][1,3]oxazin-2-one, or a pharmaceutically acceptable salt thereof;
1-ethyl-7-[[(1S)-1-[4-[[methyl-(1-prop-2-enoylazetidin-3-yl)amino]methyl]-phenyl]ethyl]amino]-4H-pyrimido[4,5-d][1,3]oxazin-2-one, or a pharmaceutically acceptable salt thereof.

Another aspect of the present invention provides a pharmaceutical composition comprising a mutant IDH1 inhibitor compound of Formula I, or a pharmaceutically acceptable salt thereof, and a pharmaceutically acceptable carrier.

A further aspect of the present invention provides a method of treating a cancer expressing mutant IDH1 which is glioma, glioblastoma, glioblastoma multiforme, astrocytomas, oligodendrogliomas, paraganglioma, fibrosarcoma, angioimmunoblastic T-cell lymphoma (AITL), myelodysplastic syndrome (MDS), B cell acute lymphoblastic leukemia (B-ALL), thyroid cancer, colorectal cancer, acute myeloid leukemia (AML), melanoma, prostate cancer, chondrosarcoma or cholangiocarcinoma in a patient comprising administering to a patient in need thereof a therapeutically effective amount of a compound of Formula I, or a pharmaceutically acceptable salt thereof.

Another aspect of the present invention provides a method of treating a cancer expressing mutant IDH1 which is fibrosarcoma, acute myeloid leukemia, glioma, or glioblastoma in a patient comprising administering to a patient in need thereof a therapeutically effective amount of a compound of Formula I, or a pharmaceutically acceptable salt thereof.

A further aspect of the present invention provides a compound of Formula I, or a pharmaceutically acceptable salt thereof, for use in therapy.

Another aspect of the present invention provides a compound of Formula I, or a pharmaceutically acceptable salt thereof; for use in the treatment of a cancer expressing mutant IDH1 which is glioma, glioblastoma, glioblastoma multiforme, astrocytomas, oligodendrogliomas, paraganglioma, fibrosarcoma, angioimmunoblastic T-cell lymphoma (AITL), myelodysplastic syndrome (MDS), B cell acute lymphoblastic leukemia (B-ALL), thyroid cancer, colorectal cancer, acute myeloid leukemia (AML), melanoma, prostate cancer, chondrosarcoma or cholangiocarcinoma.

A further aspect of the present invention provides a compound of Formula I, or a pharmaceutically acceptable salt thereof; for use in the treatment of a cancer expressing mutant IDH which is fibrosarcoma, acute myeloid leukemia, glioma, or glioblastoma.

Another aspect of the present invention provides use of a compound of Formula I, or a pharmaceutically acceptable salt thereof, for the manufacture of a medicament for the treatment of a cancer expressing mutant IDH1 which is glioma, glioblastoma, glioblastoma multiforme, astrocytomas, oligodendrogliomas, paraganglioma, fibrosarcoma, angioimmunoblastic T-cell lymphoma (AITL), myelodysplastic syndrome (MDS), B cell acute lymphoblastic leukemia (B-ALL), thyroid cancer, colorectal cancer, acute myeloid leukemia (AML), melanoma, prostate cancer, chondrosarcoma or cholangiocarcinoma.

A further aspect of the present invention provides use of a compound of Formula I, or a pharmaceutically acceptable salt thereof, for the manufacture of a medicament for the treatment of a cancer expressing mutant IDH1 which is fibrosarcoma, acute myeloid leukemia, glioma, or glioblastoma.

The term "patient" means mammal and "mammal" includes, but is not limited to, a human.

"Therapeutically effective amount" or "effective amount" means the dosage of the compound of Formula I, or pharmaceutically acceptable salt thereof, or pharmaceutical composition containing the compound, or pharmaceutically acceptable salt thereof, necessary to inhibit mutant IDH1 in a cancer patient, leading to the release of the block in differentiation with resulting inhibition of tumor cell growth and eliminate or slow or arrest the progression of the cancer in a patient. Anticipated dosages of a compound of Formula I, or a pharmaceutically acceptable salt thereof are in the range of 20 mg/patient/day to 2000 mg/patient/day. Preferred dosages are anticipated to be in the range of 30 mg/patient/day to 1800 mg/patient/day. Most preferred dosages are anticipated to be in the range of 40 mg/patient/day to 1600 mg/patient/day. The exact dosage required to treat a patient and the length of treatment time will be determined by a physician in view of the stage and severity of the disease as well as the specific needs and response of the individual patient. Although expressed as dosage on a per day basis, the dosing administration may be adjusted to provide a more optimal therapeutic benefit to a patient and to manage or ameliorate any drug related toxicities. In addition to daily dosing, twice a day (B.I.D.) dosing, three times a day (T.I.D.) dosing, dosing every other day (Q2D); every other day over a five day period followed by two days without dosing (T.I.W.); or every third day (Q3D) may be appropriate.

The terms "treatment," "treat," and "treating," are meant to include the full spectrum of intervention for the cancer from which the patient is suffering, such as administration of the active compound to alleviate, slow, or reverse one or more of the symptoms and to delay progression of the cancer even if the cancer is not actually eliminated.

The phrase "$C_1$-$C_4$ alkyl" includes methyl, ethyl, n-propyl, isopropyl, n-butyl, isobutyl, sec-butyl, and t-butyl.

A compound of Formula I, or a pharmaceutically acceptable salt thereof, is preferably formulated as a pharmaceutical composition using a pharmaceutically acceptable carrier and administered by a variety of routes. Preferably, such compositions are for oral administration. Such pharmaceutical compositions and processes for preparing them are well known in the art. See, for example, REMINGTON: THE SCIENCE AND PRACTICE OF PHARMACY (A. Gennaro, et al., eds., 19$^{th}$ ed., Mack Publishing Co., 1995). In a particular embodiment, the pharmaceutical composition comprises 1-ethyl-7-[[(1S)-1-[4-[(4-prop-2-enoylpiperazin-1-yl)methyl]phenyl]ethyl]amino]-4H-pyrimido[4,5-d][1,3]oxazin-2-one or a pharmaceutically acceptable salt thereof, together with a pharmaceutically acceptable carrier and optionally other therapeutic ingredients particularly for treatment of cancer generally or a specific cancer type.

A compound of Formula I, or a pharmaceutically acceptable salt, may be administered either simultaneously with, or before, or after, one or more other therapeutic agents. The compound of formula I or a pharmaceutically acceptable salt, when administered with one or more other therapeutic agents, may be administered separately, by the same or different route of administration, or together in the same pharmaceutical composition as the other therapeutic agent(s). Where one or more additional therapeutic agents are administered, the administration of each therapeutic agent may be simultaneous, separate, or sequential.

A compound of Formula I is capable of reaction with a number of inorganic and organic acids to form pharmaceutically acceptable acid addition salt. Such pharmaceutically acceptable salts and common methodology for preparing them are well known in the art. See, for example, P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts, "*Journal of Pharmaceutical Sciences*, Vol. 66, No. 1, January 1977.

A compound of Formula I, or a pharmaceutically acceptable salt thereof, may be prepared by a variety of procedures known in the art, as well as those described below. The specific synthetic steps may be combined in a different order to prepare a compound of Formula I, or a pharmaceutically acceptable salt thereof.

Compounds of Formula I are named according to IUPAC, and may also be named according to CAS, and other names may be used to unambiguously identify a compound of Formula I, or a pharmaceutically acceptable salt thereof.

It will be understood a compound of Formula I may be depicted as a single stereoisomer. There is one chiral center at the stereogenic benzylic carbon position giving rise to two diastereomers and possibly more depending on substituents. As used herein, references to a single stereoisomer are meant to also include stereoisomeric mixtures including the named or depicted compound of Formula I. Herein, the Cahn-Ingold-Prelog designations of (R)- and (S)- may be used to refer to specific stereoisomers. Specific stereoisomers can be prepared by stereospecific synthesis using enantiomerically pure or enriched starting materials. The specific stereoisomers of either starting materials, intermediates, or racemic mixtures including compounds of Formula I can be resolved by techniques well known in the art, such as those found in *Stereochemistry of Organic Compounds*, E. I. Eliel and S. H. Wilen (Wiley 1994) and *Enantiomers, Racemates. and Resolutions*. J., Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts. While diastereomeric mixtures containing a compound of Formula I are contemplated within the present invention, the preferred embodiment is the (S) configuration as shown for Formula I.

The compounds employed as initial starting materials in the synthesis of the compounds of Formula I are well known and, to the extent not commercially available, are readily synthesized using specific references provided, by standard procedures commonly employed by those of ordinary skill in the art or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

Certain stereochemical centers may be left unspecified in the following schemes for the sake of clarity and are not intended to limit the teaching of the schemes in any way. Individual isomers, enantiomers, and diastereomers may be separated or resolved by one of ordinary skill in the art at any convenient point in the synthesis of compounds of the invention, by methods such as selective crystallization techniques or chiral chromatography.

Certain abbreviations are defined as follows: "ACN" refers to acetonitrile; "αKG" refers to Alpha-ketoglutarate or 2-ketoglutarate; "alloc" refers to allyloxycarbonyl; "ATCC" refers to American Type Culture collection; "BCA" refers to bicinchoninic acid; "BOC" refers to tert-butoxy carbonyl; "BSA" refers to Bovine Serum Albumin; "CDI" refers to 1,1'-carbonyldiimidazole; "CPME" refers to cyclopentyl methyl ether; "DCC" refers to 1,3-dicyclohexylcarbodiimide; "DCM" refers to dichloromethane; "DEAD" refers to diethyl azodicarboxylate; "DIAD" refers to diisopropyl azodicarboxylate; "DIC" refers to diisopropylcarbodiimide; "DIPEA" refers to diisopropylethylamine or N-ethyl-N-isopropyl-propan-2-amine; "DMA" refers to dimethylacetamide; "DMAP" refers to dimethylaminopyridine; "DMF" refers to dimethylformamide; "DMSO" refers to dimethyl sulfoxide; "DTT" refers to dithiothreitol; "EDC" refers to EDAC, EDCI, or 1-(3-dimethylaminopropyl)-3-ethylcarbodiimide hydrochloride; "EDTA" refers to ethylenediaminetetraacetic acid; "EGTA" refers to ethylene glycol tetraacetic acid; "EtOAc" refers to ethyl acetate; "EtOH" refers to ethanol or ethyl alcohol; "Ex" refers to example; "HATU" refers to (dimethylamino)-N,N-dimethyl(3H-[1,2,3]triazolo[4,5-b]pyridin-3-yloxy)methaniminium hexafluorophosphate; "HBTU" refers to 2-(1H-benzotriazole-1-yl)-1,1,3,3-tetramethyluronium hexafluorophosphate; "HEK" refers to human embryonic kidney; "2HG" refers to 2-hydroxyglutarate; "d$_5$-3HG" refers to 3-hydroxy-1,5-pentanedioic-2,2,3,4,4-d$_5$ acid; "HILIC" refers to hydrophilic interaction liquid chromatography; "HOAt" refers to 1-hydroxy-7-azobenzotriazole; "HOBt" refers to 1-hydroxylbenzotriazole hydrate; "HPLC" refers to high-performance liquid chromatography; "IC$_{50}$" refers to the concentration of an agent that produces 50% of the maximal inhibitory response possible for that agent; "mCPBA" refers to meta-chloroperbenzoic acid; "Me" refers to methyl or CH$_3$; "MeOH" refers to methanol or methyl alcohol; "MTBE" refers to methyl tert-butyl ether; "NADP$^+$ and NAHPH" refers to the oxidized and reduced forms of nicotinamide adenine dinucleotide phosphate respectively; "NMP" refers to N-methyl-2-pyrrolidone; "PG" refers to protecting group; "Ph" refers to phenyl; "Prep" refers to preparation; "PyBOP" refers to benzotriazol-1-yloxytripyrrolidino-phosphonium hexafluorophosphate; "PyBrop" refers to bromo-tris-pyrrolidino phosphoniumhexafluoro phosphate; "rpm" refers to revolutions per minute; "SCX" refers to strong cation exchange; "S$_N$Ar" refers to nucleophilic aromatic substitution; "TEA" refers to triethylamine; "TFA" refers to trifluoroacetic acid; "THF" refers to tetrahydrofuran; THP refers to tetrahydropyranyl; "Tris" refers to tris(hydroxymethyl)aminomethane and "XRD" refers to X-ray powder diffraction.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art.

Scheme 1

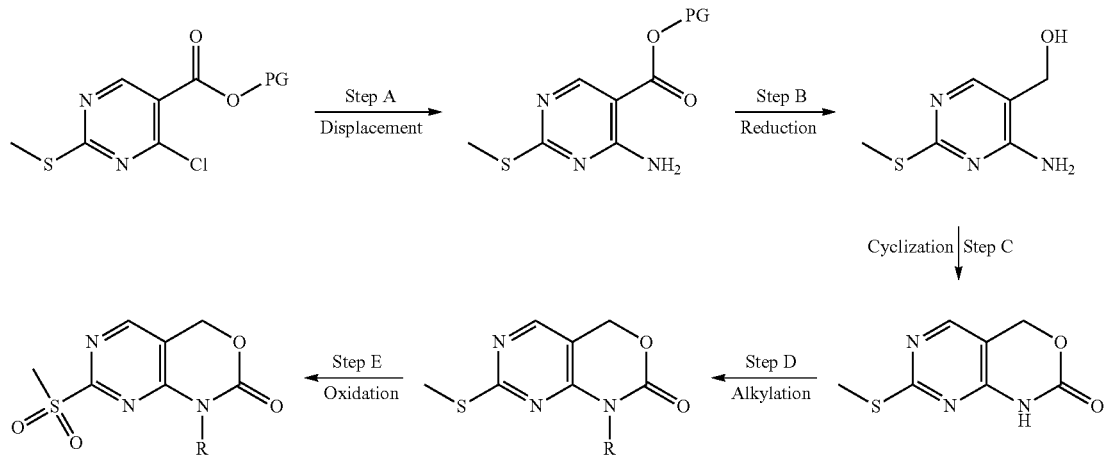

In Scheme 1, a series of reactions leads to a 1-substituted-7-(methylsulfonyl)-1,4-dihydro-2H-pyrimido[4,5-d][1,3]oxazin-2-one, the product of Step E where R is as previously defined or R=CH(CH$_3$)—CH$_2$—O-PG. "PG" is a protecting group developed for the amino group or oxygen group such as for carbamates, amides or esters. For example, in Step A, the chloro of a carboxyl protected-4-chloro-2-(methylthio)pyrimidine-5-carboxylate is converted to the amine using ammonium hydroxide in a solvent such as THF to give the substituted pyrimidine amine product of Step A. In Step B, the ester, such as an ethyl ester, can be reduced with a hydride source, such as lithium aluminum hydride, in a solvent such as THF to the hydroxymethyl under conditions well known in the art to give the hydroxymethyl product of Step B. The 5-hydroxy methyl 4-amine-pyrimidine can be cyclized under standard carbamoylation conditions to the oxazine-2-one using triphosgene and an organic base such as DIPEA or TEA at a temperature of about −30 to −35° C. to give the product of Step C. Alternatively a dihalide carbonyl or a di-pseudohalide carbonyl such as CDI, phosgene, or diphosgene can be used instead of triphosgene to complete the carbamoylation. The amine of the oxazine can be alkylated with the appropriate substituted alkyl halide such as an iodo reagent in a solvent such as NMP and an inorganic base such as K$_2$CO$_3$ at a temperature of about 50-65° C. to give the product of Step D. Alternatively, a Mitsunobu reaction can be accomplished to alkylate the amine of the oxazine using an appropriate alcohol such as MeOH. Mitsunobu reactions are well known in the art and can convert a hydroxyl group into a leaving group that is displaced by a wide variety of nucleophiles such as a carbamate using triphenylphosphine and an azodicarboxylate such as DIAD or DEAD in a solvent such as THF to give the product of Step D. The sulfide can be oxidized to the sulfone under conditions well known in the art such as mCPBA or potassium peroxymonosulfate at a temperature of about 10 to 25° C. in a solvent such as ACN or CH$_2$Cl$_2$ to give the product of Step E. Alternatively, in Step A, an alkoxyalkyl amine substituted product can be prepared from the substituted 4-chloropyrimidine in a 3 step procedure. For example, (2R)-1-(tert-Butyl dimethylsilyl)oxypropan-2-amine and a base such as DIPEA in a solvent such as DMF is heated to about 65° C. followed by quenching with water and extracting with EtOAc to give a crude intermediate siloxyalkylaminopyrimidine. This intermediate is treated with tetra-butylammonium fluoride, concentrated, and then purified with silica gel to give an intermediate hydroxyalkylaminopyrimidine. The intermediate hydroxyl group can be protected with 3,4-dihydro-2H-pyran using p-toluenesulfonic acid and following purification gives the hydroxyl protected product of Step A.

Scheme 2

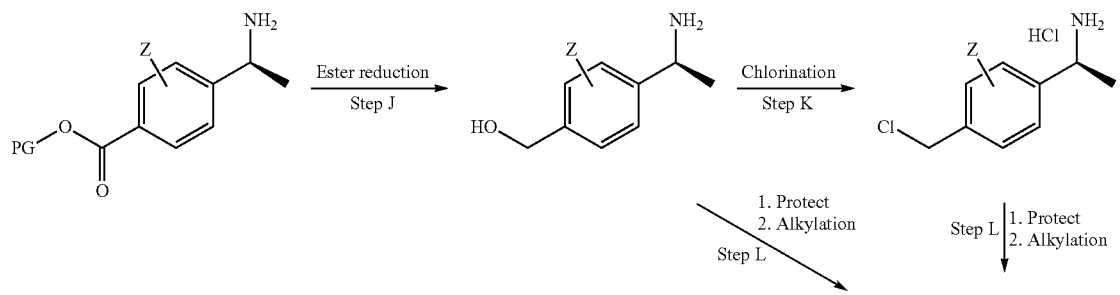

-continued

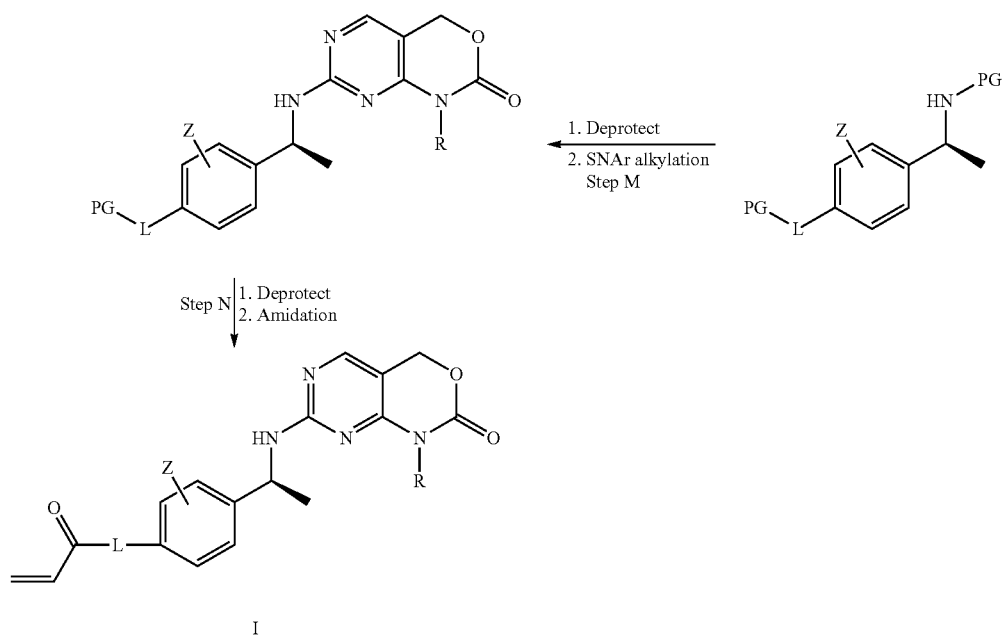

In Scheme 2, Step J, a 4-ethylamine-protected-benzoic acid is reduced using conditions well known in the art such as lithium aluminum hydride in a solvent such as THF to give the 4-ethylamine-benzyl-hydroxy compound. The benzyl-hydroxy product of Step J can be converted to a halide such as a chloride under standard chlorination conditions using a chlorinating agent such as thionyl chloride or POCl$_3$ in a solvent such as CH$_2$Cl$_2$ to give the product of Step K. The 1-phenylethylamine product of Step K or the benzyl-hydroxy product of Step J can be protected in substep 1 of Step L using a protecting group such as a trifluoroacetyl. The chloride of the product of Step L can be displaced with a protected amine of the linker group (L) in a two-step, one pot procedure. It is not always necessary to protect the 1-phenylethylamine but if protection is chosen, it is advantageous to use a different protecting group on the 1-phenylethylamine than the linker amine to selectively deprotect one or the other PG at the desired step. For example, the 1-phenylethylamine can be reacted with trifluoroacetic anhydride using an organic base such as TEA in a solvent such as CH$_2$Cl$_2$ at a temperature of about 0-5° C. to give the protected amine product of substep 1, Step L. Displacement of the chloride can then be accomplished under conditions well known by one skilled in the art. For example, when the linker has an amine, the chloride can be displaced by an appropriate linker amine using an inorganic base such as K$_2$CO$_3$ with heating to about 60° C. in a solvent such as ACN to give the product of substep 2, Step L. Alternatively, an organic base such as DIPEA in a solvent such as DMSO can be used to alkylate the amine to give the product of substep 2, Step L. When the linker is attached through an ether linkage, the alcohol precursor can displace the halide with a base such as sodium hydride in a solvent such as DMF to give the product of substep 2, Step L. In Step M, substep 1, the 1-phenylethylamine can be deprotected if protection is previously effected under standard deprotection conditions using alkaline conditions such as aqueous sodium hydroxide in a solvent such as EtOH to give the free amine product of substep 1, Step M. Alternatively if the protecting group is a carboxybenzyl group, hydrogenolysis conditions can be used to remove the protection group such as using 10% Pd/C in a solvent such as EtOH under a hydrogen atmosphere to give the deprotected product of Step M, substep 1. The 1-phenylethylamine can then be reacted with the product of Scheme 1, Step E in a S$_N$Ar reaction using an organic base such as DIPEA, CsF to accelerate the reaction, a solvent such as DMSO, and a temperature of about 70-80° C. to give the product of Step M, substep 2. In Step N, substep 1, a tert-butoxy protected linker can be deprotected using an acid such as HCl in dioxane and MeOH or TFA in CH$_2$Cl$_2$ whereas an alloc protected linker can be deprotected in the presence of a palladium source such as catalytic tetrakis(triphenylphosphine)palladium(0) in a solvent such as THF using a soft nucleophile such as dimedone to give the deprotected linker of substep 1, Step N. In substep 2, Step N, the linker amine can be amidated with acryloyl chloride at a temperature of about 50 to 75° C. using an organic base such as TEA if the amine is an acid salt in a solvent such as CH$_2$Cl$_2$ to give compounds of Formula I. Alternatively, an amide coupling can be accomplished with acrylic acid and the appropriate amine in a solvent such as DMF with a coupling reagent such as EDC and an additive such as HOBt. One skilled in the art will recognize that there are a number of methods and reagents for amide formation resulting from the reaction of carboxylic acids and amines. For example, the reaction of the appropriate amine and acrylic acid in the presence of a coupling reagent with or without an organic base such as DIPEA or TEA can provide a compound of Formula I. Other coupling reagents include carbodiimides, such as DCC, DIC, or a carbonyldiimidazole such as CDI. Other amide coupling additives, such as HOAt can also be used to enhance the reaction. Additionally, uronium or phosphonium salts of non-nucleophilic anions, such as HBTU, HATU, PyBOP, and PyBrOP could be used in place of the more traditional coupling reagents. An additive such as DMAP may be used to accelerate the desired amidation reaction.

carbonate, CuBr, and hydroxyproline in a solvent such as DMSO to give the product of Step P. For the examples where L involves an alkyne, the Br can be reacted with the appropriate protected alkyne using palladium cross coupling conditions such as in a Sonagashira reaction. An appropriate palladium catalyst such as tetrakis(triphenylphosphine)palladium(0), a copper catalyst such as CuI, and an organic base

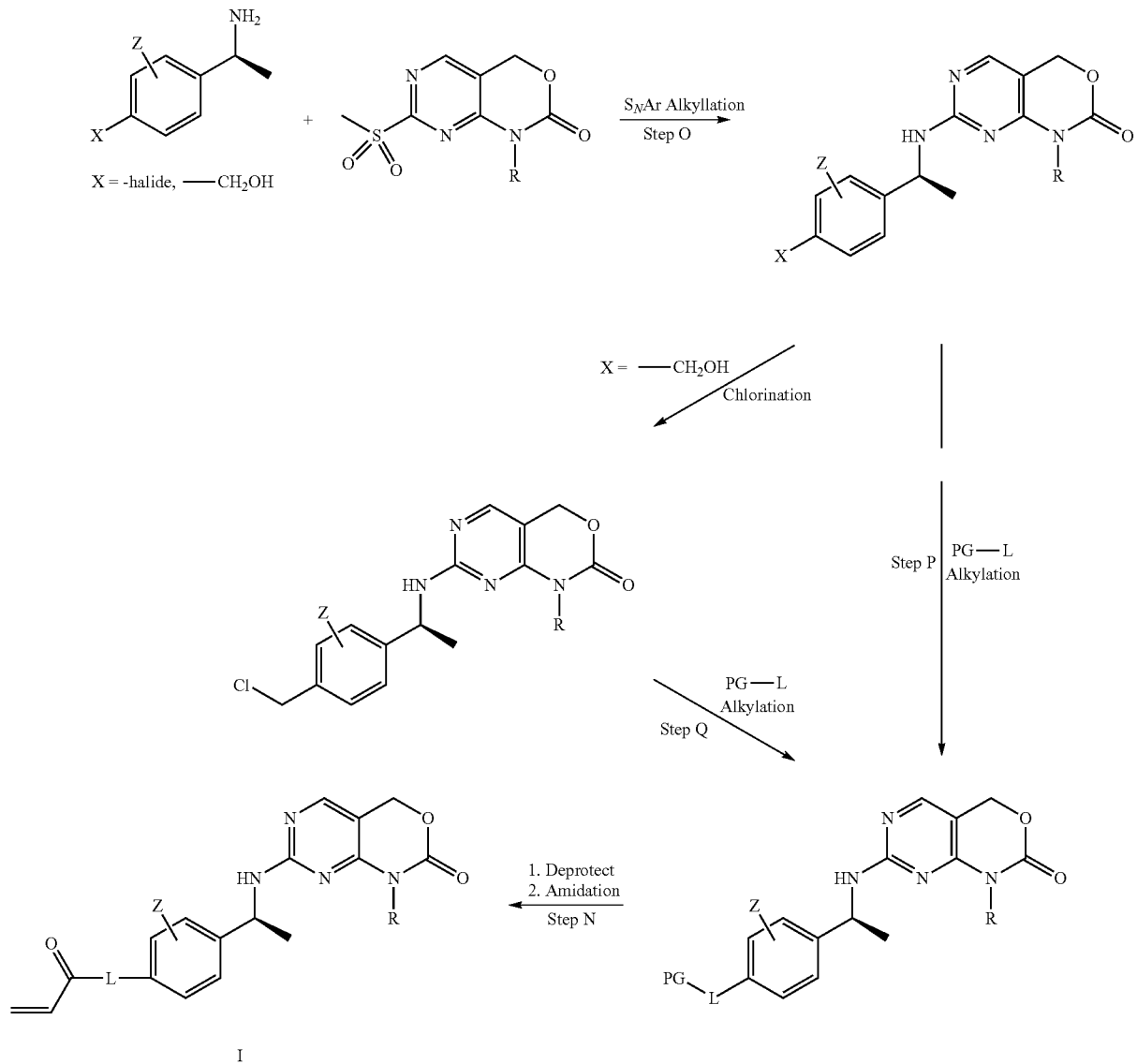

Scheme 3

Alternatively m Scheme 3, a 1-phenylethylamine without the linker in place can be reacted with the product of Step E as described in Scheme 2, Step M to give the product of Step O. The product of Step O can be reacted with the protected linker as described in Scheme 2, Step L, substep 2 using $K_2CO_3$ and sodium iodide in ACN to give the product of Step P. Alternatively, if X=Br, the bromide can be displaced with an amine using an inorganic base such as potassium such as TEA is combined with the appropriate alkyne and aryl bromide in a solvent such as THF to give the product of Step P. When X=—CH$_2$OH, the OH can be converted to the chloride as described in Scheme 2, Step K to give the chlorinated product of Step Q. An alkyne Linker of Step P can be hydrogenated with a catalyst such as 10% Pd/CaCO$_3$ in a solvent such as THF under hydrogen to give the reduced alkyne product. In Step N, the products of Step P or Step Q can then be deprotected as described in Scheme 2, Step N, substep 1 and the linker can be amidated as described in Scheme 2, Step N, substep 2 to give compounds of Formula I.

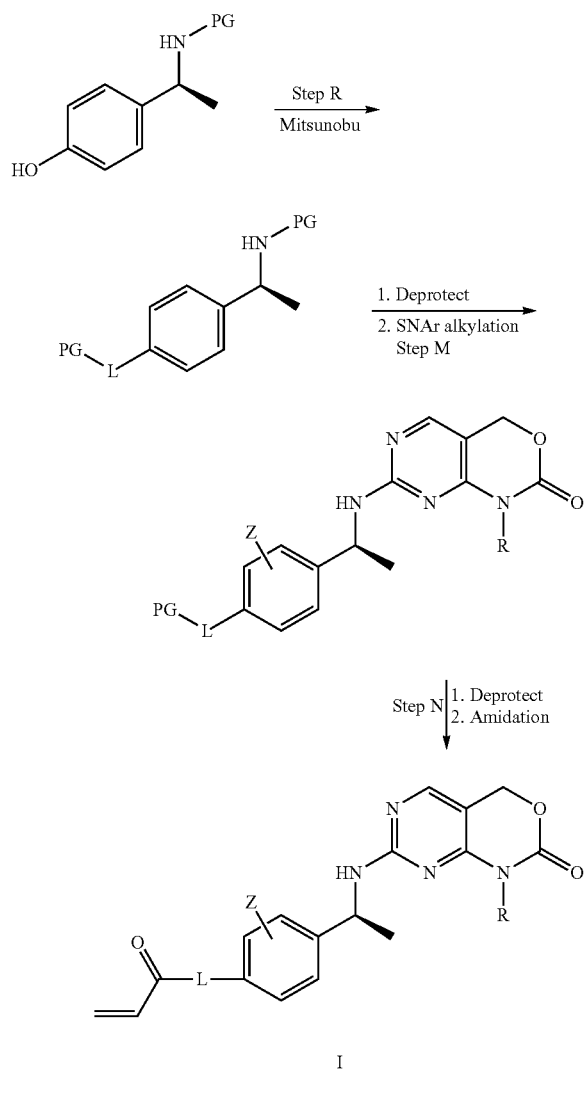

Scheme 4

In Scheme 4, the 1-phenylethylamine can be protected as described in Scheme 2, Step L with a protecting group such as trifluoroacetyl or other protecting groups such as carboxy benzyl. For example when carboxy benzyl is the desired PG, benzyl chloroformate can be added to the 1-(4-hydroxyphenyl)ethylamine with an inorganic base such as $NaHCO_3$ in a mixture of solvents such as THF and water to give the carboxy benzyl protected amine. When the linker L is attached to the aryl ring through an ether linkage, a Mitsunobu reaction can be accomplished on a protected 1-(4-hydroxyphenyl)ethylamine. Mitsunobu reactions are well known in the art and can convert a hydroxyl group into a potent leaving group that is able to be displaced by a wide variety of nucleophiles such as a phenol using triphenylphosphine and an azodicarboxylate such as DIAD or DEAD in a solvent such as THF to give the aryl ether product of Step R. The product of Step R can then be deprotected at the 1-phenylethylamine functionality as described in Scheme 2, Step M, substep 1 followed by the $S_NAr$ alkylation as described in Scheme 2, Step M, substep 2 to give the product of Scheme 4, Step M. Products of Formula I from Step N can then be formed as described in Scheme 2, Step N, substeps 1 and 2.

In an optional step, a pharmaceutically acceptable salt of a compound of Formula I can be formed by reaction of an appropriate free base of Formula I with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 3: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One of ordinary skill in the art will appreciate that a compound of Formula I is readily converted to and may be isolated as a pharmaceutically acceptable salt Preparation 1

Ethyl 4-amino-2-methylsulfanyl-pyrimidine-5-carboxylate

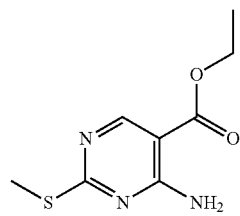

Scheme 1, Step A: Ammonium hydroxide (8.4 L, 17 wt %, 6.86 mol) is added over 1 hour to a solution of ethyl 4-chloro-2-(methylthio)pyrimidine-5-carboxylate (4 Kg, 10.74 mol) in THF (34.4 L) at room temperature. After stirring for 4 hours, water is added and the mixture is extracted with MTBE. The organic phase is washed with brine, dried over $Na_2SO_4$, filtered, and concentrated. The crude product is slurried with petroleum ether (3 L), filtered, and dried under vacuum to provide the title compound as a white solid (3.5 Kg, 89% purity, 95% yield) which is carried on without further purification. MS (m/z): 214 (M+H).

Preparation 2

2-Methylsulfanyl-4-[[(1R)-1-methyl-2-tetrahydropyran-2-yloxy-ethyl]amino]-pyrimidine-5-carboxylate

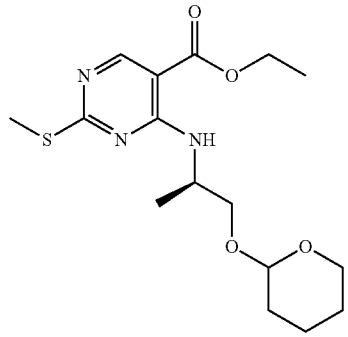 [SMILES: CCOC(=O)c1cnc(SC)nc1N[C@H](C)COC1CCCCO1]

Scheme 1, Step F: DIPEA (9.1 mL, 52 mmol) and (2R)-1-(tert-butyl silyl)oxypropan-2-amine (5.82 g, 30.7 mmol) are added to a solution of ethyl 4-chloro-2-(methylthio)pyrimidine-5-carboxylate (6 g, 25.8 mmol) in DMF (50 mL) at room temperature. After stirring for 10 minutes at room temperature, the mixture is heated to 65° C. for 1.5 hours, cooled to room temperature, treated with water, and is extracted with EtOAc (2×). The organic extracts are washed with aqueous 5% LiCl (3×), dried over $Na_2SO_4$, filtered, and concentrated. The crude material (8.64 g, 22.4 mmol) is dissolved in THF (100 mL) and is treated with tetra-butylammoniun fluoride (34 mL, 34 mmol, 1 M in THF). After stirring at room temperature for 30 minutes, the reaction is concentrated to dryness and the crude primary alcohol is purified by chromatography (20-40% EtOAc/hexanes) to give the intermediate alcohol as a white solid (4.94 g, 81%). A portion of this intermediate alcohol (2.05 g, 7.56 mmol) is suspended in $CH_2Cl_2$ (40 mL) and is treated with p-toluene-sulfonic acid monohydrate (2.16 g, 11.4 mmol) and 3,4-dihydro-2H-pyran (5.81 mL, 60.5 mmol). After stirring for 1 hour at room temperature the mixture is quenched with saturated aqueous $NaHCO_3$ and the aqueous phase is extracted with additional $CH_2Cl_2$ (2×). The combined organic extracts are dried over $Na_2SO_4$, filtered, and concentrated, and the desired product is purified by silica gel chromatography (0 to 15% EtOAc/hexane) to give a colorless oil (2.60 g, 97% yield for this step). MS (m/z): 356 (M+H).

The following compound is prepared essentially by the method of Preparation 2.

TABLE 1

| Prep. No. | Chemical name | Structure | ES/MS (m/z) (M + H) |
|---|---|---|---|
| 3 | Ethyl 4-(2,2-difluoro-ethylamino)-2-methyl-sulfanyl-pyrimidine-5-carboxylate | 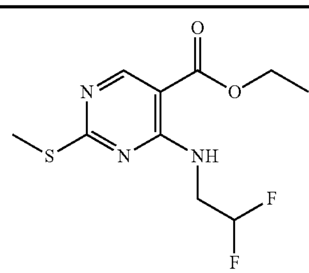 | 278 |

Preparation 4

(4-Amino-2-methylsulfanyl-pyrimidin-5-yl)methanol

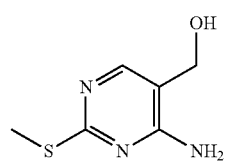

Scheme 1, Step B: $LiAlH_4$ (13.9 L, 14 mol, 1 M in THF) is added to a solution of ethyl 4-amino-2-sulfanyl-pyrimidine-5-carboxylate (3.5 Kg, 16.4 mol) in THF (45 L) at −5° C. over 1.5 hours. After stirring for 1 hour at −5 to 0° C., ice water (525 mL) and 15% aqueous NaOH (525 mL) are added, followed by additional ice water (1.6 L). After 30 minutes at 0° C. the quenched reaction mixture is filtered and the filter cake is washed with THF (1 L). The combined THF washes are dried ($Na_2SO_4$), filtered, and concentrated and the resulting crude product is slurried in a mixture of petroleum ether/EtOAc (3:1, 2 L), filtered, and dried again to provide the title compound as a yellow solid (2.1 Kg, 82% purity, 75% yield) which is used without further purification. MS (m/z): 172 (M+H).

The following compounds are prepared essentially by the method of Preparation 4.

TABLE 2

| Prep No. | Chemical name | Structure | ES/MS (m/z) (M + H) |
|---|---|---|---|
| 5 | [2-Methyl-sulfanyl-4-[[(1R)-1-methyl-2-tetrahydro-pyran-2-yloxy-ethyl] amino] pyrimidin-5-yl] methanol | 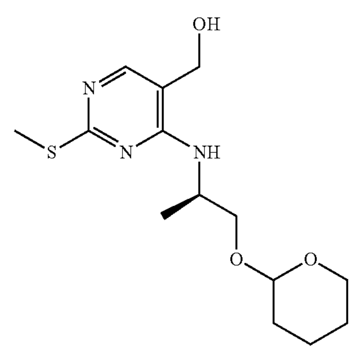 [SMILES: CSc1ncc(CO)c(N[C@H](C)COC2CCCCO2)n1] | 314 |
| 6 | [4-(2,2-Difluoro-ethyl-amino)-2-methyl-sulfanyl-pyrimidin-5-yl] methanol | 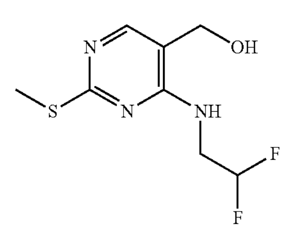 | 236 |

Preparation 7

7-Methylsulfanyl-1,4-dihydropyrimido[4,5-d][1,3]oxazin-2-one

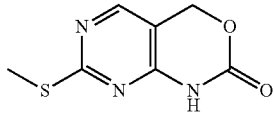

Scheme 1, Step C: Triphosgene (859 g, 2.9 mol) is added to a solution of (4-amino-2-methylsulfanyl-pyrimidin-5-yl)methanol (900 g, 5.26 mol) in THF (22.5 L) over 15 minutes at −30° C. DIPEA (2.449 g, 18.92 mol) is added over 1 hour, while maintaining the reaction temperature between −35 and −30° C. The reaction mixture is then poured over ice water (30 L) and 2-methyltetrahydrofuran (10 L) is added. The organic phase is washed with water and brine. The organic phase is dried over $Na_2SO_4$ and is concentrated to dryness. The crude product is slurried with petroleum ether/EtOAc (1:1), filtered, and concentrated to give a yellow solid which is carried on without further purification (890.5 g, 1.62 mol, 83% purity, 86% yield). MS (m/z): 198 (M+H).

The following compounds are prepared essentially by the method of Preparation 7.

Preparation 10

1-Ethyl-7-(methylthio)-1,4-dihydro-2H-pyrimido[4,5-d][1,3]oxazin-2-one

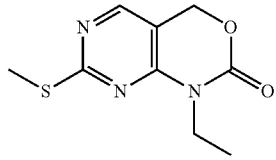

Scheme 1, Step D: To a solution of 7-methylsulfanyl-1,4-dihydropyrimido[4,5-d][1,3]oxazin-2-one (280 g, 1.42 mol) in NMP (2.24 L) is added $K_2CO_3$ (294.2 g, 2.13 mol) and ethyl iodide (336.3 g, 1.99 mol) at room temperature. The mixture is stirred for 16 hours at 50° C. and then diluted with $CH_2Cl_2$ (3 L) and water (6 L). The organic phase is separated and washed with water and brine and concentrated to dryness to give the crude title compound (286 g, 1.27 mol, 83% purity, 91% yield). MS (m/z): 226 (M+H).

The following compounds are prepared essentially by the method of Preparation 10.

TABLE 3

| Prep. No. | Chemical name | Structure | ES/MS (m/z) (M + H) |
|---|---|---|---|
| 8 | 7-Methylsulfanyl-1-[(1R)-1-methyl-2-tetrahydropyran-2-yloxy-ethyl]-4H-pyrimido[4,5-d][1,3]oxazin-2-one | 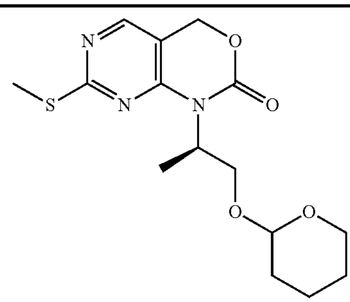 | 340 |
| 9 | 1-(2,2-difluoroethyl)-7-methylsulfanyl-4H-pyrimido[4,5-d][1,3]oxazin-2-one | 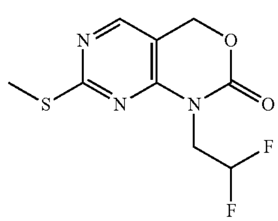 [SMILES: CSc1ncc2c(n1)N(CC(F)F)C(=O)OC2] | 262 |

TABLE 4

| Prep. No. | Chemical name | Structure | ES/MS (m/z) (M + H) |
|---|---|---|---|
| 11 | 1-Isopropyl-7-(methylthio)-1,4-dihydro-2H-pyrimido[4,5-d][1,3]oxazin-2-one | 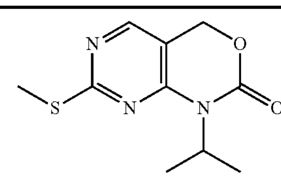 | 240 |

TABLE 4-continued

| Prep. No. | Chemical name | Structure | ES/MS (m/z) (M + H) |
|---|---|---|---|
| 12 | 1-Isobutyl-7-methylsulfanyl-4H-pyrimido[4,5-d][1,3]oxazin-2-one | 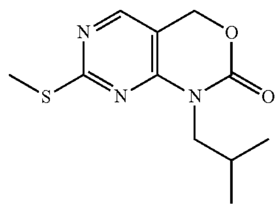 | 254 |

Alternative Preparation 10

1-Ethyl-7-(methylthio)-1,4-dihydro-2H-pyrimido[4,5-d][1,3]oxazin-2-one

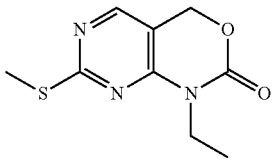

7-Methylsulfanyl-1,4-dihydropyrimido[4,5-d][1,3]oxazin-2-one (325 g, 1648.0 mmol) and DMF (2.4 L) are added together under a nitrogen atmosphere. To this clear solution is then added cesium carbonate (660 g, 2025.61 mmol) and the mixture is stirred for 30 minutes. Iodoethane (170 mL, 2120 mmol) is added dropwise over 30 minutes at 20° C. The reaction mixture is stirred at that temperature for 2.5 hours. The reaction mixture is slowly poured over ice-cold water and brine (1:1, 12 L). The resulting slurry is stirred for 2 hours. The solid is filtered, washed with water (2×2 L), and dried under vacuum with an air stream over 3 days to give the compound as a yellow solid (318 g, 99% purity, 87%). MS (m/z): 226 (M+H).

Preparation 13

1-Methyl-7-methylsulfanyl-4H-pyrimido[4,5-d][1,3]oxazin-2-one

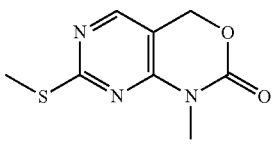

Scheme 1, Step D: To a solution of triphenylphosphine (1.61 g, 6.08 mmol) and 7-methylsulfanyl-1,4-dihydropyrimido[4,5-d][1,3]oxazin-2-one (1.00 g, 5.07 mmol) in THF (25 mL) is added MeOH (0.248 mL, 6.08 mmol) followed by dropwise addition of DIAD (1.21 mL, 6.08 mmol) at ambient temperature. After stirring overnight the solvent is removed under vacuum and the resulting yellow oil is purified by silica gel chromatography (40-50% EtOAc/hexanes) to give the title compound as a white solid (1.08 g, 5.11 mmol, quantitative). MS (m/z): 212 (M+H).

The following compound is prepared essentially by the method of Preparation 13.

TABLE 5

| Prep. No. | Chemical name | Structure | ES/MS (m/z) (M + H) |
|---|---|---|---|
| 14 | 1-(2-Fluoroethyl)-7-methylsulfanyl-4H-pyrimido[4,5-d][1,3]oxazin-2-one | 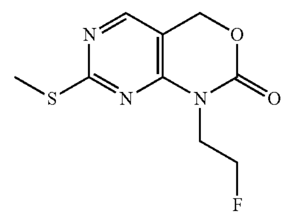 [SMILES: CSc1ncc2c(n1)N(CCF)C(=O)OC2] | 244 |

Preparation 15

1-Ethyl-7-(methylsulfonyl)-1,4-dihydro-2H-pyrimido[4,5-d][1,3]oxazin-2-one

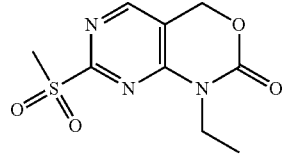 [SMILES: CCN1C(=O)OCc2cnc(S(C)(=O)=O)nc21]

Scheme 1, Step E: To a stirred solution of 1-ethyl-7-(methylthio)-1,4-dihydro-2H-pyrimido[4,5-d][1,3]oxazin-2-one (286 g, 1.24 mol) in ACN (2.8 L) and water (1.4 L) is added potassium peroxymonosulfate (1526 g, 2.48 mol) as a solid over 20 minutes, and the resulting mixture is stirred for 16 hours at 10-20° C. The reaction mixture is filtered and the obtained filter cake is washed with $CH_2Cl_2$. The combined filtrate and $CH_2Cl_2$ are washed with 5% $Na_2SO_3$, water, and brine. The organic phase is dried over $Na_2SO_4$ and concentrated to provide the title compound (133.8 g, 93% purity, 41% yield). MS (m/z): 258 (M+H).

The following compound is prepared essentially by the method of Preparation 15.

TABLE 6

| Prep. No. | Chemical name | Structure | ES/MS (m/z) (M + H) |
|---|---|---|---|
| 16 | 1-Isopropyl-7-methylsulfonyl-4H-pyrimido[4,5-d][1,3]oxazin-2-one | 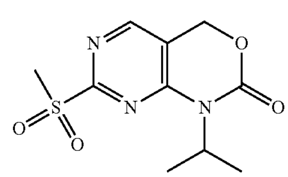 [SMILES: CC(C)N1C(=O)OCc2cnc(S(C)(=O)=O)nc21] | 272 |

Alternative Preparation 15

1-Ethyl-7-(methylsulfonyl)-1,4-dihydro-2H-pyrimido[4,5-d][1,3]oxazin-2-one

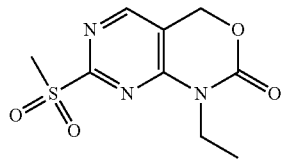 [SMILES: CCN1C(=O)OCc2cnc(S(C)(=O)=O)nc21]

1-Ethyl-7-methylsulfanyl-4H-pyrimido[4,5-d][1,3]oxazin-2-one (550 g, 2.44 mol) is combined with ACN (7 L) and water (3 L). To this solution at 12.5° C. is added potassium peroxymonosulfate (3070 g, 4.9 mol) in 10 portions over 100 minutes. After stirring at this temperature for 3 hours, the solids are filtered and washed with DCM (4 L). The layers are separated and the organic layer is washed sequentially with 5% $Na_2SO_3$ (3 L), water (2 L), brine (2 L), and dried over $Na_2SO_4$. The organic layers are filtered, combined, and concentrated under reduced pressure. After concentrating 95% of the solvent the precipitated solids are filtered to remove some color impurities. The filtered solids are washed twice with ACN (2×500 mL) and dried under vacuum with an air stream to get 340 g of product as first lot. The mother liquor is concentrated under reduced pressure to dryness. The residue is then triturated with minimum amount of ACN and the solids are filtered to get a second crop of 34 g. The combined lots give the title compound (374 g, 60%) as an off-white solid. MS (m/z): 258 (M+H).

Preparation 17

7-Methylsulfonyl-1-[(1R)-1-methyl-2-tetrahydropyran-2-yloxy-ethyl]-4H-pyrimido[4,5-d][1,3]oxazin-2-one

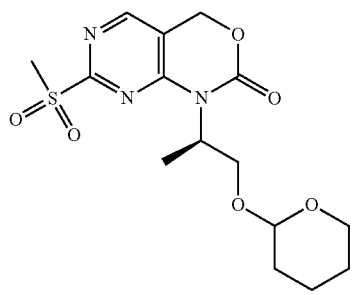 [SMILES: C[C@H](COC1CCCCO1)N1C(=O)OCc2cnc(S(C)(=O)=O)nc21]

Scheme 1, Step I: A suspension of 7-methylsulfanyl-1-[(1R)-1-methyl-2-tetrahydropyran-2-yloxy-ethyl]-4H-pyrimido[4,5-d][1,3]oxazin-2-one (700 mg, 2.06 mmol) in $CH_2Cl_2$ (10 mL) is treated with mCPBA (1.07 g, 4.5 mmol, 70-75% reagent grade) at room temperature. After 20 minutes, the solids are filtered and washed with additional $CH_2Cl_2$. The organic filtrates are combined and washed with saturated aqueous $NaHCO_3$ (2×) and brine, dried ($Na_2SO_4$), filtered, and concentrated to dryness. The material is purified with silica gel chromatography to give the title compound as a colorless oil (589 mg, 77%). MS (m/z): 372 (M+H).

The following compounds are prepared essentially by the method of Preparation 17.

TABLE 7

| Prep. No. | Chemical name | Structure | ES/MS (m/z) (M + H) |
|---|---|---|---|
| 18 | 1-Isobutyl-7-methylsulfonyl-4H-pyrimido[4,5-d][1,3]oxazin-2-one | 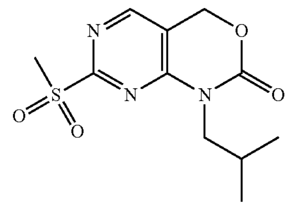 [SMILES: CC(C)CN1C(=O)OCc2cnc(S(C)(=O)=O)nc21] | 286 |
| 19 | 1-Methyl-7-methylsulfonyl-4H-pyrimido[4,5-d][1,3]oxazin-2-one | 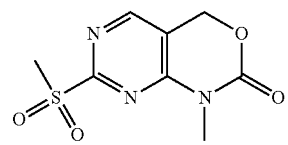 [SMILES: CN1C(=O)OCc2cnc(S(C)(=O)=O)nc21] | 244 |
| 20 | 1-(2,2-difluoroethyl)-7-methylsulfonyl-4H-pyrimido[4,5-d][1,3]oxazin-2-one | 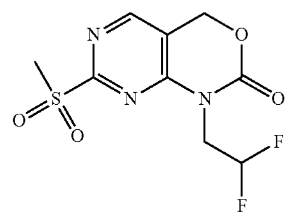 [SMILES: CS(=O)(=O)c1ncc2c(n1)N(CC(F)F)C(=O)OC2] | 294 |
| 21 | 1-(2-fluoroethyl)-7-methylsulfonyl-4H-pyrimido[4,5-d][1,3]oxazin-2-one | 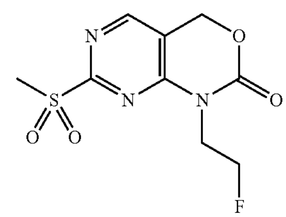 [SMILES: CS(=O)(=O)c1ncc2c(n1)N(CCF)C(=O)OC2] | 276 |

Preparation 22

(S)-(4-(1-Aminoethyl)phenyl)methanol

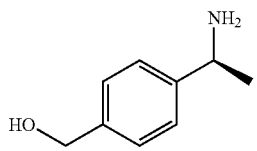

Scheme 2, Step J: To a stirred solution of methyl (S)-4-(1-aminoethyl)benzoate (100 g, 558 mmol) in THF (2.2 L) is added $LiAlH_4$ (560 mL, 560 mmol, 1 M in THF) over 1 hour, while maintaining the temperature of the reaction below 30° C. The reaction mixture is stirred for 2 hours and then cooled to 0° C. Water (100 mL) is added dropwise followed by anhydrous $Na_2SO_4$ (1 Kg), and the resulting mixture is stirred overnight. The mixture is filtered over diatomaceous earth and the resulting white solid is dried under vacuum to give the title compound (81.8 g, 97%). MS (m/z): 135 (M–$NH_2$).

Preparation 23

(1S)-1-[4-(Chloromethyl)phenyl]ethanamine hydrochloride

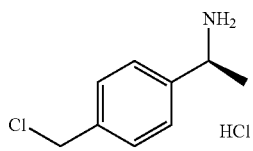

Scheme 2, Step K: To a solution of (S)-(4-(1-aminoethyl)phenyl)methanol (81.8 g, 541 mmol) in CH$_2$Cl$_2$ (2.5 L) is added SOCl$_2$ (80 mL, 1.1 mmol) dropwise over 30 minutes while maintaining a reaction temperature below 25° C. The thick precipitate that is formed dissolves over the course of the reaction. After stirring for 4 hours, the mixture is concentrated to give a yellow solid. ACN (1 L) is added and the mixture is concentrated to 500 mL and the resulting solid is filtered to give an off-white solid that is dried under vacuum. The product is obtained as an off-white solid after drying and the mother liquor can also be concentrated to provide less pure product (~20 g) as a yellow solid. The two product lots are combined to give the title compound (111 g, 78%). MS (m/z): 170 (M+H).

Preparation 24 tert-Butyl 4-[[4-[(1S)-1-[(2,2,2-trifluoroacetyl)amino]ethyl]phenyl]-methyl]-piperazine-1-carboxylate

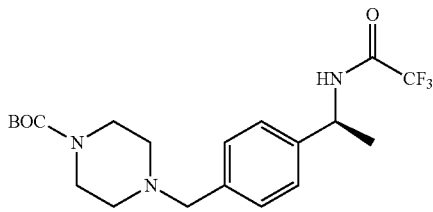 [SMILES: C[C@H](NC(=O)C(F)(F)F)c1ccc(CN2CCN(C(=O)OC(C)(C)C)CC2)cc1]

Scheme 2, Step L: To a solution of (1S)-1-[4-(chloromethyl)phenyl]ethanamine hydrochloride (10 g, 48.5 mmol) in CH$_2$Cl$_2$ (160 mL) is added trifluoroacetic anhydride (8.2 mL, 58 mmol) at 0° C. TEA (15 mL, 108 mmol) is added while maintaining the addition temperature below 5° C. After stirring for 1 hour at 0° C. the reaction mixture is concentrated to dryness and ACN (120 mL) is added followed by tert-butyl piperazine-1-yl carbonate (13.5 g, 72.5 mmol). K$_2$CO$_3$ (20 g, 144.7 mmol) is added and the mixture is heated to 60° C. and stirred for 17 hours. The solvent is removed by vacuum and EtOAc (1 L) is added. The solid is filtered away and the EtOAc is washed with water and brine. The organic phase is dried over Na$_2$SO$_4$, filtered, and concentrated to dryness. The resulting crude product is purified by silica gel chromatography (10 to 50% acetone/CH$_2$Cl$_2$) to give the title compound as a white foam (15.8 g, 78%). MS (m/z): 416 (M+H).

Preparation 25 tert-Butyl 4-[[4-[(1S)-1-aminoethyl]phenyl]methyl]piperazine-1-carboxylate

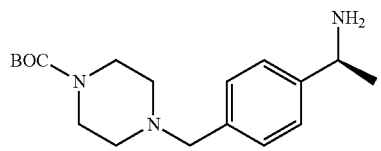 [SMILES: C[C@H](N)c1ccc(CN2CCN(C(=O)OC(C)(C)C)CC2)cc1]

Scheme 2, Step M, substep 1: To a solution of tert-butyl 4-[[4-[(1S)-1-[(2,2,2-trifluoroacetyl)amino]ethyl]phenyl]-methyl]-piperazine-1-carboxylate (203 g, 0.489 mol) in EtOH (2.4 L) is added 5 M aq. NaOH (480 mL, 2.40 mol) at room temperature. After stirring at room temperature for 3.5 hours, the reaction mixture is concentrated to remove most of the EtOH. EtOAc (2 L) is added to dissolve the residue and the solution is washed with water and brine. The combined aqueous phases are extracted with EtOAc (2×). The combined organic extracts are dried over Na$_2$SO$_4$, filtered, and concentrated to dryness to give the crude title compound as a yellow viscous oil (156 g, 93%) which is carried on without further purification. MS (m/z): 320 (M+H).

Preparation 26 tert-Butyl 4-[[4-[(1S)-1-[(1-isopropyl-2-oxo-4H-pyrimido[4,5-d][1,3]oxazin-7-yl)amino]ethyl]phenyl]methyl]piperazine-1-carboxylate

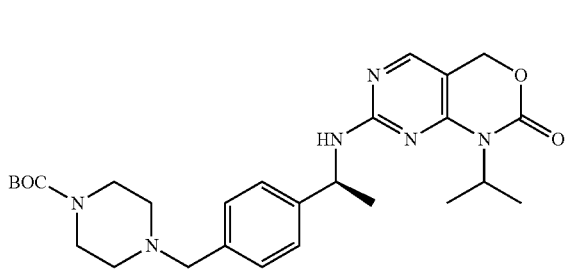 [SMILES: CC(C)N1C(=O)OCc2cnc(N[C@@H](C)c3ccc(CN4CCN(C(=O)OC(C)(C)C)CC4)cc3)nc21]

Scheme 2, Step M, substep 2: To a solution of tert-butyl 4-[[4-[(1S)-1-aminoethyl]phenyl]methyl]piperazine-1-carboxylate (46.7 g, 136 mmol) and 1-isopropyl-7-methylsulfonyl-4H-pyrimido[4,5-d][1,3]oxazin-2-one (40.6 g, 150 mmol) in DMSO (272 mL) is added CsF (20.7 g, 136 mmol) and DIPEA (23.7 mL, 136 mmol). The mixture is stirred at 75-80° C. for 17 hours. The mixture is then cooled to room temperature, diluted with water (1.2 L), extracted with EtOAc (3×), washed with brine, dried (Na$_2$SO$_4$), filtered, and concentrated to dryness. The resulting crude product is purified by silica gel chromatography (30 to 60% acetone/CH$_2$Cl$_2$) to give the title compound as a white foam (54 g, 78%). MS (m/z): 511 (M+H).

Preparation 27

1-Isopropyl-7-[[(1S)-1-[4-(piperazin-1-ylmethyl)phenyl]ethyl]amino]-4H-pyrimido[4,5-d][1,3]oxazin-2-one hydrochloride

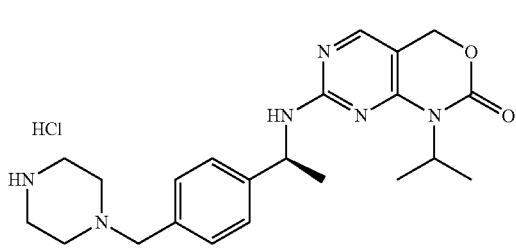 [SMILES: CC(C)N1C(=O)OCc2cnc(N[C@@H](C)c3ccc(CN4CCNCC4)cc3)nc21 ; Cl]

Scheme 2, Step N, substep 1: To a solution of tert-butyl 4-[[4-[(1S)-1-[(1-isopropyl-2-oxo-4H-pyrimido[4,5-d][1,3]oxazin-7-yl)amino]ethyl]phenyl]methyl]piperazine-1-carboxylate (54 g, 106 mmol) in dioxane (270 mL) is added HCl (264 mL, 4 M in dioxane), while maintaining the internal temperature below 35° C. MeOH (100 mL) is then added to facilitate stirring. The mixture is stirred at 30° C. for 2 hours and is then concentrated to give a white solid that is dried under vacuum. The title product is obtained after drying as a light yellow solid (60 g, quantitative) which is carried on without further purification. MS (m/z): 411 (M+H).

Preparation 28 tert-Butyl 4-[[4-[(1S)-1-[(1-ethyl-2-oxo-4H-pyrimido[4,5-d][1,3]oxazin-7-yl)amino]ethyl]phenyl]methyl]piperazine-1-carboxylate

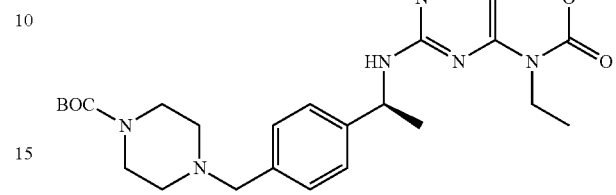

Scheme 2, Step N, substep 1: To a solution of tert-butyl 4-[[4-[(1S)-1-aminoethyl]phenyl]methyl]piperazine-1-carboxylate (52 g, 151.4 mmol) and 1-ethyl-7-methylsulfonyl-4H-pyrimido[4,5-d][1,3]oxazin-2-one (42.8 g, 166 mmol) in DMSO (300 mL) is added CsF (23 g, 151.4 mmol) and DIPEA (26.5 mL, 152 mmol). The mixture is stirred at 75-80° C. for 4 hours. The mixture is cooled to room temperature, diluted with water (1.2 L), extracted with EtOAc (3×), washed with brine, dried ($Na_2SO_4$), filtered, and concentrated. The crude product is purified by silica gel chromatography (50 to 75% [10% EtOH/$CH_2Cl_2$]/hexanes) to give a white foam (53.3 g, 71%). MS (m/z): 497 (M+H).

The following compounds are prepared essentially by the method of Preparation 28.

TABLE 8

| Prep. No. | Chemical name | Structure | ES/MS (m/z) (M + H) |
|---|---|---|---|
| 29 | Allyl 4-[[4-[(1S)-1-[(1-isobutyl-2-oxo-4H-pyrimido[4,5-d][1,3]oxazin-7-yl)amino)ethyl]phenyl]methyl]piperazine-1-carboxylate | 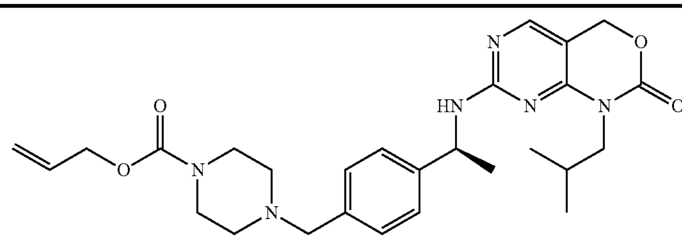 | 509 |
| 30 | tert-Butyl 3-[[4-[(1S)-1-[(1-ethyl-2-oxo-4H-pyrimido[4,5-d][1,3]oxazin-7-yl)amino]ethyl]phenyl]methoxy]azetidine-1-carboxylate | 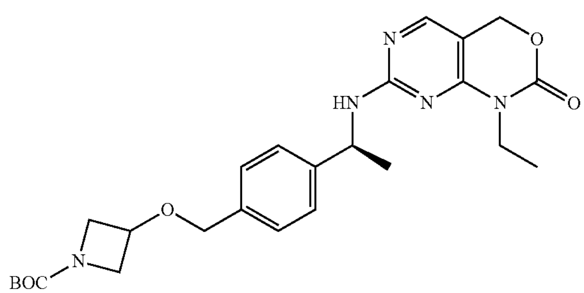 [SMILES: CCN1C(=O)OCc2cnc(N[C@@H](C)c3ccc(COC4CN(C(=O)OC(C)(C)C)C4)cc3)nc21] | 484 |
| 31 | 7-[[(1S)-1-[4-(Hydroxymethyl)phenyl]ethyl]amino]-1-isobutyl-4H-pyrimido[4,5-d][1,3]oxazin-2-one | 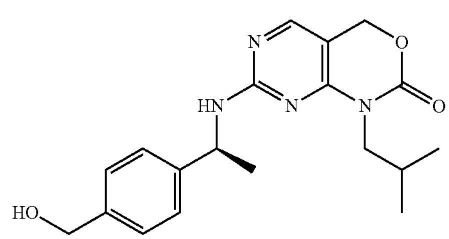 [SMILES: CC(C)CN1C(=O)OCc2cnc(N[C@@H](C)c3ccc(CO)cc3)nc21] | 357 |

TABLE 8-continued

| Prep. No. | Chemical name | Structure | ES/MS (m/z) (M + H) |
|---|---|---|---|
| 32 | 7-[[(1S)-1-(4-Bromophenyl)ethyl]amino]-1-isopropyl-4H-pyrimido[4,5-d][1,3]oxazin-2-one | 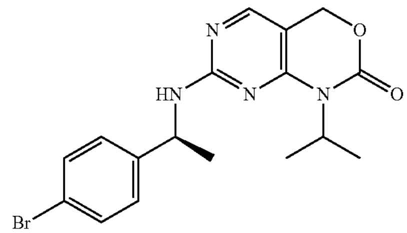 [SMILES: CC(C)N1C(=O)OCc2cnc(N[C@@H](C)c3ccc(Br)cc3)nc21] | ($^{79}$Br/$^{81}$Br) 391/393 |
| 33 | 7-[[(1S)-1-(4-Bromophenyl)ethyl]amino]-1-ethyl-4H-pyrimido[4,5-d][1,3]oxazin-2-one | 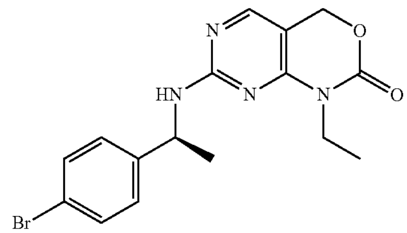 [SMILES: CCN1C(=O)OCc2cnc(N[C@@H](C)c3ccc(Br)cc3)nc21] | ($^{79}$Br/$^{81}$Br) 377/379 (M + H, |
| 34 | 7-[[(1S)-1-[4-(Hydroxymethyl)phenyl]ethyl]amino]-1-isopropyl-4H-pyrimido[4,5-d][1,3]oxazin-2-one | 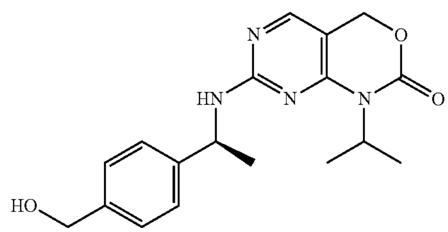 [SMILES: CC(C)N1C(=O)OCc2cnc(N[C@@H](C)c3ccc(CO)cc3)nc21] | 343 |
| 35 | tert-Butyl 3-[[4-[(1S)-1-[(1-isopropyl-2-oxo-4H-pyrimido[4,5-d][1,3]oxazin-7-yl)amino]ethyl]phenoxy]methyl]azetidine-1-carboxylate | 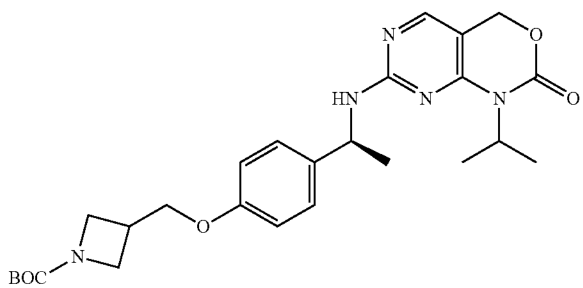 [SMILES: CC(C)N1C(=O)OCc2cnc(N[C@@H](C)c3ccc(OCC4CN(C(=O)OC(C)(C)C)C4)cc3)nc21] | 498 |
| 36 | tert-Butyl-3-[[4-[(1S)-1-[(1-ethyl-2-oxo-4H-pyrimido[4,5-d][1,3]oxazin-7-yl)amino]ethyl]phenyl]methyl-methyl-amino]azetidine-1-carboxylate | 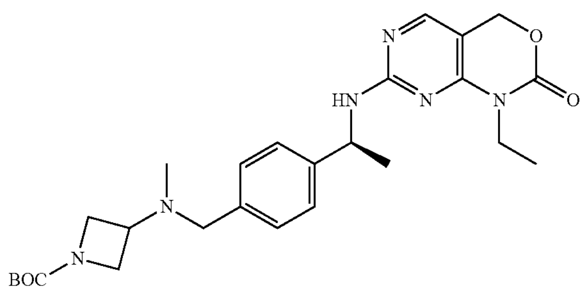 [SMILES: CCN1C(=O)OCc2cnc(N[C@@H](C)c3ccc(CN(C)C4CN(C(=O)OC(C)(C)C)C4)cc3)nc21] | 497 |
| 37 | tert-Butyl 4-[[4-[(1S)-1-[[1-[(1R)-1-methyl-2-tetrahydropyran-2-yloxy-ethyl]-2-oxo-4H-pyrimido[4,5-d][1,3]oxazin-7-yl]amino]ethyl]phenyl]methyl]piperazine-1-carboxylate | 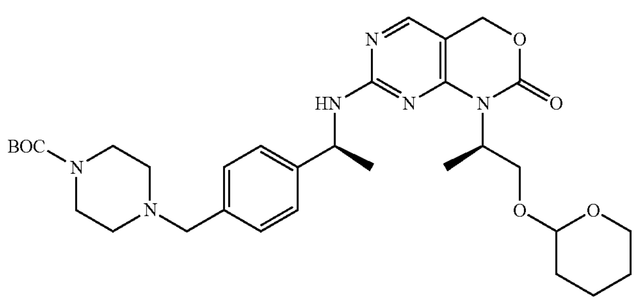 [SMILES: C[C@H](Nc1ncc2c(n1)N([C@H](C)COC1CCCCO1)C(=O)OC2)c1ccc(CN2CCN(C(=O)OC(C)(C)C)CC2)cc1] | 611 |

TABLE 8-continued

| Prep. No. | Chemical name | Structure | ES/MS (m/z) (M + H) |
|---|---|---|---|
| 38 | tert-Butyl 3-[[4-[(1S)-1-[(1-isobutyl-2-oxo-4H-pyrimido[4,5-d][1,3]oxazin-7-yl)amino]ethyl]phenyl]methoxy]azetidine-1-carboxylate | 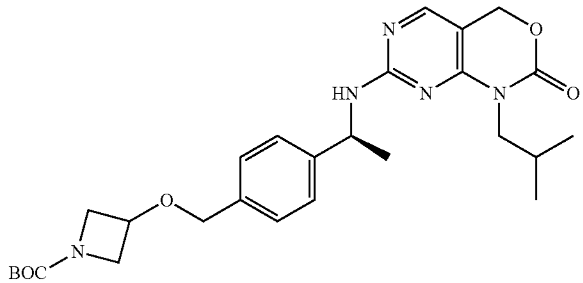 [SMILES: CC(C)CN1C(=O)OCc2cnc(N[C@@H](C)c3ccc(COC4CN(C(=O)OC(C)(C)C)C4)cc3)nc21] | 512 |
| 39 | tert-Butyl 6-[[4-[(1S)-1-[(1-ethyl-2-oxo-4H-pyrimido[4,5-d][1,3]oxazin-7-yl)amino]ethyl]phenyl]methyl]-2,6-diazaspiro[3.3]heptane-2-carboxylate | 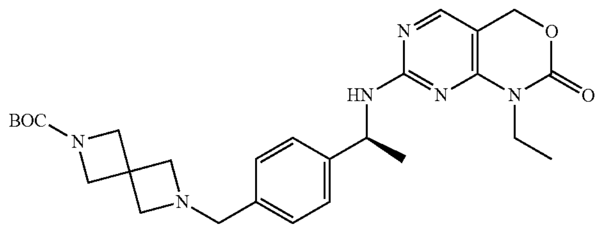 [SMILES: CCN1C(=O)OCc2cnc(N[C@@H](C)c3ccc(CN4CC5(C4)CN(C(=O)OC(C)(C)C)C5)cc3)nc21] | 509 |
| 40 | 1-Ethyl-7-[[(1S)-1-[3-fluoro-4-(hydroxymethyl)phenyl]ethyl]amino]-4H-pyrimido[4,5-d][1,3]oxazin-2-one | 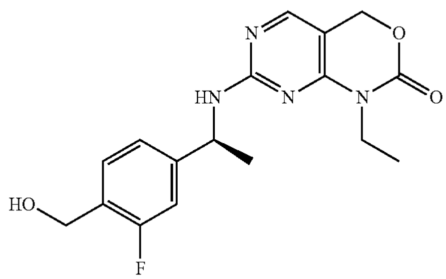 [SMILES: CCN1C(=O)OCc2cnc(N[C@@H](C)c3ccc(CO)c(F)c3)nc21] | 347 |
| 41 | tert-Butyl 3-[[4-[(1S)-1-[(1-ethyl-2-oxo-4H-pyrimido[4,5-d][1,3]oxazin-7-yl)amino]ethyl]phenoxy]methyl]azetidine-1-carboxylate | 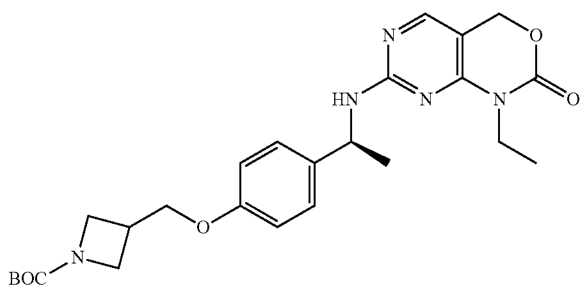 [SMILES: CCN1C(=O)OCc2cnc(N[C@@H](C)c3ccc(OCC4CN(C(=O)OC(C)(C)C)C4)cc3)nc21] | 484 |
| 42 | tert-Butyl 4-[[4-[(1S)-1-[(1-methyl-2-oxo-4H-pyrimido[4,5-d][1,3]oxazin-7-yl)amino]ethyl]phenyl]methyl]piperazine-1-carboxylate | 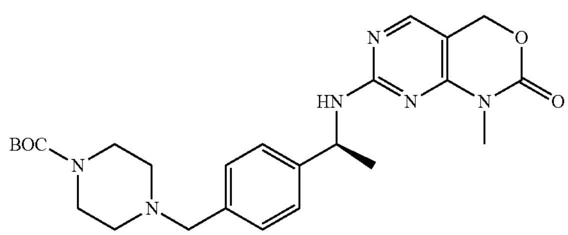 [SMILES: C[C@H](Nc1ncc2c(n1)N(C)C(=O)OC2)c1ccc(CN2CCN(C(=O)OC(C)(C)C)CC2)cc1] | 483 |
| 43 | tert-butyl 4-[[4-[(1S)-1-[[1-(2,2-difluoroethyl)-2-oxo-4H-pyrimido[4,5-d][1,3]oxazin-7-yl]amino]ethyl]phenyl]methyl]piperazine-1-carboxylate | 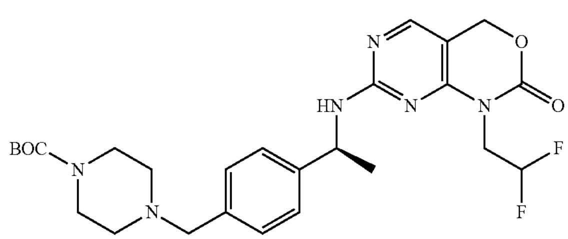 [SMILES: C[C@H](Nc1ncc2c(n1)N(CC(F)F)C(=O)OC2)c1ccc(CN2CCN(C(=O)OC(C)(C)C)CC2)cc1] | 533 |

TABLE 8-continued

| Prep. No. | Chemical name | Structure | ES/MS (m/z) (M + H) |
|---|---|---|---|
| 44 | tert-butyl 4-[[4-[(1S)-1-[[1-(2-fluoroethyl)-2-oxo-4H-pyrimido[4,5-d][1,3]oxazin-7-yl]amino]ethyl]phenyl]methyl]piperazine-1-carboxylate | 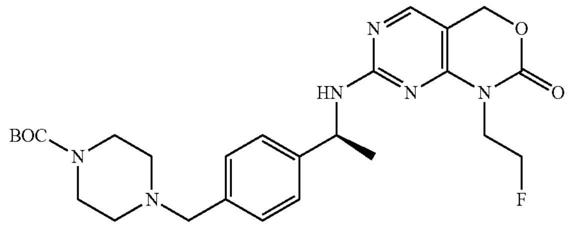 [SMILES: C[C@H](Nc1ncc2c(n1)N(CCF)C(=O)OC2)c1ccc(CN2CCN(C(=O)OC(C)(C)C)CC2)cc1] | 515 |
| 45 | 1-ethyl-7-[[(1S)-1-(4-hydroxyphenyl)ethyl]amino]-4H-pyrimido[4,5-d][1,3]oxazin-2-one | 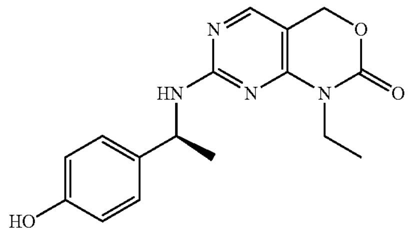 [SMILES: CCN1C(=O)OCc2cnc(N[C@@H](C)c3ccc(O)cc3)nc21] | 315 |

Alternative Preparation 28 tert-Butyl 4-[[4-[(1S)-1-[(1-ethyl-2-oxo-4H-pyrimido[4,5-d][1,3]oxazin-7-yl)amino]ethyl]phenyl]methyl]piperazine-1-carboxylate

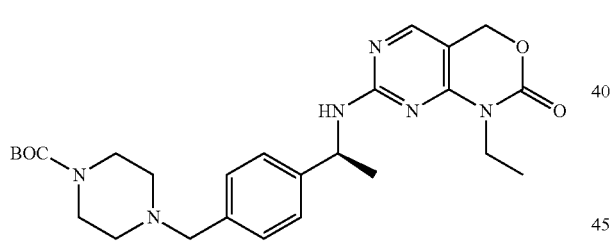

tert-Butyl 4-[[4-[(1S)-1-aminoethyl]phenyl]methyl]piperazine-1-carboxylate (400 g, 1252 mmol) and DMSO (2.2 L) are added together. To this solution is then sequentially added 1-ethyl-7-methylsulfonyl-4H-pyrimido[4,5-d][1,3]oxazin-2-one (325 g, 1200.1 mmol), CsF (200 g, 1316.59 mmol) and DIPEA (240 mL, 1380 mmol). The reaction mixture is then heated at 75° C. for 5 hours and allowed to warm to room temperature overnight with gentle stirring. The reaction mixture is slowly poured over ice-cold water/brine (1:1). The precipitated solids are filtered, washed with water (2×1.5 L), and dried under vacuum with an air stream overnight. The wet cake obtained (800 g) is taken forward without further purification.

Preparation 46

1-Ethyl-7-[[(1S)-1-[4-(piperazin-1-ylmethyl)phenyl]ethyl]amino]-4H-pyrimido[4,5-d][1,3]oxazin-2-one hydrochloride

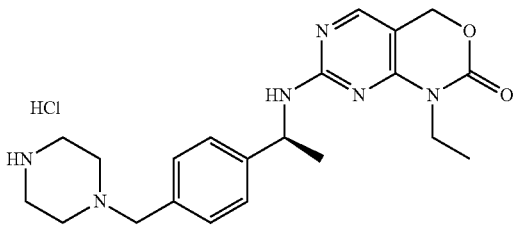 [SMILES: CCN1C(=O)OCc2cnc(N[C@@H](C)c3ccc(CN4CCNCC4)cc3)nc21 ; Cl]

Scheme 2, Step N, substep 1: To a solution of tert-butyl 4-[[4-[(1S)-1-[(1-ethyl-2-oxo-4H-pyrimido[4,5-d][1,3]oxazin-7-yl)amino]ethyl]phenyl]methyl]piperazine-1-carboxylate (48.3 g, 97.3 mmol) in a mixture of dioxane (140 mL) and MeOH (100 mL) is added HCl (4 M in dioxane, 243 mL) over 20 minutes while maintaining an internal temperature below 30° C. The mixture is stirred at 30° C. for 1 hour and it is then concentrated to dryness to provide a white solid which is dried under vacuum overnight to give the title compound (54 g, quantitative). MS (m/z): 397 (M+H).

The following compounds are prepared essentially by the method of Preparation 46.

TABLE 9

| Prep. No. | Chemical name | Structure | ES/MS (m/z) (M + H) |
|---|---|---|---|
| 47 | 7-[[(1S)-1-[4-[[Azetidin-3-yl(methyl)amino]methyl]phenyl]ethyl]amino]-1-ethyl-4H-pyrimido[4,5-d][1,3]oxazin-2-one | 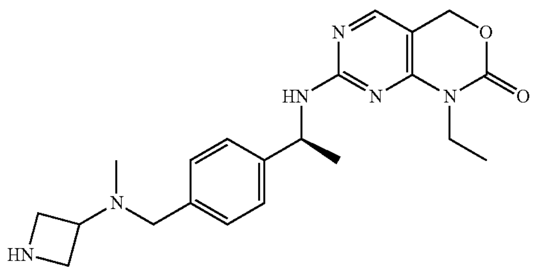 [SMILES: CCN1C(=O)OCc2cnc(N[C@@H](C)c3ccc(CN(C)C4CNC4)cc3)nc21] | 397 |
| 48 | 1-[(1R)-2-Hydroxy-1-methyl-ethyl]-7-[[(1S)-1-[4-(piperazin-1-ylmethyl)phenyl]ethyl]amino]-4H-pyrimido[4,5-d][1,3]oxazin-2-one dihydrochloride | 2HCl | 427 |

Alternative Preparation 46

1-Ethyl-7-[[(1S)-1-[4-(piperazin-1-ylmethyl)phenyl]ethyl]amino]-4H-pyrimido[4,5-d][1,3]oxazin-2-one

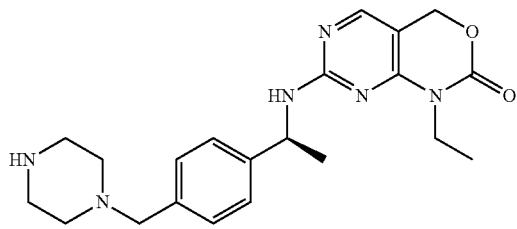 [SMILES: CCN1C(=O)OCc2cnc(N[C@@H](C)c3ccc(CN4CCNCC4)cc3)nc21]

Crude wet tert-butyl-4-[[4-[(1S)-1-[(1-ethyl-2-oxo-4H-pyrimido[4,5-d][1,3]oxazin-7-yl)amino]ethyl]phenyl]methyl]piperazine-1-carboxylate (800 g, theoretical 1252 mmol) is dissolved in 1,4-dioxane (2 L). HCl (3.6 L, 29.2 mol, aqueous 8 mol/L) is added over about 30 minutes with cooling at 15° C. followed by the addition of DCM (1 L). The layers are separated and the acidic solution is washed with DCM (2×500 mL). To the aqueous phase is added 20% $Na_2CO_3$ to pH 9.5-10, at room temperature. DCM (1 L) is added, the layers are separated, and the aqueous layer is extracted with DCM (2×500 mL). The combined organic extracts are washed with brine, dried over $Na_2SO_4$, and concentrated to dryness to a yellow foaming oil that is purified via silica gel filtration eluting with 90:9:1 hexanes, DCM, EtOH to 70:29:1 to give the title compound (219 g, 53% in 2 steps) as yellow foaming solid. MS (m/z): 397 (M+H).

Preparation 49

Allyl 4-[[4-[(1S)-1-aminoethyl]phenyl]methyl]piperazine-1-carboxylate dihydrochloride

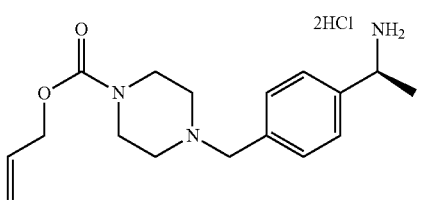 [SMILES: "2HCl" ; C=CCOC(=O)N1CCN(Cc2ccc([C@H](C)N)cc2)CC1]

Scheme 2, Step L, substep 2: A pressure vessel is equipped with (1S)-1-[4-(chloromethyl)phenyl]ethanamine hydrochloride (850 mg, 4.12 mmol), alloc-N-piperazine (1.43 g, 8.25 mmol), $K_2CO_3$ (1.71 g, 12.4 mmol) and ACN (20.6 mL). The resulting suspension is capped and heated at 60° C. for 24 hours and then concentrated. The crude white solid is purified by silica gel chromatography using 0 to 10% 7 N—$NH_3$ in MeOH/$CH_2Cl_2$ to provide a mixture of the desired product and unreacted alloc-N-piperazine. This material is repurified by reverse phase chromatography (0 to 100% ACN/aq 10 mM $NaHCO_3$) to give the title compound as a colorless oil (900 mg, 71%). MS (m/z): 171 (M+H).

The following compounds are prepared essentially by the method of Preparation 49.

TABLE 10

| Prep. No. | Chemical name | Structure | ES/MS (m/z) (M + H) |
|---|---|---|---|
| 50 | tert-Butyl 3-[[4-[(1S)-1-aminoethyl]phenyl]methyl-methyl-amino]azetidine-1-carboxylate | 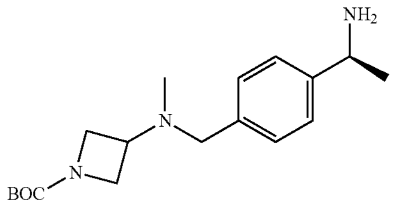 [SMILES: C[C@H](N)c1ccc(CN(C)C2CN(C(=O)OC(C)(C)C)C2)cc1] | 320 |
| 51 | tert-Butyl 6-[[4-[(1S)-1-aminoethyl]phenyl]methyl]-2,6-diazaspiro[3.3]heptane-2-carboxylate | 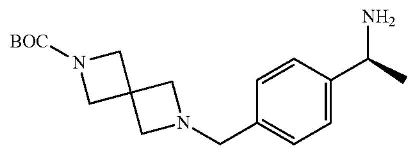 [SMILES: C[C@H](N)c1ccc(CN2CC3(C2)CN(C(=O)OC(C)(C)C)C3)cc1] | 332 |

Preparation 52

1-Isobutyl-7-[[(1S)-1-[4-(piperazin-1-ylmethyl)phenyl]ethyl]amino]-4H-pyrimido[4,5-d][1,3]oxazin-2-one

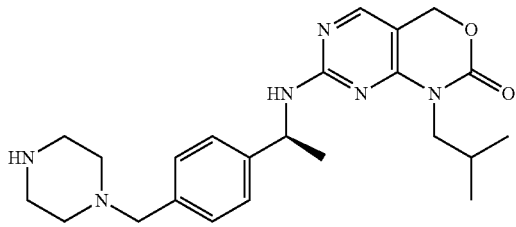 [SMILES: CC(C)CN1C(=O)OCc2cnc(N[C@@H](C)c3ccc(CN4CCNCC4)cc3)nc21]

Scheme 2, Step N, substep 1, Allyl 4-[[4-[(1S)-1-[(1-isobutyl-2-oxo-4H-pyrimido[4,5-d][1,3]oxazin-7-yl)amino]ethyl]-phenyl]methyl]piperazine-1-carboxylate (1.15 g, 2.26 mmol) is dissolved in THF (22.6 mL). Dimedone (3.27 g, 22.6 mmol) and Pd(PPh₃)₄ (131 mg, 0.113 mmol, 5 mol %) are added sequentially and the mixture is stirred at room temperature for 30 minutes. The reaction mixture is passed over an SCX cartridge that is prewashed with MeOH. The undesired reagents are eluted with MeOH and the desired product is eluted with 2 N NH₃ in MeOH. The ammoniated eluent is concentrated to give the title compound as a white solid (980 mg, quantitative).

Preparation 53 tert-Butyl 3-[[4-[(1S)-1-aminoethyl]phenyl]methoxy]azetidine-1-carboxylate

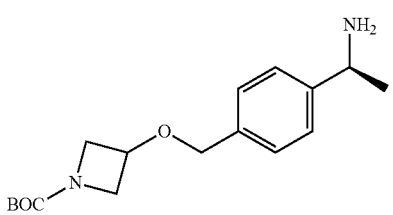 [SMILES: C[C@H](N)c1ccc(COC2CN(C(=O)OC(C)(C)C)C2)cc1]

Scheme 2, Step L, substep 2: tert-Butyl 3-hydroxyazetidine-1-carboxylate (4.19 g, 23.7 mmol) is dissolved in DMA (23.7 mL) and NaH (1.4 g, 35.6 mmol, 60 wt %) is added at room temperature. After stirring for 3 minutes, (1S)-1-[4-(chloromethyl)phenyl]ethanamine hydrochloride (2.44 g, 11.9 mmol) is added in a minimum amount of DMA and the reaction is allowed to stir for 1 hour. The mixture is diluted with half-saturated brine and is extracted with EtOAc (3×). The organic extracts are combined, dried (MgSO₄), filtered, and concentrated to provide the crude product as a yellow oil containing residual DMA. The product is carried on without further purification (100% yield assumed): MS (m/z): 307 (M+H).

Preparation 54

7-[[(1S)-1-[4-(Azetidin-3-yloxymethyl)phenyl]ethyl]amino]-1-ethyl-4H-pyrimido[4,5-d][1,3]oxazin-2-one

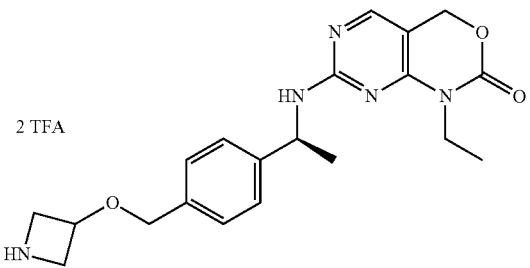 [SMILES: CCN1C(=O)OCc2cnc(N[C@@H](C)c3ccc(COC4CNC4)cc3)nc21]

Scheme 2, Step N, substep 1: tert-Butyl 3-[[4-[(1S)-1-[(1-ethyl-2-oxo-4H-pyrimido[4,5-d][1,3]oxazin-7-yl)amino]ethyl]phenyl]methoxy]azetidine-1-carboxylate (1.85 g, 3.83 mmol) is dissolved in CH₂Cl₂ (29 mL) and TFA (2.89 mL, 38.3 mmol) is added at 0° C. and stirred for 6 hours while the cold bath expires to room temperature. The solvent and acid are removed by vacuum to give the title compound as a light yellow oil (3.66 g, 99%). MS (m/z): 384 (M+H).

The following compounds are prepared essentially by the method of Preparation 54.

TABLE 11

| Prep. No. | Chemical name | Structure | ES/MS (m/z) (M + H) |
|---|---|---|---|
| 55 | 7-[[(1S)-1-[4-(2,6-Diazaspiro[3.3]heptan-2-ylmethyl)phenyl]ethyl]amino]-1-isobutyl-4H-pyrimido[4,5-d][1,3]oxazin-2-one | 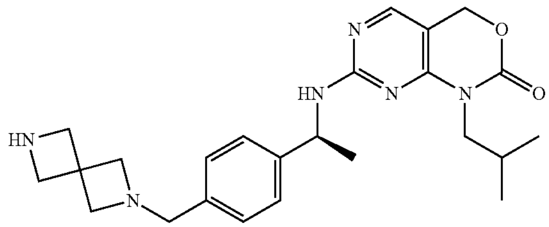 [SMILES: CC(C)CN1C(=O)OCc2cnc(N[C@@H](C)c3ccc(CN4CC5(CNC5)C4)cc3)nc21] | 437 |
| 56 | 1-Isopropyl-7-[[(1S)-1-(4-piperazin-1-ylphenyl)ethyl]amino]-4H-pyrimido[4,5-d][1,3]oxazin-2-one | 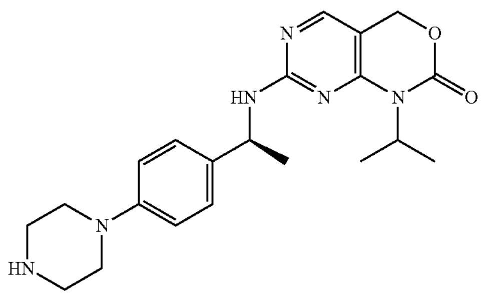 [SMILES: CC(C)N1C(=O)OCc2cnc(N[C@@H](C)c3ccc(N4CCNCC4)cc3)nc21] | 397 |
| 57 | 7-[[(1S)-1-[4-[2-(Azetidin-3-yl)ethyl]phenyl]ethyl]amino]-1-ethyl-4H-pyrimido[4,5-d][1,3]oxazin-2-one | 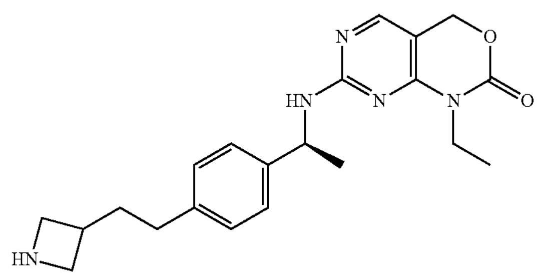 [SMILES: CCN1C(=O)OCc2cnc(N[C@@H](C)c3ccc(CCC4CNC4)cc3)nc21] | 382 |
| 58 | 7-[[(1S)-1-[4-(2,7-Diazaspiro[3.5]nonan-2-ylmethyl)phenyl]ethyl]amino]-1-isopropyl-4H-pyrimido[4,5-d][1,3]oxazin-2-one | 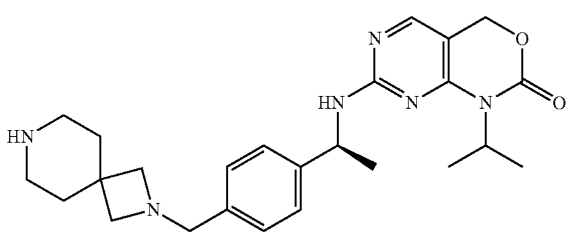 [SMILES: CC(C)N1C(=O)OCc2cnc(N[C@@H](C)c3ccc(CN4CC5(CCNCC5)C4)cc3)nc21] | 451 |
| 59 | 7-[[(1S)-1-[4-(Azetidin-3-ylmethoxy)phenyl]ethyl]amino]-1-isopropyl-4H-pyrimido[4,5-d][1,3]oxazin-2-one | 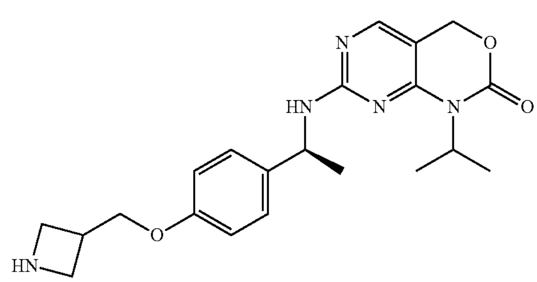 [SMILES: CC(C)N1C(=O)OCc2cnc(N[C@@H](C)c3ccc(OCC4CNC4)cc3)nc21] | 398 |

TABLE 11-continued

| Prep. No. | Chemical name | Structure | ES/MS (m/z) (M + H) |
|---|---|---|---|
| 60 | 1-Ethyl-7-[[(1S)-1-[4-[[methyl(4-piperidyl)amino]methyl]phenyl]ethyl]amino]-4H-pyrimido[4,5-d][1,3]oxazin-2-one | 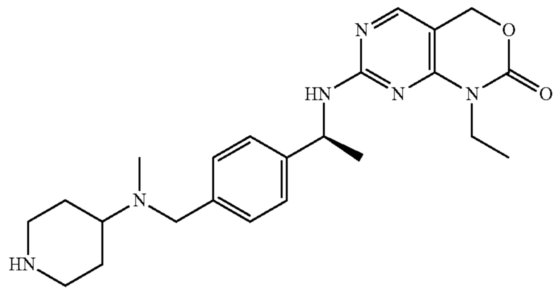 [SMILES: CCN1C(=O)OCc2cnc(N[C@@H](C)c3ccc(CN(C)C4CCNCC4)cc3)nc21] | 425 |
| 61 | 7-[[(1S)-1-[4-(Azetidin-3-yloxymethyl)phenyl]ethyl]amino]-1-isobutyl-4H-pyrimido[4,5-d][1,3]oxazin-2-one | 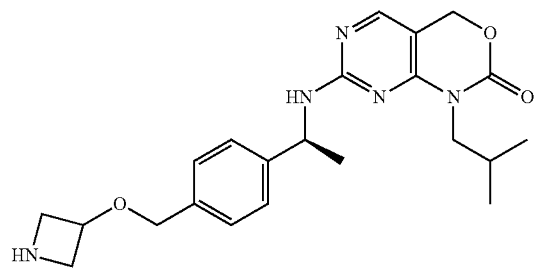 [SMILES: CC(C)CN1C(=O)OCc2cnc(N[C@@H](C)c3ccc(COC4CNC4)cc3)nc21] | 412 |
| 62 | 7-[[(1S)-1-[4-(2,6-Diazaspiro[3.3]heptan-2-ylmethyl)phenyl]ethyl]amino]-1-ethyl-4H-pyrimido[4,5-d][1,3]oxazin-2-one | 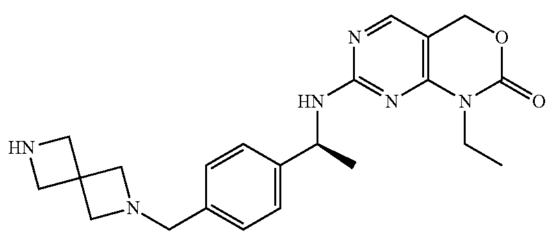 [SMILES: CCN1C(=O)OCc2cnc(N[C@@H](C)c3ccc(CN4CC5(CNC5)C4)cc3)nc21] | 409 |
| 63 | 7-[[(1S)-1-[4-(2,6-Diazaspiro[3.3]heptan-2-ylmethyl)phenyl]ethyl]amino]-1-isopropyl-4H-pyrimido[4,5-d][1,3]oxazin-2-one | 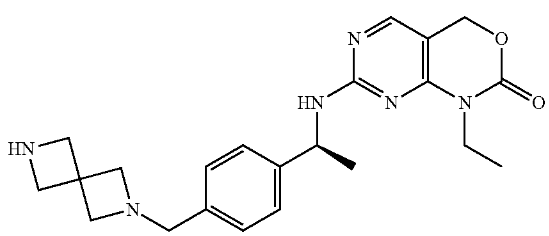 [SMILES: CCN1C(=O)OCc2cnc(N[C@@H](C)c3ccc(CN4CC5(CNC5)C4)cc3)nc21] | 423 |
| 64 | 1-Ethyl-7-[[(1S)-1-[3-fluoro-4-(piperazin-1-ylmethyl)phenyl]ethyl]amino]-4H-pyrimido[4,5-d][1,3]oxazin-2-one | 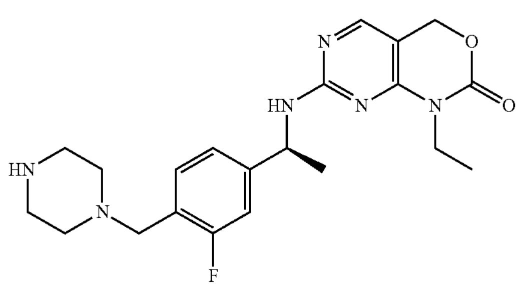 [SMILES: CCN1C(=O)OCc2cnc(N[C@@H](C)c3ccc(CN4CCNCC4)c(F)c3)nc21] | 415 |

TABLE 11-continued

| Prep. No. | Chemical name | ES/MS (m/z) (M + H) |
|---|---|---|
| 65 | 7-[[(1S)-1-[4-[2-(Azetidin-3-yl)ethynyl]phenyl]ethyl]amino]-1-ethyl-4H-pyrimido[4,5-d][1,3]oxazin-2-one | 378 |
| 66 | 7-[[(1S)-1-[4-(Azetidin-3-ylmethoxy)phenyl]ethyl]amino]-1-ethyl-4H-pyrimido[4,5-d][1,3]oxazin-2-one | 384 |
| 67 | 1-Ethyl-7-[[(1S)-1-(4-piperazin-1-ylphenyl)ethyl]amino]-4H-pyrimido[4,5-d][1,3]oxazin-2-one | 393 |
| 68 | 1-Methyl-7-[[(1S)-1-[4-(piperazin-1-ylmethyl)phenyl]ethyl]amino]-4H-pyrimido[4,5-d][1,3]oxazin-2-one | 383 |
| 69 | 1-(2,2-Difluoroethyl)-7-[[(1S)-1-[4-(piperazin-1-ylmethyl)phenyl]ethyl]amino]-4H-pyrimido[4,5-d][1,3]oxazin-2-one | 433 |
| 70 | 1-(2-Fluoroethyl)-7-[[(1S)-1-[4-(piperazin-1-ylmethyl)phenyl]ethyl]amino]-4H-pyrimido[4,5-d][1,3]oxazin-2-one | 415 |

TABLE 11-continued

| Prep. No. | Chemical name | Structure | ES/MS (m/z) (M + H) |
|---|---|---|---|
| 71 | 7-[[(1S)-1-[4-(2,5-dihydro-1H-pyrrol-3-ylmethoxy)phenyl]ethyl]amino]-1-ethyl-4H-pyrimido[4,5-d][1,3]oxazin-2-one | 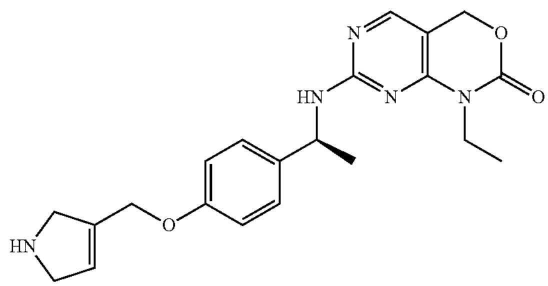 [SMILES: CCN1C(=O)OCc2cnc(N[C@@H](C)c3ccc(OCC4=CCNC4)cc3)nc21] | 396 |

Preparation 72

7-[[(1S)-1-[4-(Chloromethyl)phenyl]ethyl]amino]-1-isobutyl-4H-pyrimido[4,5-d][1,3]oxazin-2-one

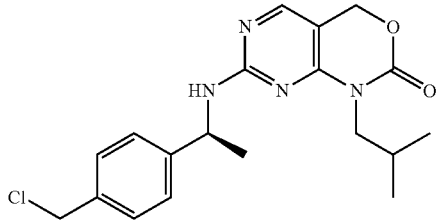 [SMILES: CC(C)CN1C(=O)OCc2cnc(N[C@@H](C)c3ccc(CCl)cc3)nc21]

Scheme 3, Step Q: $SOCl_2$ (2.1 mL, 4.2 mmol) is added by syringe to a suspension of $K_2CO_3$ (776 mg, 5.61 mmol) and 7-[[(1S)-1-[4-(hydroxymethyl)phenyl]ethyl]amino]-1-isobutyl-4H-pyrimido[4,5-d][1,3]oxazin-2-one (500 mg, 1.40 mmol) in $CH_2Cl_2$ (14 mL). After 5 hours the solvent is removed by vacuum providing the crude benzylic chloride as a co-mixture with $K_2CO_3$ (100% yield assumed). This mixture is carried on without further purification. MS (m/z): 375 (M+H).

The following compounds are prepared essentially by the method of Preparation 72.

TABLE 12

| Prep. No. | Chemical name | Structure | ES/MS (m/z) (M + H) |
|---|---|---|---|
| 73 | 7-[[(1S)-1-[4-(Chloromethyl)phenyl]ethyl]amino]-1-isopropyl-4H-pyrimido[4,5-d][1,3]oxazin-2-one | 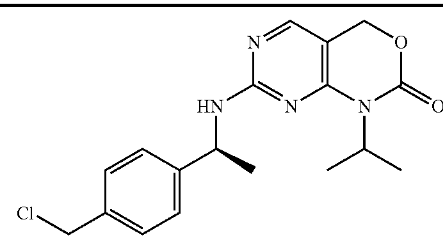 | ($^{35}Cl/^{37}Cl$) 361/363 |
| 74 | 7-[[(1S)-1-[4-(Chloromethyl)-3-fluoro-phenyl]ethyl]amino]-1-ethyl-4H-pyrimido[4,5-d][1,3]oxazin-2-one | 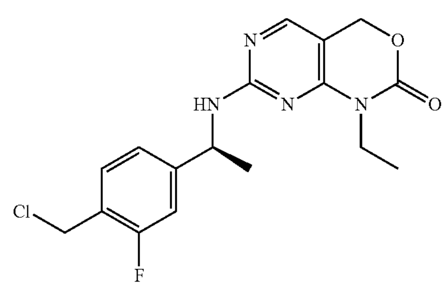 [SMILES: CCN1C(=O)OCc2cnc(N[C@@H](C)c3ccc(CCl)c(F)c3)nc21] | 365 |

Preparation 75 tert-Butyl 6-[[4-[(1S)-1-[(1-isobutyl-2-oxo-4H-pyrimido[4,5-d][1,3]oxazin-7-yl)amino]ethyl]phenyl]methyl]-2,6-diazaspiro[3.3]heptane-2-carboxylate

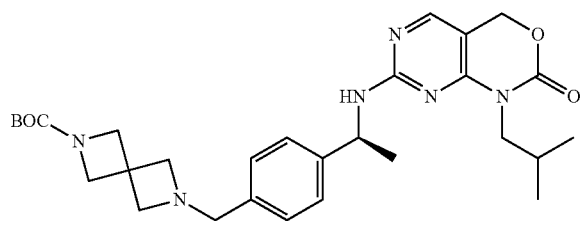 [SMILES: CC(C)CN1C(=O)OCc2cnc(N[C@@H](C)c3ccc(CN4CC5(C4)CN(C(=O)OC(C)(C)C)C5)cc3)nc21]

Scheme 3, Step Q: 7-[[(1S)-1-[4-(Chloromethyl)phenyl]ethyl]amino]-1-isobutyl-4H-pyrimido[4,5-d][1,3]oxazin-2-one (520 mg, 1.4 mmol), $K_2CO_3$ (580 mg, 4.2 mmol), and tert-butyl 2,6-diazaspiro[3.3]heptane-2-carboxylate oxalate salt (550 mg, 1.8 mmol) are suspended in ACN (7 mL) and are heated to 50° C. for 16 hours and then to 70° C. for 2 hours. Sodium iodide (210 mg, 1.4 mmol) is added and the reaction is heated at 70° C. for 2 hours and then at reflux for 3 hours. The mixture is cooled to room temperature and the solvent is evaporated. The resulting residue is taken up in $CH_2Cl_2$ and is washed with saturated aqueous $NaHCO_3$. The aqueous layer is extracted with $CH_2Cl_2$(3×). The combined organic extracts are washed with brine, dried ($Na_2SO_4$), filtered, and concentrated to provide the crude product as a yellow solid. The crude product is carried on to the next step without further purification (100% yield assumed). MS (m/z): 537 (M+H).

The following compounds are prepared essentially by the method of Preparation 75.

TABLE 13

| Prep. No. | Chemical name | Structure | ES/MS (m/z) (M + H) |
|---|---|---|---|
| 76 | tert-Butyl 2-[[4-[(1S)-1-[(1-isopropyl-2-oxo-4H-pyrimido[4,5-d][1,3]oxazin-7-yl)amino]ethyl]phenyl]methyl]-2,7-diazaspiro[3.5]nonane-7-carboxylate | 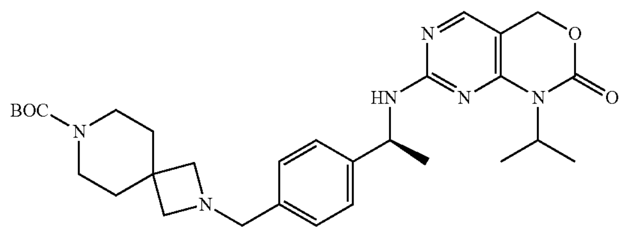 [SMILES: CC(C)N1C(=O)OCc2cnc(N[C@@H](C)c3ccc(CN4CC5(CCN(C(=O)OC(C)(C)C)CC5)C4)cc3)nc21] | 551 |
| 77 | tert-Butyl 4-[[4-[(1S)-1-[(1-ethyl-2-oxo-4H-pyrimido[4,5-d][1,3]oxazin-7-yl)amino]ethyl]phenyl]methyl-methyl-amino]piperidine-1-carboxylate | 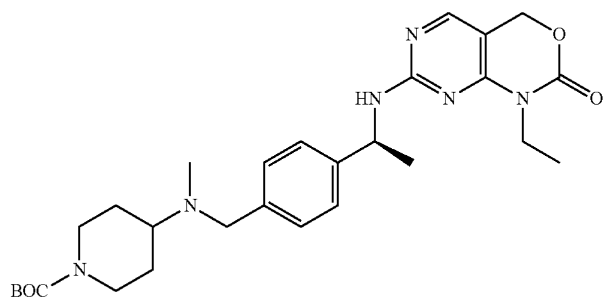 [SMILES: CCN1C(=O)OCc2cnc(N[C@@H](C)c3ccc(CN(C)C4CCN(C(=O)OC(C)(C)C)CC4)cc3)nc21] | 525 |
| 78 | Allyl 4-[[4-[(1S)-1-[(1-ethyl-2-oxo-4H-pyrimido[4,5-d][1,3]oxazin-7-yl)amino]ethyl]-2-fluorophenyl]methyl]piperazine-1-carboxylate | 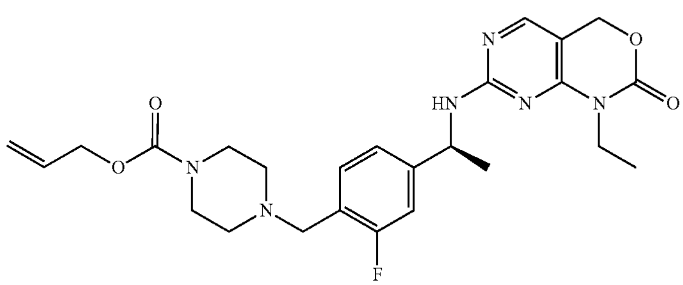 [SMILES: C=CCOC(=O)N1CCN(Cc2ccc([C@H](C)Nc3ncc4c(n3)N(CC)C(=O)OC4)cc2F)CC1] | 499 |

Preparation 79 tert-Butyl 4-[4-[(1S)-1-[(1-isopropyl-2-oxo-4H-pyrimido[4,5-d][1,3]oxazin-7-yl)amino]ethyl]phenyl]piperazine-1-carboxylate

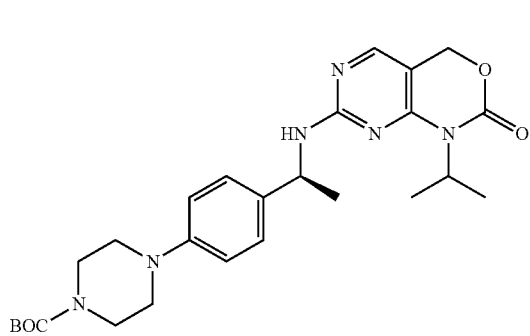 [SMILES: CC(C)N1C(=O)OCc2cnc(N[C@@H](C)c3ccc(N4CCN(C(=O)OC(C)(C)C)CC4)cc3)nc21]

Scheme 3, Step P: 7-[[(1S)-1-(4-Bromophenyl)ethyl]amino]-1-isopropyl-4H-pyrimido[4,5-d][1,3]oxazin-2-one (600 mg, 1.53 mmol), tert-butyl 3-(hydroxymethyl)azetidine-1-carboxylate (400 mg, 2.1 mmol), CuBr (100 mg, 0.70 mmol), $K_2CO_3$ (450 mg, 3.2 mmol), and L-hydroxyproline (500 mg, 4 mmol) are dissolved in DMSO (15 mL) and heated at 80° C. overnight. The reaction mixture is cooled to room temperature and is poured over water, extracted into EtOAc, and concentrated. The crude product is purified by chromatography (50% EtOAc/hexanes) to give the title compound as a tan foam (761 mg, 46%). MS (m/z): 497 (M+H).

The following compound is prepared essentially by the method of Preparation 79.

Preparation 81 tert-Butyl 3-ethynylazetidine-1-carboxylate

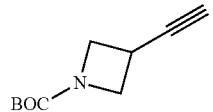

Sodium azide (2.4 g, 37 mmol) is suspended in ACN (14 mL) and methanesulfonyl chloride (2.7 mL, 35 mmol) is added over 45 seconds. The resulting mixture is stirred overnight at room temperature and is then cooled to 0° C., at which point dimethyl (2-oxopropyl)phosphonate (4.3 mL, 31 mmol) is added over 30 seconds followed by $Cs_2CO_3$ (11 g, 34 mmol). This mixture is stirred for 30 minutes at 0° C. and then at room temperature for 2.5 hours. The mixture is recooled to 0° C. and MeOH (15.5 mL) is added. After 1 hour, tert-butyl 3-formylazetidine-1-carboxylate (3.0 g, 16 mmol) is added followed by additional $Cs_2CO_3$ (9.1 g, 28 mmol), and 25 minutes later the ice-water bath is removed and the reaction is stirred overnight. The solvent is removed under vacuum to give an orange oil that is purified by silica gel chromatography using 50% MTBE/hexanes. The title compound is obtained as a light yellow oil (2.68 g, 93%). MS (m/z): 181 (M+H).

TABLE 14

| Prep. No. | Chemical name | Structure | ES/MS (m/z) (M + H) |
|---|---|---|---|
| 80 | tert-Butyl 4-[4-[(1S)-1-[(1-ethyl-2-oxo-4H-pyrimido[4,5-d][1,3]oxazin-7-yl)amino]ethyl]phenyl]piperazine-1-carboxylate | 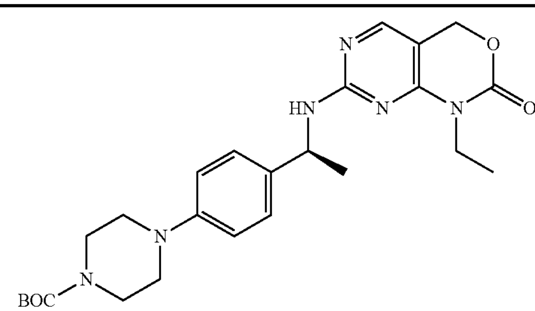 | 393 |

Preparation 82 tert-Butyl 3-[2-[4-[(1S)-1-[(1-ethyl-2-oxo-4H-pyrimido[4,5-d][1,3]oxazin-7-yl)amino]ethyl]phenyl]ethynyl]azetidine-1-carboxylate

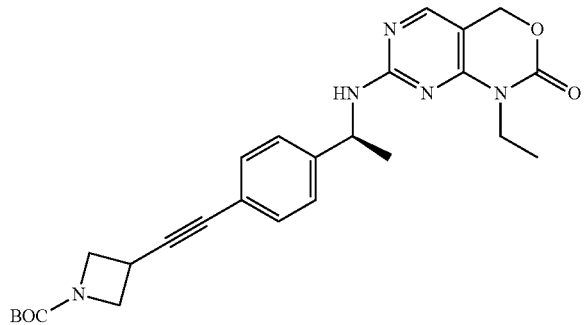 [SMILES: CCN1C(=O)OCc2cnc(N[C@@H](C)c3ccc(C#CC4CN(C(=O)OC(C)(C)C)C4)cc3)nc21]

Scheme 3, Step P: Nitrogen is bubbled through a solution of 7-[[(1S)-1-(4-bromophenyl)ethyl]amino]-1-ethyl-4H-pyrimido[4,5-d][1,3]oxazin-2-one (1.8 g, 4.77 mmol) and TEA (9.98 mL, 71.6 mmol) in THF (24 mL) for 5 minutes. Tetrakis(triphenylphosphine)palladium(0) (455 mg, 0.382 mmol, 8 mol %) and CuI (18 mg, 0.095 mmol, 2 mol %) are added and degassing is continued for an additional 5 minutes. tert-Butyl 3-ethynylazetidine-1-carboxylate (1.26 g, 6.68 mmol) is added and degassing is repeated for 20 seconds. The reaction is heated to 60° C. and stirred for ~24 hours, and then the heat is removed and stirring continued for an additional 24 hours. The mixture is diluted with water, extracted with CH$_2$Cl$_2$ (3×), dried (MgSO$_4$), filtered, and concentrated to give the crude product that is purified by silica gel chromatography eluting with 25-85% EtOAc/hexanes to give a yellow foam (1.14 g, 50%). MS (m/z): 478 (M+H).

Preparation 83 tert-Butyl 3-[2-[4-[(1S)-1-[(1-ethyl-2-oxo-4H-pyrimido[4,5-d][1,3]oxazin-7-yl)amino]ethyl]phenyl]ethyl]azetidine-1-carboxylate

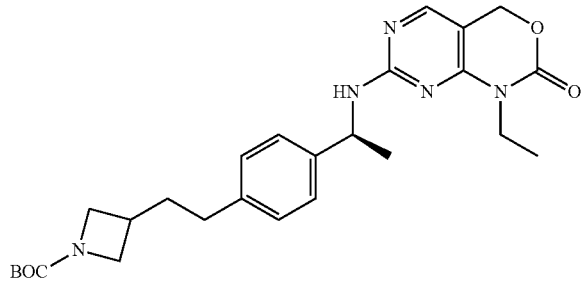

Scheme 3, Step P: tert-Butyl 3-[2-[4-[(1S)-1-[(1-ethyl-2-oxo-4H-pyrimido[4,5-d][1,3]oxazin-7-yl)amino]ethyl]phenyl]ethynyl]azetidine-1-carboxylate (1.14 g, 2.39 mmol) and Pd/CaCO$_3$ (1.67 mg, 10 wt % Pd, 0.157 mmol) are stirred in THF (24 mL) under an atmosphere of hydrogen over 17 hours. The reaction mixture is filtered over diatomaceous earth and the solids are washed with hot EtOAc/ MeOH. The crude product is chromatographed over silica gel eluting with 25-100% EtOAc/hexanes to give the title product as a light yellow foam (890 mg, 77%). MS (m/z): 482 (M+H).

Preparation 84

Benzyl N-[(1S)-1-(4-hydroxyphenyl)ethyl]carbamate

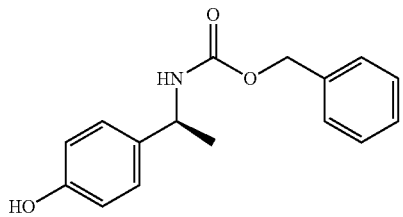 [SMILES: C[C@H](NC(=O)OCc1ccccc1)c1ccc(O)cc1]

Scheme 4: Benzyl chloroformate (3.20 mL, 20.6 mmol) is added dropwise to a mixture of (S)-4-(1-aminoethyl)phenol (2.75 g, 19.6 mmol) and NaHCO$_3$ (2.06 g, 24.6 mmol) in a mixture of THF (20 mL) and water (20 mL) at 0° C. The ice-water bath is removed after 30 minutes and the reaction mixture is stirred at room temperature for 72 hours. The mixture is diluted with EtOAc and the organic phase is separated, washed with 0.1 N aqueous HCl and brine. The organic phase is dried (Na$_2$SO$_4$), filtered, and concentrated and the resulting crude material is purified over silica gel (0 to 50% EtOAc/hexanes) to give the title product as a white solid (3.84 g, 71%). MS (m/z): 272 (M+H).

Preparation 85 tert-Butyl 3-[[4-[(1S)-1-(benzyloxycarbonylamino)ethyl]phenoxy]-methyl]azetidine-1-carboxylate

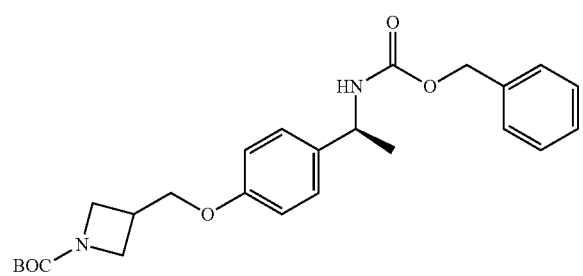 [SMILES: C[C@H](NC(=O)OCc1ccccc1)c1ccc(OCC2CN(C(=O)OC(C)(C)C)C2)cc1]

Scheme 4, Step R: At 0° C., DIAD (980 mL, 5 mmol) is added dropwise over 15 minutes to a solution of tert-butyl 3-(hydroxymethyl)azetidine-1-carboxylate (750 mg, 4 mmol), PPh$_3$ (1.3 g, 5 mmol), and benzyl N-[(1S)-1-(4-hydroxyphenyl)ethyl]carbamate (1.4 g, 1.25 mmol) in THF (16 mL). After the addition is complete the ice-water bath is removed and the reaction is stirred for 4.5 hours at room temperature. The reaction is then diluted with EtOAc, washed with water, 0.5 N aqueous NaOH, and brine, dried (Na$_2$SO$_4$), filtered, and concentrated. The product is purified over silica gel eluting with 0 to 50% EtOAc/hexanes to give the product contaminated with 24% starting phenol. The

Preparation 86 tert-Butyl 3-[[4-[(1S)-1-aminoethyl]phenoxy]methyl]azetidine-1-carboxylate

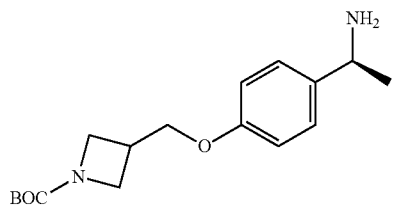 [SMILES: C[C@H](N)c1ccc(OCC2CN(C(=O)OC(C)(C)C)C2)cc1]

Scheme 4, Step M, Substep 1: tert-Butyl 3-[[4-[(1S)-1-(benzyloxycarbonylamino)ethyl]phenoxy]-methyl]azetidine-1-carboxylate (1.12 g, 2.54 mmol) and 10% Pd/C (335 mg, 0.315 mmol) are stirred in EtOH (60 mL) under hydrogen (138 kPa) for 45 minutes. The reaction mixture is filtered and concentrated to provide an oil that is carried on without further purification (100% yield assumed). MS (m/z): 290 (M−NH$_2$).

Preparation 87 tert-Butyl 3-[[4-[(1S)-1-[(1-ethyl-2-oxo-4H-pyrimido[4,5-d][1,3]oxazin-7-yl)amino]ethyl]phenoxy]methyl]-2,5-dihydropyrrole-1-carboxylate

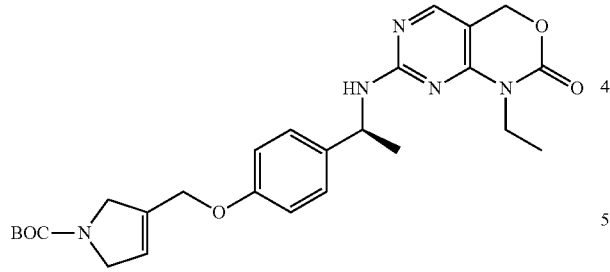

Scheme 3, Step P: A solution of 1-ethyl-7-[[(1S)-1-(4-hydroxyphenyl)ethyl]amino]-4H-pyrimido[4,5-d][1,3]oxazin-2-one (0.330 g, 1.05 mmol), tert-butyl 3-(chloromethyl)-2,5-dihydropyrrole-1-carboxylate (200 mg, 0.9 mmol), and K$_2$CO$_3$ (400 mg, 3 mmol) in acetone (7 mL) is heated at 60° C. in a sealed tube for 16 h and then is allowed to stir at room temperature for 72 h. The solution is diluted with water and extracted twice with DCM. The combined organic layers are dried (Na$_2$SO$_4$), filtered, and concentrated under vacuum. The crude product is purified by reverse phase chromatography (0 to 100% CH$_3$CN/water) to afford the title compound as an orange solid (250 mg, 0.504 mmol, 48%). MS (m/z): 496 (M+H).

above protocol is repeated on this mixture to give the desired product as an oil (1.12 g, 64%). MS (m/z): 341 (M-BOC+H), 463 (M+Na).

Preparation 88 tert-Butyl 6-[[4-[(1S)-1-[(1-isopropyl-2-oxo-4H-pyrimido[4,5-d][1,3]oxazin-7-yl)amino]ethyl]phenyl]methyl]-2,6-diazaspiro[3.3]heptane-2-carbxoylate

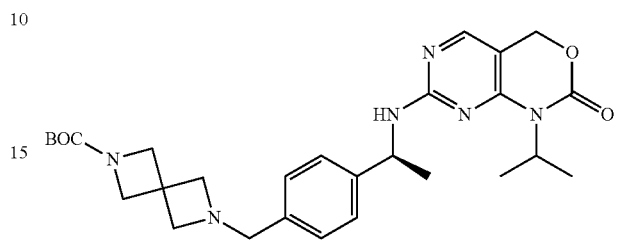

Scheme 3, Step P: DIPEA (0.75 mL, 4.3 mmol) is added to a solution of 7-[[(1S)-1-[4-(chloromethyl)phenyl]ethyl]amino]-1-isopropyl-4H-pyrimido[4,5-d][1,3]oxazin-2-one (1 g, 2.8 mmol) and tert-butyl 2,6-diazaspiro[3.3]heptane-2-carboxylate (820 mg, 4.1 mmol) in DMSO (14 mL) and the resulting mixture is heated at 50° C. for 16 hours and then is stirred at room temperature for 72 hours. The mixture is poured over water and is extracted with EtOAc, dried (MgSO$_4$), filtered, and concentrated. The crude product is purified over silica gel (5-7% 7 N NH$_3$ in MeOH/CH$_2$Cl$_2$) to give the title compound (978 mg, 68%). MS (m/z): 523 (M+H).

EXAMPLE 1

1-Isopropyl-7-[[(1S)-1-[4-[(4-prop-2-enoylpiperazin-1-yl)methyl]phenyl]ethyl]amino]-4H-pyrimido[4,5-d][1,3]oxazin-2-one

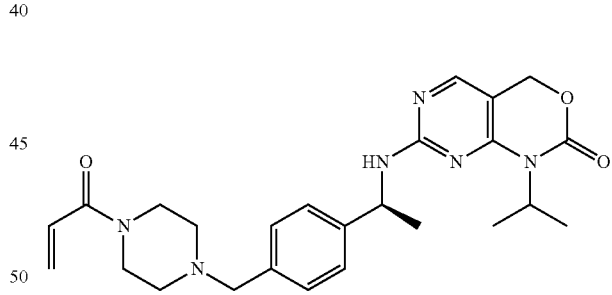

Scheme 2, Step N: To a solution of 1-isopropyl-7-[[(1S)-1-[4-(piperazin-1-ylmethyl)phenyl]ethyl]amino]-4H-pyrimido[4,5-d][1,3]oxazin-2-one hydrochloride (59.6 g, 113 mmol) and TEA (47.5 mL, 341 mmol) in CH$_2$Cl$_2$ (1.13 L) is added acryloyl chloride (11.1 mL in 80 mL CH$_2$Cl$_2$, 136 mmol) at −75° C. over 15 minutes. The reaction temperature is maintained below −70° C. during this addition. After 30 minutes, the reaction is quenched with saturated aqueous NaHCO$_3$ (100 mL) and the mixture is allowed to warm to ambient temperature. Water (200 mL) is added and the mixture is extracted with CH$_2$Cl$_2$ (3×), dried (Na$_2$SO$_4$), filtered, and concentrated to yield a yellow foam. The crude product is purified by silica gel chromatography (6 to 10%/[10% MeOH/CH$_2$Cl$_2$]/EtOAc) to give the title product as a white foam (42.5 g, 81%). MS (m/z): 465 (M+H).

EXAMPLE 2

1-Ethyl-7-[[(1S)-1-[4-[(4-prop-2-enoylpiperazin-1-yl)methyl]phenyl]ethyl]amino]-4H-pyrimido[4,5-d][1,3]oxazin-2-one

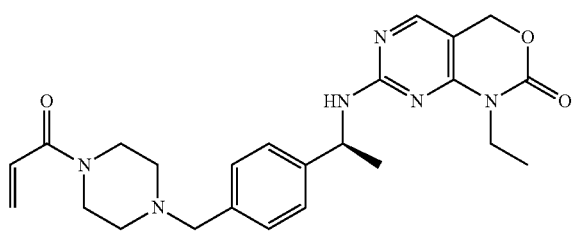 [SMILES: C=CC(=O)N1CCN(Cc2ccc([C@H](C)Nc3ncc4c(n3)N(CC)C(=O)OC4)cc2)CC1]

Scheme 2, Step N: To a solution of 1-ethyl-7-[[(1S)-1-[4-(piperazin-1-ylmethyl)phenyl]ethyl]amino]-4H-pyrimido[4,5-d][1,3]oxazin-2-one hydrochloride (53.6 g, 124 mmol) and TEA (52 mL, 373 mmol) in $CH_2Cl_2$ (1.2 L) is added acryloyl chloride (12.1 mL in 80 mL $CH_2Cl_2$, 149 mmol) at −75° C. over 15 minutes. The reaction temperature is maintained below −70° C. during this addition. After 1 hour the reaction is quenched with saturated aqueous $NaHCO_3$ (100 mL) and the subsequent mixture is allowed to warm to ambient temperature. Water (200 mL) is added and the mixture is extracted with $CH_2Cl_2$ (3×), dried ($Na_2SO_4$), filtered, and concentrated to give a yellow foam. The crude product is purified by silica gel chromatography (6 to 10% [10% $MeOH/CH_2Cl_2$]/EtOAc) to give the title product as a light yellow foam (30.2 g, 54%). MS (m/z): 451 (M+H).

The following Examples are prepared essentially by the method of Example 2.

TABLE 15

| Ex. No. | Chemical name | Structure | ES/MS (m/z) (M + H) |
|---|---|---|---|
| 3 | 1-Isobutyl-7-[[(1S)-1-[4-[(4-prop-2-enoylpiperazin-1-yl)methyl]phenyl]ethyl]amino]-4H-pyrimido[4,5-d][1,3]oxazin-2-one | 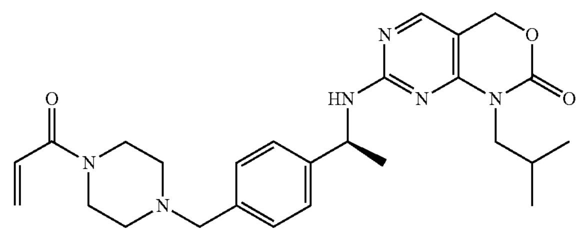 [SMILES: C=CC(=O)N1CCN(Cc2ccc([C@H](C)Nc3ncc4c(n3)N(CC(C)C)C(=O)OC4)cc2)CC1] | 479 |
| 4 | 1-Ethyl-7-[[(1S)-1-[4-[(1-prop-2-enoylazetidin-3-yl)oxymethyl]phenyl]ethyl]amino]-4H-pyrimido[4,5-d][1,3]oxazin-2-one | 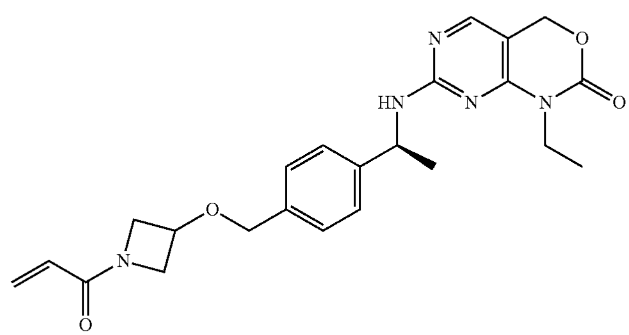 | 438 |
| 5 | 1-Isobutyl-7-[[(1S)-1-[4-[(2-prop-2-enoyl-2,6-diazaspiro[3.3]heptan-6-yl)methyl]phenyl]ethyl]amino]-4H-pyrimido[4,5-d][1,3]oxazin-2-one | 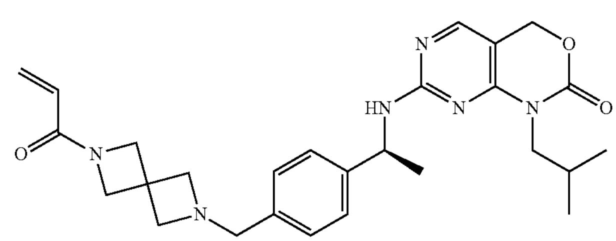 [SMILES: C=CC(=O)N1CC2(CN(Cc3ccc([C@H](C)Nc4ncc5c(n4)N(CC(C)C)C(=O)OC5)cc3)C2)C1] | 491 |

TABLE 15-continued

| Ex. No. | Chemical name | Structure | ES/MS (m/z) (M + H) |
|---|---|---|---|
| 6 | 1-Isopropyl-7-[[(1S)-1-[4-(4-prop-2-enoylpiperazin-1-yl)phenyl]ethyl]amino]-4H-pyrimido[4,5-d][1,3]oxazin-2-one | 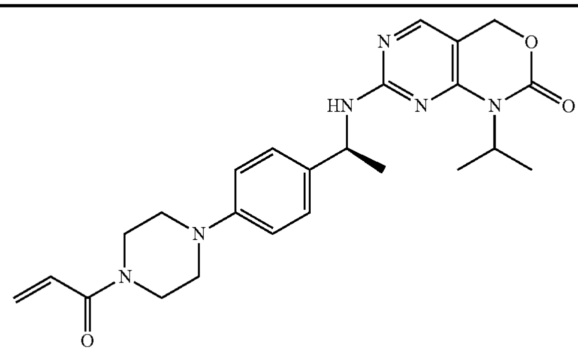 | 451 |
| 7 | 1-Ethyl-7-[[(1S)-1-[4-[2-(1-prop-2-enoylazetidin-3-yl)ethyl]phenyl]ethyl]amino]-4H-pyrimido[4,5-d][1,3]oxazin-2-one | 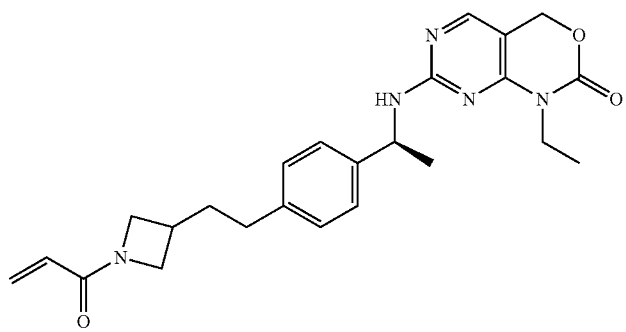 | 436 |
| 8 | 1-Isopropyl-7-[[(1S)-1-[4-[(7-prop-2-enoyl-2,7-diazaspiro[3.5]nonan-2-yl)methyl]phenyl]ethyl]amino]-4H-pyrimido[4,5-d][1,3]oxazin-2-one | 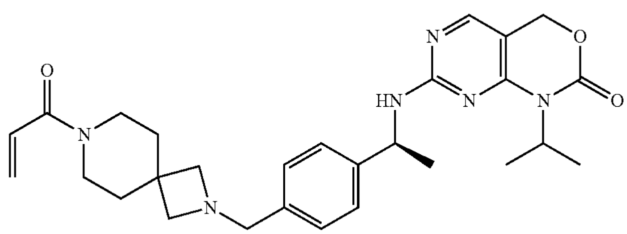 [SMILES: C=CC(=O)N1CCC2(CC1)CN(Cc1ccc([C@H](C)Nc3ncc4c(n3)N(C(C)C)C(=O)OC4)cc1)C2] | 505 |
| 9 | 1-Isopropyl-7-[[(1S)-1-[4-[(1-prop-2-enoylazetidin-3-yl)methoxy]-phenyl]ethyl]amino]-4H-pyrimido[4,5-d][1,3]oxazin-2-one | 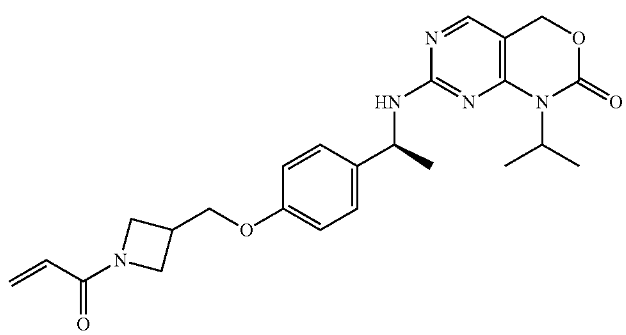 [SMILES: C=CC(=O)N1CC(COc2ccc([C@H](C)Nc3ncc4c(n3)N(C(C)C)C(=O)OC4)cc2)C1] | 452 |
| 10 | 1-Ethyl-7-[[(1S)-1-[4-[[methyl-(1-prop-2-enoylazetidin-3-yl)amino]methyl]-phenyl]ethyl]amino]-4H-pyrimido[4,5-d][1,3]oxazin-2-one | 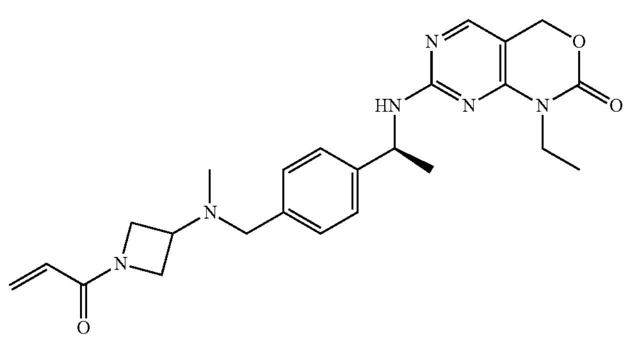 | 451 |

TABLE 15-continued

| Ex. No. | Chemical name | Structure | ES/MS (m/z) (M + H) |
|---|---|---|---|
| 11 | 1-[(1R)-2-Hydroxy-1-methyl-ethyl]-7-[[(1S)-1-[4-[(4-prop-2-enoylpiperazin-1-yl)methyl]phenyl]ethyl]amino]-4H-pyrimido[4,5-d][1,3]oxazin-2-one | 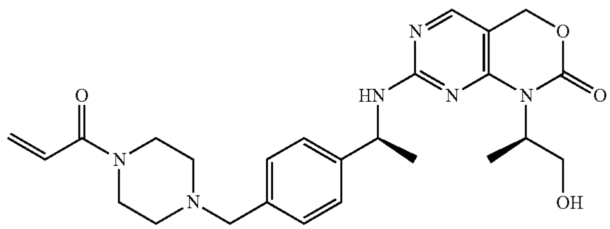 [SMILES: C=CC(=O)N1CCN(Cc2ccc([C@H](C)Nc3ncc4c(n3)N([C@H](C)CO)C(=O)OC4)cc2)CC1] | 481 |
| 12 | 1-Ethyl-7-[[(1S)-1-[4-[[methyl-(1-prop-2-enoyl-4-piperidyl)amino]-methyl]phenyl]ethyl]amino]-4H-pyrimido[4,5-d][1,3]oxazin-2-one | 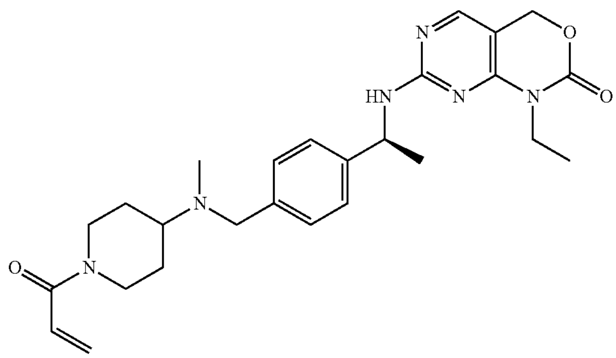 [SMILES: C=CC(=O)N1CCC(N(C)Cc2ccc([C@H](C)Nc3ncc4c(n3)N(CC)C(=O)OC4)cc2)CC1] | 479 |
| 13 | 1-Isobutyl-7-[[(1S)-1-[4-[(1-prop-2-enoylazetidin-3-yl)oxymethyl]phenyl]ethyl]amino]-4H-pyrimido[4,5-d][1,3]oxazin-2-one | 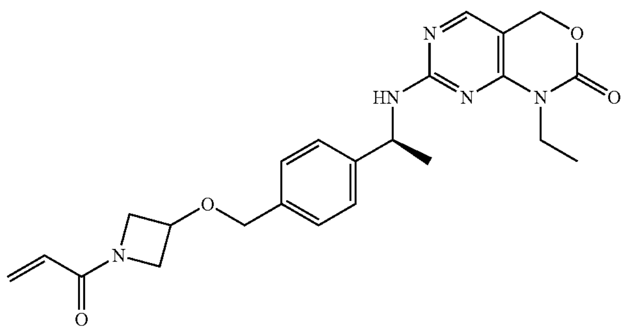 [SMILES: C=CC(=O)N1CC(OCc2ccc([C@H](C)Nc3ncc4c(n3)N(CC)C(=O)OC4)cc2)C1] | 466 |
| 14 | 1-Ethyl-7-[[(1S)-1-[4-[(2-prop-2-enoyl-2,6-diazaspiro[3.3]heptan-6-yl)methyl]phenyl]ethyl]amino]-4H-pyrimido[4,5-d][1,3]oxazin-2-one | 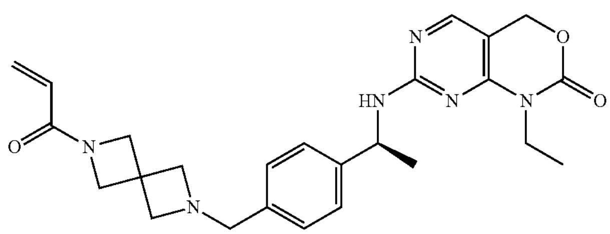 [SMILES: C=CC(=O)N1CC2(CN(Cc3ccc([C@H](C)Nc4ncc5c(n4)N(CC)C(=O)OC5)cc3)C2)C1] | 477 |
| 15 | 1-Isopropyl-7-[[(1S)-1-[4-[(2-prop-2-enoyl-2,6-diazaspiro[3.3]heptan-6-yl)methyl]phenyl]ethyl]amino]-4H-pyrimido[4,5-d][1,3]oxazin-2-one | 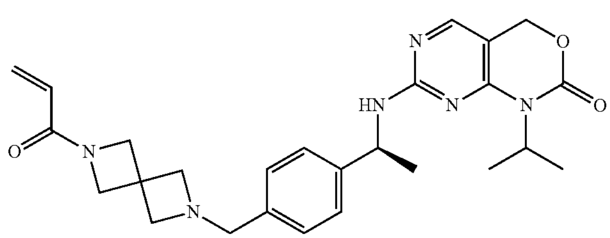 [SMILES: C=CC(=O)N1CC2(CN(Cc3ccc([C@H](C)Nc4ncc5c(n4)N(C(C)C)C(=O)OC5)cc3)C2)C1] | 477 |

TABLE 15-continued

| Ex. No. | Chemical name | Structure | ES/MS (m/z) (M + H) |
|---|---|---|---|
| 16 | 1-Ethyl-7-[[(1S)-1-[3-fluoro-4-[(4-prop-2-enoylpiperazin-1-yl)methyl]phenyl]ethyl]amino]-4H-pyrimido[4,5-d][1,3]oxazin-2-one | 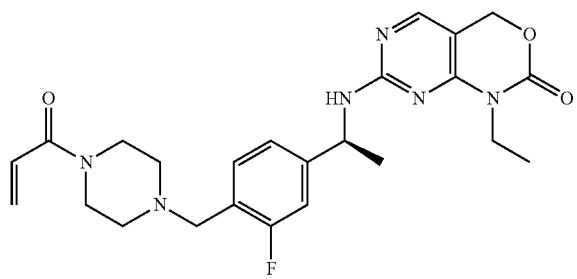 [SMILES: C=CC(=O)N1CCN(Cc2ccc([C@H](C)Nc3ncc4c(n3)N(CC)C(=O)OC4)cc2F)CC1] | 469 |
| 17 | 1-Ethyl-7-[[(1S)-1-[4-[(1-prop-2-enoylazetidin-3-yl)methoxy]phenyl]ethyl]amino]-4H-pyrimido[4,5-d][1,3]oxazin-2-one | 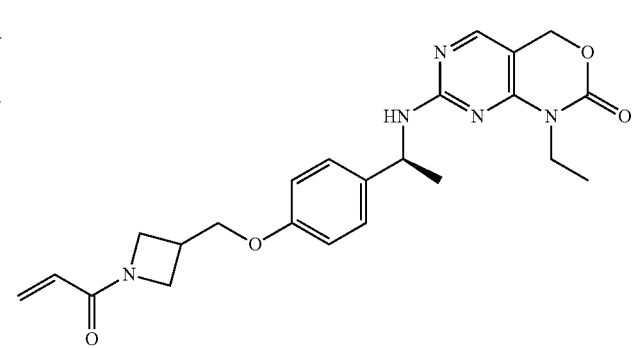 | 438 |
| 18 | 1-Ethyl-7-[[(1S)-1-[4-(4-prop-2-enoylpiperazin-1-yl)phenyl]ethyl]amino]-4H-pyrimido[4,5-d][1,3]oxazin-2-one | 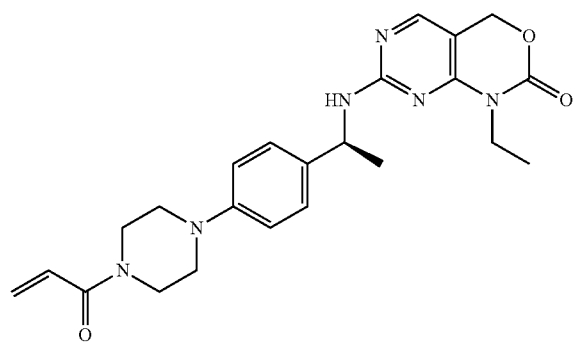 [SMILES: C=CC(=O)N1CCN(c2ccc([C@H](C)Nc3ncc4c(n3)N(CC)C(=O)OC4)cc2)CC1] | 437 |
| 19 | 1-Methyl-7-[[(1S)-1-[4-[(4-prop-2-enoylpiperazin-1-yl)methyl]phenyl]ethyl]amino]-4H-pyrimido[4,5-d][1,3]oxazin-2-one | 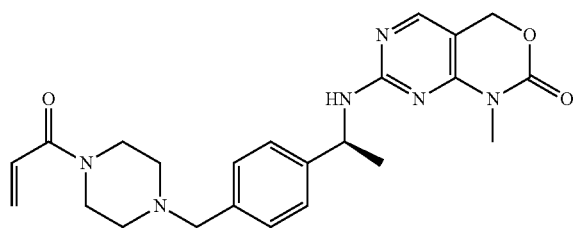 [SMILES: C=CC(=O)N1CCN(Cc2ccc([C@H](C)Nc3ncc4c(n3)N(C)C(=O)OC4)cc2)CC1] | 437 |
| 20 | 1-(2,2-difluoroethyl)-7-[[(1S)-1-[4-[(4-prop-2-enoylpiperazin-1-yl)methyl]phenyl]ethyl]amino]-4H-pyrimido[4,5-d][1,3]oxazin-2-one | 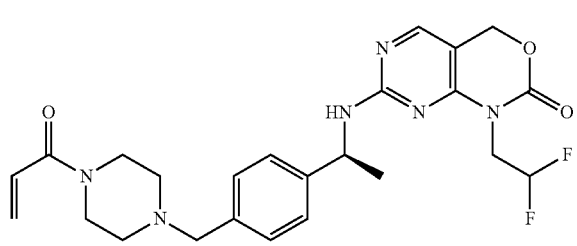 [SMILES: C=CC(=O)N1CCN(Cc2ccc([C@H](C)Nc3ncc4c(n3)N(CC(F)F)C(=O)OC4)cc2)CC1] | 461 |

TABLE 15-continued

| Ex. No. | Chemical name | Structure | ES/MS (m/z) (M + H) |
|---|---|---|---|
| 21 | 1-(2-fluoroethyl)-7-[[(1S)-1-[4-[(4-prop-2-enoylpiperazin-1-yl)methyl]phenyl]ethyl]amino]-4H-pyrimido[4,5-d][1,3]oxazin-2-one | 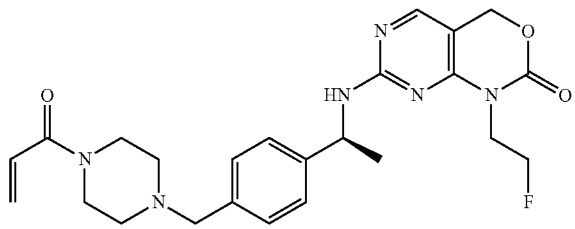 | 469 |
| 22 | 1-ethyl-7-[[(1S)-1-[4-[(1-prop-2-enoyl-2,5-dihydropyrrol-3-yl)methoxy]phenyl]ethyl]amino]-4H-pyrimido[4,5-d][1,3]oxazin-2-one | 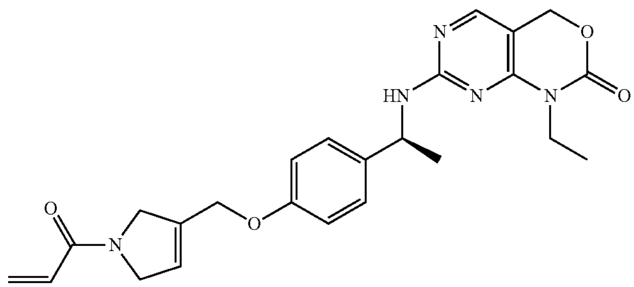 [SMILES: C=CC(=O)N1CC=C(COc2ccc([C@H](C)Nc3ncc4c(n3)N(CC)C(=O)OC4)cc2)C1] | 450 |

EXAMPLE 23

1-Ethyl-7-[[(1S)-1-[4-[(4-prop-2-enoylpiperazin-1-yl)methyl]phenyl]ethyl]amino]-4H-pyrimido[4,5-d][1,3]oxazin-2-one 4-hydroxybenzoic acid salt

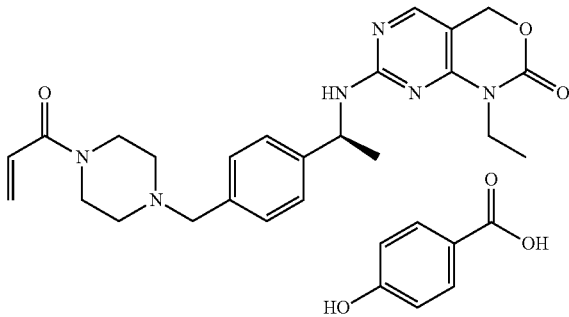

To a solution of 1-ethyl-7-[[(1S)-1-[4-(piperazin-1-ylmethyl)phenyl]ethyl]amino]-4H-pyrimido[4,5-d][1,3]oxazin-2-one (376 g, 758.6 mmol) in DCM (6700 mL) is added TEA (116 mL, 832 mmol). The mixture is cooled to less than −70° C. A solution of acryloyl chloride (64.8 mL, 796 mmol) in DCM (750 mL) is added at a temperature of less than −68° C. over 2 hours. After addition, the reaction is stirred at less than −68° C. 15 minutes. Water is added (1500 mL) and the solution is warmed to room temperature. The layers are separated. The organic layer is washed with water (2×1 L), 50% saturated NaHCO$_3$ (1 L) and brine (1 L), and dried over Na$_2$SO$_4$. This solution is added to a solution of 4-hydroxybenzoic acid (115 g, 832.61 mmol) in CPME (1800 mL). The resulting cloudy mixture is heated to 35-40° C. resulting in a yellow solution that is filtered through diatomaceous earth and is washed with a mixture of DCM and CPME (1:1). The filtrate and washes are combined and concentrated to ¼ volume. The resulting slurry is co-evaporated with heptane (2×1 L). and filtered, washed with heptane and dried under N$_2$ vacuum overnight to give the title compound (382.7 g, 81%). MS (m/z): 451 (M+H). The crude 1-ethyl-7-[[(1S)-1-[4-[(4-prop-2-enoylpiperazin-1-ium-1-yl)methyl]phenyl]ethyl]amino]-4H-pyrimido[4,5-d][1,3]oxazin-2-one; 4-hydroxybenzoate (624 g, 1060 mmol) is suspended in a pre-mixed solvents of acetone (9.4 L) and heptane (9.4 L) and the slurry is stirred at room temperature for 5 hours. The solid is filtered and washed with 1:1 heptane/acetone (3×500 mL). The filtrate and washes are evaporated. To the residue is added heptane (2 L) and filtered, and the collected solid is dried under vacuum at 50° C. to give the title compound as a light yellow solid (357 g, 55%).

Alternative Preparation Example 23

Crystalline 1-Ethyl-7-[[(1S)-1-[4-[(4-prop-2-enoylpiperazin-1-yl)methyl]phenyl]ethyl]amino]-4H-pyrimido[4,5-d][1,3]oxazin-2-one 4-hydroxybenzoic acid salt To a solution of 1-ethyl-7-[[(1S)-1-[4-[(4-prop-2-enoylpiperazin-1-yl)methyl]phenyl]ethyl]amino]-4H-pyrimido[4,5-d][1,3]oxazin-2-one (28.5 g, 63.3 mmol) in CPME (430 mL) at 60° C. under nitrogen is added 4-hydroxybenzoic acid (8.74 g, 63.3 mmol) dissolved in CPME (115 mL). After a few minutes stirring at 300 rpm at 60° C., the stirring is slowed to 50 rpm and the sample is stirred for 2 hours. At this time the temperature is raised to 45° C., and the sample is stirred at 200 rpm for 4 hours. The sample is then brought to room temperature. The walls of the flask are scraped to remove solid and the solid is collected by filtration and air dried to give the first crop. The filtrate is reduced under vacuum to approximately half volume and cooled while stirring in an ice bath to afford more solid. This solid is collected and added to the first crop. The product is dried in a 70° C. vacuum oven overnight to give the title compound (33.4 g, 56.7 mmol, 89.7%). MS (m/z): 451 (M+H).

X-Ray Powder Diffraction (XRD)

The XRD patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 400 in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of +0.2 in 2θ will take into account these potential variations without hindering the unequivocal identification of the indicated crystal form. Confirmation of a crystal form may be made based on any unique combination of distinguishing peaks (in units of °2θ), typically the more prominent peaks. The crystal form diffraction patterns, collected at ambient temperature and relative humidity, are adjusted based on NIST 675 standard peaks at 8.853 and 26.774 degrees 2-theta.

A prepared sample of Example 23 is characterized by an XRD pattern using CuKa radiation as having diffraction peaks (2-theta values) as described in Table 16 below, and in particular having peaks at 16.8 in combination with one or more of the peaks selected from the group consisting of 15.8, 13.9, and 13.4; with a tolerance for the diffraction angles of 0.2 degrees.

TABLE 16

XRD peaks of crystalline Example 23

| Peak | Angle (°2-Theta) +/− 0.2° | Relative Intensity (% of most intense peak) |
|---|---|---|
| 1 | 6.7 | 22.7% |
| 2 | 10.0 | 33.0% |
| 3 | 11.0 | 24.0% |
| 4 | 11.6 | 7.1% |
| 5 | 13.4 | 48.4% |
| 6 | 13.9 | 50.9% |
| 7 | 14.5 | 25.9% |
| 8 | 15.8 | 69.7% |
| 9 | 16.8 | 100.0% |
| 10 | 17.5 | 36.2% |

EXAMPLE 24

Crystalline 1-Ethyl-7-[[(1S)-1-[4-[(4-prop-2-enoylpiperazin-1-yl)methyl]phenyl]ethyl]amino]-4H-pyrimido[4,5-d][1,3]oxazin-2-one bis(2,5-dihydroxybenzoic acid) salt

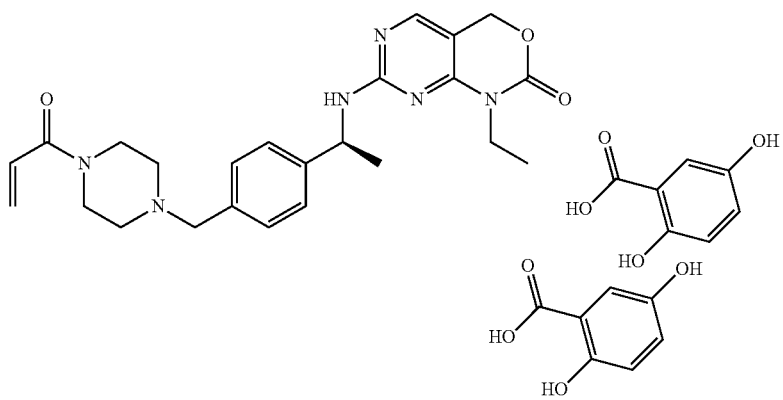

To a solution of 1-ethyl-7-[[(1S)-1-[4-[(4-prop-2-enoylpiperazin-1-yl)methyl]phenyl]ethyl]amino]-4H-pyrimido[4,5-d][1,3]oxazin-2-one (3.94 g, 8.73 mmol) in EtOH (7 mL) stirring at 1000 rpm at 48° C. is added 2,5-dihydoxybenzoic acid (350 mg, 17.8 mmol) dissolved in EtOH (8 mL) giving a dark yellow solution. The sample is allowed to cool to ambient temperature, and stirring is reduced to 300 rpm. A white solid results which is isolated by vacuum filtration. The vial is rinsed with EtOH (10 mL) which is added to the cake. The cake is dried in place under a nitrogen stream for 10 minutes, then overnight in an ambient vacuum oven (6.34 g, 8.35 mmol, 95.62%). MS (m/z): 451 (M+H).

A prepared sample of the Example 24 is characterized by an XRD pattern using CuKa radiation as having diffraction peaks (2-theta values) as described in Table 17 below, and in particular having peaks at 24.7 in combination with one or more of the peaks selected from the group consisting of 17.0, 24.0, and 19.8; with a tolerance for the diffraction angles of 0.2 degrees.

TABLE 17

XRD peaks of Example 24

| Peak | Angle (°2-Theta) +/− 0.2° | Relative Intensity (% of most intense peak) |
|---|---|---|
| 1 | 7.9 | 8.0% |
| 2 | 8.5 | 4.9% |
| 3 | 9.7 | 6.3% |
| 4 | 11.9 | 37.8% |
| 5 | 13.9 | 25.6% |
| 6 | 17.0 | 90.3% |
| 7 | 19.8 | 40.2% |
| 8 | 24.0 | 43.8% |
| 9 | 24.7 | 100.0% |
| 10 | 26.1 | 35.2% |

EXAMPLE 25

Crystalline 1-Ethyl-7-[[(1S)-1-[4-[(4-prop-2-enoylpiperazin-1-yl)methyl]phenyl]ethyl]amino]-4H-pyrimido[4,5-d][1,3]oxazin-2-one bis(saccharin) salt

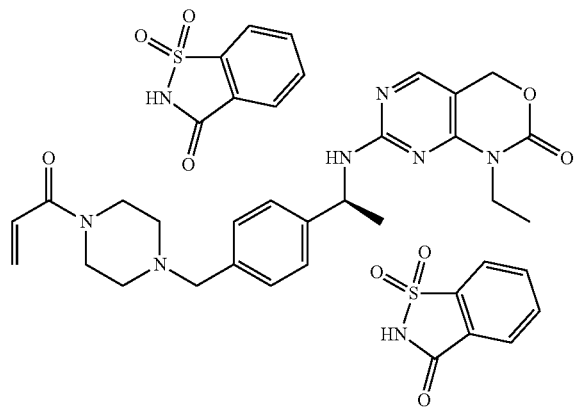

To a solution of 1-ethyl-7-[[(1S)-1-[4-[(4-prop-2-enoylpiperazin-1-yl)methyl]phenyl]ethyl]amino]-4H-pyrimido[4,5-d][1,3]oxazin-2-one (955 mg, 2.12 mmol) in EtOH (3 mL) stirring at 1000 rpm at 70° C. is added saccharin (862 mg, 4.66 mmol) in EtOH (7 mL) giving a white opaque slurry. A white gum is formed, and further EtOH (10 mL) is added. The sample is stirred for 30 minutes to convert the gum to a slurry of a white solid. The sample is brought to room temperature and the white solid is isolated by vacuum filtration (1.61 g, 1.97 mmol, 93.0%).

A prepared sample of Example 25 is characterized by an XRD pattern using CuKa radiation as having diffraction peaks (2-theta values) as described in Table 18 below, and in particular having peaks at 19.1 in combination with one or more of the peaks selected from the group consisting of 22.0, 16.8, and 23.7; with a tolerance for the diffraction angles of 0.2 degrees.

TABLE 18

XRD peaks of Example 25

| Peak | Angle (°2-Theta) ±/− 0.2° | Relative Intensity (% of most intense peak) |
|---|---|---|
| 1 | 9.5 | 42.2% |
| 2 | 10.4 | 17.1% |
| 3 | 11.4 | 22.2% |
| 4 | 14.5 | 54.3% |
| 5 | 16.8 | 66.5% |
| 6 | 18.1 | 50.8% |
| 7 | 19.1 | 100.0% |
| 8 | 22.0 | 90.0% |
| 9 | 23.7 | 59.5% |
| 10 | 26.6 | 35.9% |

Cancer is increasingly recognized as a heterogeneous collection of diseases whose initiation and progression are induced by the aberrant function of one or more genes that regulate DNA repair, genome stability, cell proliferation, cell death, adhesion, angiogenesis, invasion, and metastasis in cell and tissue microenvironments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

Extensive catalogues of the cytogenetic aberrations in human cancer have been compiled and are maintained and regularly updated online (see The Mitelman Database of Chromosome Aberrations in Cancer at the US National Cancer Institute (NCI) Cancer Genome Anatomy Project (CGAP) Web site). The Wellcome Trust Sanger Institute Cancer Genome Project maintains a detailed online "Cancer Gene Census" of all human genes that have been causally linked to tumorigenesis as well as the COSMIC (Catalogue of Somatic Mutations in Cancer) database of somatic mutations in human cancer. A further source containing abundant information on cytogenetic changes causally linked to various cancers is the Atlas of Genetics and Cytogenetics in Oncology and Haematology.

Diagnosis of cancerous malignancies by biopsy, immunophenotyping and other tests are known and routinely used. In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

Mutations in IDH1 have been identified in multiple cancer tumor types including, but not limited to, glioma, glioblastoma multiforme, astrocytomas, oligodendrogliomas, paraganglioma, myelodysplastic syndrome (MDS), B cell acute lymphoblastic leukemia (B-ALL), thyroid, colorectal, acute myeloid leukemia (AML), Dang et al., *Trends Mol. Med.,* 2010, 16: 387-397; Ward et al., *Oncogene,* 2012, 31(19): 2491-2498; melanoma, Shibata et al., *Am. J. Pathol.,* 2010, 178(3): 1395-1402; prostate, Flaherty et al., *J. Clin. Oncol.,* 2014, 32 (suppl. 4; Abstract 213); Cairns et al., *Cancer Discovery,* 2013, 3: 730-741; chondrosarcoma and cholangiocarcinoma, Balss et al., *Acta Neuropathol.,* 2012, 124: 883-891; Cairns et al., *Cancer Discovery,* 2013, 3: 730-741; angioimmunoblastic T-cell lymphoma (AITL), Cairns et al. *Blood,* 2012. 119(8):1901-1903. Mutations have been found at or near particular residues in the active site: G97D, R100, R132H, R132C, R132S, R132V, R132G, V711, R132L, and G123R for IDH1, Dang et al., *Trends Mol. Med.,* 2010, 16: 387-397; Ward et al., 2012 and Supplementary Table 2.

Mutant forms of IDH1 have been shown to have a neomorphic activity (gain of function) reducing α-ketoglutarate to 2-hydroxyglutarate. Endogenous production of 2-hydroxyglutarate is enantiospecific resulting in the generation of the D-enantiomer (also termed the (R) enantiomer. Normally, cells have low levels of 2-hydroxyglutarate while cells harboring IDH1 mutations evidence significantly elevated levels of 2-hydroxyglutarate. Significantly elevated levels of 2-hydroxyglutarate are detected in tumors harboring the mutations and in plasma of patients with mutant IDH1. High levels of 2-hydroxyglutarate are associated with a hypermethylation phenotype resulting in a block in differentiation that leads to enhanced tumorigenesis.

The activity of a specific irreversible covalent inhibitor is defined by its binding to the target (IDH1), defined by $K_I$, and the maximum potential rate of covalent bond formation, defined by $k_{inact}$. These two factors are not separate entities, but rather work together to produce the desired effect of covalent bond formation. This is illustrated by the following 3 points.

First, the fact that an electrophile for example, acrylamide, must be properly positioned relative to a nucleophile for example, cysteine, is a fundamental component of covalent bond formation in organic chemistry. There is a precise angle and distance at which the nucleophile must approach the electrophile to form the covalent bond. The simple placement of an electrophile near a nucleophile is not sufficient for covalent bond formation.

Second, when incorporating a reactive group on a core that contains hydrogen bonding moieties to stabilize the binding of the inhibitor to the enzyme for example, an orienting core, a skilled artisan must consider how the orienting core binds to the target and positions the electrophile relative to the nucleophile in light of the optimal angle and distance mentioned above. Again, the simple placement of an electrophile near a nucleophile is not sufficient for covalent bond formation. Changes in the orienting core may impact the ability of an inhibitor compound to form a covalent bond.

Third, when the above two points are considered together, the mere presence of an electrophile moiety on an orienting core is not sufficient to suggest a covalent bond will be formed.

The following in vitro and in vivo studies demonstrate the mutant IDH1 protein inhibitory activity and efficacy of the tested compounds of Formula I against various specific cancer cell lines. These assays are generally recognized by those skilled in the art as indicative of human clinical therapeutic activity. Inhibition of mutant IDH1 neomorphic proteins in the disclosed studies is believed will be effective against further mutant IDH1 neomorphic proteins. Assays evidencing mutant IDH1 inhibitory activity and efficacy may be carried out substantially as follows or by similar assays affording similar data.

The results of the following assays demonstrate that the compounds exemplified and tested are useful as IDH1 mutant inhibitors and may be useful in treating cancers expressing mutant IDH1.

Biochemical Assays for IDH1 and IDH2 Mutant Enzymes

IDH1-R132H, IDH1-R132C, IDH2-R172K and IDH2-R140Q mutant enzymes catalyze the conversion of αKG to 2HG. 2HG is analyzed using in-line solid phase extraction and mass spectrometry. This analysis is carried out in a RapidFire® instrument coupled to a 6460 triple quadrupole mass spectrometer (G6460A Agilent).

IDH1 mutant (R132H and R132C) and IDH2 mutant (R140Q and R172K) proteins containing N-terminal His-tag are expressed in *E. coli* and purified using nickel affinity chromatography. The enzyme assays are carried out in V-bottom 96 well polypropylene plates containing 100 mM Tris-HCl buffer, 1 mM DTT, 0.005% TRITON™ X-100, 120 mM NaCl. For IDH1 R132H, α-ketoglutarate, NADPH and $MnCl_2$ are included at final concentrations of 300 µM, 2.5 µM and 300 µM respectively. For IDH1 R132C, α-ketoglutarate, NADPH and $MnCl_2$ are included at final concentrations of 100 µM, 10 µM and 100 µM respectively. For IDH2 R172K, α-ketoglutarate, NADPH and $MnCl_2$ are included at final concentrations of 150 µM, 10 µM and 150 µM respectively. For IDH2 R140Q, α-ketoglutarate, NADPH and $MnCl_2$ are included at final concentrations of 3000 µM, 10 µM and 100 µM respectively. Final pH=7.0. Test compound dissolved in DMSO stock is diluted in the reaction mix at a final DMSO concentration of 4%. Compounds are tested in dose-response format. The assay is started by addition of enzyme. Enzymes are used at the following final concentrations: IDH1 R132H, 2 nM; IDH1 R132C, 0.5 nM; IDH2 R172K, 1.2 nM; IDH2 R140Q, 1.2 nM. After 90 minutes the reaction is quenched by adding ACN (50:50) containing 3-hydroxy-1,5-pentanedioic-2,2,3,4,4-$d_5$ acid ($5d_5$-3HG) as an internal standard for mass spectrometry analysis and quantitation of reaction product. 2-Hydroxyglutarate (2HG) in quenched samples is separated using strong anionic exchange column chromatography (Phenomenex Strata-X-A SecurityGuard) and analyzed by mass spectrometry in a 6460 triple quadrupole mass spectrometer (G6460A Agilent). The 2HG signal detected is transformed into an analyte concentration using a calibration curve generated using known 2HG concentrations. For each compound tested, the % inhibition is calculated using a DMSO control sample as 0% inhibition and a no enzyme control as 100% inhibition. $IC_{50}$ values are obtained from the individual % inhibition values at different compound concentrations using a 4-parameter equation. These calculations are carried out using Activity Base (IDBS) or Screener (Genedata) data analysis programs.

The results of this assay demonstrate that the exemplified and tested compounds inhibit mutant IDH1 activity against IHD1/R132H and IDH1/R132C.

The following Examples are tested essentially as described above and exhibit activity for mutant IDH1 as shown in Table 19 below and are selective for mutant IDH1 over mutant IDH2.

TABLE 19

| Example # | IDH1/R132H IC$_{50}$ (μM) | IDH1/R132C IC$_{50}$ (μM) | IDH2/R140Q IC$_{50}$ (μM) | IDH2/R172K IC$_{50}$ (μM) |
|---|---|---|---|---|
| 1 | 0.0291 ± 0.0107, n = 5 | 0.0266 ± 0.0103, n = 5 | 41.8 | 1.67 |
| 2 | 0.1100 ± 0.0460, n = 4 | 0.1020 ± 0.0430, n = 4 | 73.9 | 5.26 |
| 3 | 0.0509 ± 0.0131, n = 3 | 0.0295 ± 0.0082, n = 3 | 59.5 | 5.35 |
| 4 | 0.0786 ± 0.0189, n = 3 | 0.1330 ± 0.0320, n = 3 | 37.7 | 1.46 |
| 5 | 0.0560 ± 0.0157, n = 3 | 0.0523 ± 0.0225, n = 3 | >100 | 13.6 |
| 6 | 0.1500 ± 0.0240, n = 4 | 0.1620 ± 0.0420, n = 4 | >100 | 14.1 |
| 7 | 0.0397 ± 0.0260, n = 3 | 0.0448 ± 0.0219, n = 3 | 10.9 | 0.482 |
| 8 | 0.2900 ± 0.1700, n = 4 | 0.2090 ± 0.0750, n = 4 | >100 | 51.7 |
| 9 | 0.0417 ± 0.0036, n = 3 | 0.0629 ± 0.0188, n = 3 | 27 | 2.09 |
| 10 | 0.2600 ± 0.0350, n = 4 | 0.3090 ± 0.1070, n = 4 | >100 | 6.61 |
| 11 | 0.0802 ± 0.0519, n = 3 | 0.1190 ± 0.0541, n = 3 | >100 | 7.84 |
| 12 | 0.5150 ± 0.0860, n = 3 | 0.4570 ± 0.2290, n = 3 | >100 | 25.3 |
| 13 | 0.0777 ± 0.0196, n = 3 | 0.0924 ± 0.0154, n = 3 | 93.6 | 5.34 |
| 14 | 0.0819 ± 0.0541, n = 5 | 0.0825 ± 0.0583, n = 5 | >100 | 13 |
| 15 | 0.1280 ± 0.0090, n = 3 | 0.1090 ± 0.0540, n = 3 | >100 | 10.4 |
| 16 | 0.1160 ± 0.0150, n = 3 | 0.1370 ± 0.0440, n = 3 | 49 | 4.1 |
| 17 | 0.1140 ± 0.0380, n = 5 | 0.2150 ± 0.0860, n = 4 | 48.7 | 1.74 |
| 18 | 0.2110 | 0.1920 | | |
| 19 | 0.776 ± 0.210, n = 3 | 1.58 ± 0.34, n = 3 | >100 | 23.0 ± 12.4, n = 2 |
| 20 | 0.180 ± 0.033, n = 3 | 0.189 ± 0.033, n = 3 | 83.5 ± 17.4, n = 2 | 6.78 ± 2.40, n = 2 |
| 21 | 0.323 ± 0.076, n = 3 | 0.485 ± 0.017, n = 3 | >100 | 10.4 ± 7.0, n = 2 |
| 22 | 0.0825 ± 0.0107, n = 3 | 0.0771 ± 0.0102, n = 3 | 11.6 ± 2.0, n = 2 | 0.469 ± 0.355, n = 2 |
| 23 | 0.188 ± 0.048, n = 4 | 0.234 ± 0.067, n = 4 | | |

Mean ± standard deviation of the mean.

Biochemical Assays for Wild-Type IDH1 and IDH2 Enzymes

IDH1 and IDH2 enzymes catalyze the conversion of isocitrate to αKG. Wild-type IDH1 (National Center for Biotechnology Information, Accession: NP_001269316.1) and IDH2 (National Center for Biotechnology Information, Accession: EAX02082.1) proteins containing N-terminal His-tag are expressed in E. coli and purified using nickel affinity chromatography. The enzyme assays are carried out in V-bottom 96 well polypropylene plates containing 100 mM Tris-HCl buffer at pH 7.5, 1 mM DTT, 0.005% TRITON™ X-100, 120 mM NaCl. For the IDH1 wild-type assay isocitrate, NADP$^+$ and MnCl$_2$ are included at the concentrations of 85 μM, 50 μuM and 20 μM respectively. For the IDH2 wild-type assay isocitrate, NADP$^+$ and MnCl$_2$ are included at the concentrations of 30 μM, 50 μM and 10 μM respectively. Inhibitors dissolved in a DMSO stock solution are diluted in the reaction mixture at a final DMSO concentration of 4%. The enzyme assay is terminated (quenched) by adding ACN (50:50) containing d6-2-keto-pentanedioic acid (d6-αKG) as an internal standard for mass spectrometry analysis. Ten microliters of reaction mixture is combined with 100 μL of water, 50 μL of 1 M O-benzylhydroxylamine in pyridine buffer (8.6% pyridine, pH 5), and 50 μL of 1 M N-(3-dimethylaminopropyl)-N-ethylcarbodiimide hydrochloride (EDC) in pyridine buffer. Following derivatization at room temperature for one hour, samples are extracted with 600 μL of EtOAc. Four hundred L of the upper layer is removed, dried under heated nitrogen and reconstituted with 100 μL of MeOH/water (1:1). Ten μL of derivatized sample is injected onto an LC-MS system consisting of a Shimadzu Prominence 20A HPLC system and a The Thermo Quantum Ultra™ triple quadrupole mass spectrometer. Analytes are separated on a Waters XBridge™ C18 column (2.1×50 mm, 3.5 m) with a flow rate of 0.6 mL/minute. Mobile phase A is 0.1% formic acid in water and mobile phase B is MeOH. The αKG signal detected is transformed into analyte concentration using a calibration curve generated using known αKG concentrations. For each compound tested, the % inhibition is calculated using a DMSO control sample as 0% inhibition and a no enzyme control as 100% inhibition. IC$_{50}$ values are obtained from the individual % inhibition values at different compound concentrations using a 4-parameter equation. These calculations are carried out using Activity Base (IDBS) or Screener (Genedata) data analysis programs.

The results of this assay demonstrate that the exemplified and tested compounds are less active at inhibiting the IDH1 wild-type enzyme compared to the IDH1 R132H or R132C mutant enzymes.

The following Examples in Table 20 are tested essentially as described above and are less active at inhibiting the IDH1 wild-type enzyme compared to the IDH1 R132H or R132C mutant enzymes.

IDH1 Wild-Type and IDH2 Wild-Type Enzyme Activity

TABLE 20

| Example # | IDH1 Wild-Type IC$_{50}$ (µM) | IDH2 Wild-Type IC$_{50}$ (µM) |
| --- | --- | --- |
| 1 | 3.800 ± 1.360, n = 3 | 10.70 ± 1.65, n = 3 |
| 2 | 4.480 ± 4.310, n = 3 | 14.30 ± 3.11, n = 3 |
| 3 | 3.990 ± 1.900, n = 4 | 25.30 ± 21.30, n = 3 |
| 4 | 0.484 ± 1.180, n = 3 | 0.83 ± 1.49, n = 3 |
| 5 | 1.840 ± 1.960, n = 3 | 7.46 ± 7.52, n = 3 |
| 6 | 11.800 ± 5.660, n = 3 | 25.40 ± 6.32, n = 3 |
| 7 | 5.210 ± 4.640, n = 3 | 8.69 ± 10.20, n = 3 |
| 8 | 26.5 ± 15.9, n = 3 | 69.40 ± 24.90, n = 2 |
| 9 | 7.140 ± 13.100, n = 3 | 21.2 ± 32.2, n = 3 |
| 10 | 10.6 ± 11.2, n = 3 | 27.4 ± 18.7, n = 3 |
| 11 | 8.00 ± 3.38, n = 3 | 12.5 ± 21.2, n = 3 |
| 12 | 3.23 ± 6.87, n = 3 | 6.1 ± 13.3, n = 3 |
| 13 | 3.20 ± 2.54, n = 3 | 4.62 ± 6.65, n = 3 |
| 14 | 5.80 ± 6.83, n = 3 | 7.0 ± 13.3, n = 3 |
| 15 | 5.01 ± 2.25, n = 3 | 11.2 ± 6.4, n = 3 |
| 16 | 8.68 ± 6.03, n = 3 | 22.7 ± 11.8, n = 3 |
| 17 | 0.421 ± 0.764, n = 3 | 0.95 ± 1.29, n = 3 |
| 19 | 14.4 ± 0.2, n = 3 | 28.7 ± 1.5, n = 3 |
| 20 | 4.32 ± 0.37, n = 6 | 12.5 ± 0.4, n = 6 |
| 21 | 6.58 ± 1.01, n = 6 | 31.1 ± 2.1, n = 6 |
| 22 | 0.653 ± 0.042, n = 3 | 2.15 ± 0.13, n = 3 |

Mean ± standard deviation of the mean.

IDH1 (R132H) Biochemical Jump Dilution Assay

Lyophilized Example compounds are reconstituted to 10 mM or 100 mM with 100% DMSO and kept at room temperature until tested. IDH1(R132H)-His protein is expressed and purified by methods well known and commonly used by those skilled in the art. The assay reagents included the following: α-ketoglutaric acid (Sigma Cat# K1875), MnCl$_2$— Fisher Scientific Cat# M87-100, NADPH-Sigma-Aldrich Cat# N7505, Tris-HCl (Invitrogen, Cat#15567-027), NaCl (Sigma, S3014), dithiothreitol (Sigma, D5545), and TritonX100 (Peirce, 28314). The NAD(P)H-Glo™ Kit from Promega (G9061).

The assay buffer used throughout contains 100 mM Tris-HCl pH 7.0, 120 mM NaCl, 1 mM DTT, 0.005% Triton X-100, and 2% DMSO (from the addition of test compound). The IC$_{50}$ of each compound is determined by incubating a dose response of compound, prepared on an Echo555, with 1.5 nM IDH1(R132H), 1 mM α-ketoglutarate, 1 mM MnCl$_2$, and 15 µM NADPH in assay buffer. The reaction is incubated for 2 hours at room temperature, then stopped using 6-cyclopropyl-5-(isoquinolin-5-yl)-2-[(3R)-4-(3-methoxypropanoyl)-3-methylpiperazin-1-yl]pyridine-3-carbonitrile (10 µM). NADPH concentrations are measured using the NAD(P)H-Glo™ Kit, as specified by the vendor. The luminescent signal is read on the Envision (Perkin Elmer; 0.1 sec/Luminescense Mirror/Lum700 WL400-700 filter). In the subsequent jump dilution experiment, a compound concentration equivalent to 10× the IC$_{50}$ is pre-incubated with 100 nM IDH1(R132H). The concentration of compound is always greater than or equal to the enzyme concentration. After 2 hours at room temperature, this mixture is diluted 1:100 into a solution containing α-ketoglutarate (10 mM), MnCl$_2$ (10 mM), and NADPH (15 µM). This final enzyme reaction contains 1 nM IDH1(R132H) and 0.1× [IC$_{50}$]. After a 2 hour incubation at room temperature, the NADPH concentration is measured as specified above using 6-cyclopropyl-5-(isoquinolin-5-yl)-2-[(3R)-4-(3-methoxypropanoyl)-3-methylpiperazin-1-yl]pyridine-3-carbonitrile and the NAD(P)H-Glo™ Kit. Three controls are included: 1) "10× Control" containing 10×IC$_{50}$ compound in the preincubation and enzyme assay except 1 mM α-ketoglutarate, 1 mM MnCl$_2$, and 15 µM NADPH is used in the final assay measuring enzyme activity, 2) "Max Activity Control" containing DMSO in place of compound for both the preincubation and enzyme assay, and 3) "0.1× Control" containing DMSO in place of compound in the preincubation and 0.1×IC$_{50}$ compound in the enzyme assay. A "Min Activity Control" lacking enzyme, but otherwise equivalent to the "Max Activity Control" is included. A second set of Max and Min Activity Controls is performed using 1 mM α-ketoglutarate, 1 mM MnCl$_2$, and 15 µM NADPH. Each assay condition is tested in triplicate and 32 replicates are performed for the Max Activity Control (10 mM) and Min Activity Control (10 mM) while 16 replicates are performed for the Max Activity Control (1 mM) and Min Activity Control (1 mM).

The concentration of NADP (product) produced in each experiment/control is determined using the percent decrease in the observed signal relative to the Min Activity Control, containing 15 µM NADPH. The Min Activity Control (1 mM and 10 mM) and the Max Activity Control (1 mM and 10 mM) are averaged and the standard deviation calculated for each. The signal for each jump dilution and for the 0.1× Controls are multiplied by 15 then divided by the average counts for the Min Activity Control (10 mM) wells. This number is subtracted from 15 to calculate NADP (µM Product). The same calculations are used for the 10× Controls but the Min activity controls (1 mM) are used. The µmoles of the product for the Max Activity controls (1 mM and 10 mM) are calculated by multiplying the average counts by 15 then divide by the respective Min Activity Controls (1 mM and 10 mM). The µM NADP for each well is divided by the average Max Activity Control (1 mM or 10 mM) then multiplied by 100 to determine % IDH Activity for the compound jump dilution, 10× Control, and 0.1× Control. A passing compound must show <30% activity for the 10× control—showing that the preincubation concentration is sufficient to saturate the enzyme with compound. In addition, the compound must show >70-80% activity for the 0.1× control confirming that there is no inhibition at the 0.1×/diluted compound concentration.

Example compounds are tested essentially as described above and exhibit % recovery data for IDH1/R132H in this assay. Exemplified and tested compounds of the present invention inhibit the enzyme 2 hours after dilution contrary to art compound(s) that did not inhibit the enzyme 2 hours after dilution with the % recovery. Data from this assay demonstrates that the tested compounds of the present invention act in a manner consistent with covalent inhibition of mutant IDH1 since dilution of the inhibitor does not result in recovery of enzyme activity.

Cell-Based Assays for IDH1 Mutant Inhibitors

To test the cellular inhibition of IDH1 mutant R132C, the fibrosarcoma cell line HT1080 (purchased from ATCC) is used. For testing cell-based inhibition of the R132H mutation, the U87MG glioma cell line (ATCC) was stably transfected with a DNA construct expressing the R132H mutant enzyme.

HT1080 Cell Assay

Fifteen thousand cells are plated in poly-D-lys coated 96 well plates (15,000 cells/well) 18-24 hours prior to treatment with compounds. Four hours prior to compound treatment, cells are glutamine-starved by removing normal media and replacing with glutamine-free media. Following starvation, cells are then treated with different concentrations of test compounds (20 µM to 1 nM) dissolved in glutamine free media containing DMSO at a final concentration of 0.2%. The initial compound incubation is for 1 hour at 37° C./5% $CO_2$. After 1 hour, glutamine is added to a final 2 mM concentration and the treated cells are then incubated for a further 18 hours at 37° C./5% $CO_2$. Following the 18 hour incubation, intracellular 2HG and αKG are analyzed in cell lysates. Lysates are prepared following removal of media and addition of buffer containing 25 mM Tris-HCl pH 7.5, 150 mM NaCl, 1 mM EDTA, 1 mM EGTA/1% Triton-X 100 to the cells. An aliquot of lysate is added to a mix of $d_6$-αKG and $d_5$-3HG as internal standards and the mixture is treated with O-benzylhydroxylamine in the presence of N-(3-dimethylaminopropyl)-N'-ethylcarbodiimide hydrochloride (EDC) and pyridine. Analyte derivatives are then extracted with EtOAc, dried, and then reconstituted with 50% MeOH in $H_2O$. Samples prepared as described are injected into the HPLC to separate 2HG and αKG derivatives (and corresponding internal standards) using a reverse phase chromatography in a C18 column. Analysis of the samples is carried out using a 6460 triple quadrupole mass spectrometer (G6460A Agilent). The 2HG and αKG signals detected are transformed into analyte concentration using the ratio of αKG/$d_6$-αKG and the ratio of 2HG/$d_5$-3HG that is extrapolated within a calibration curve. Percent inhibition for each individual sample is obtained after normalizing calculated 2HG or aKG concentration to maximum and minimum references obtained in the presence and in the absence of glutamine during cell treatment with compounds. $IC_{50}$ values are obtained from individual % inhibition using a sigmoidal dose-response 4-parameter equation. These calculations are carried out automatically using Activity Base (IDBS) or Screener (Genedata) data analysis programs.

The results of this assay demonstrate that the tested Examples in Table 21 inhibit production of 2-hydroxyglutarate, indicating the inhibition of mutant IDH1 R132C in cells in this assay. αKG, a metabolite generated by wild-type IDH1 is not affected by the inhibitors, indicating the compounds are selective for mutant IDH1 over wild type IDH1 in cells in this assay. The resulting $IC_{50}$ values for the following Examples are shown in Table 21.

TABLE 21

| Example # | HT1080 (R132C, 2-hydroxyglutarate) $IC_{50}$ (µM) | HT1080 (R132C, αKG) $IC_{50}$ (µM) |
|---|---|---|
| 1 | 0.00939 ± 0.00287, n = 6 | >20.0 |
| 2 | 0.0281 ± 0.0091, n = 6 | >20.0 |
| 3 | 0.0231 ± 0.0024, n = 3 | >20.0 |
| 4 | 0.0283 ± 0.0147, n = 5 | >20.0 |
| 5 | 0.0447 ± 0.0193, n = 3 | >20.0 |
| 6 | 0.153 ± 0.082, n = 4 | >20.0 |
| 7 | 0.0387 ± 0.0013, n = 2 | >20.0 |
| 8 | 0.0770 ± 0.0425, n = 4 | >20.0 |
| 9 | 0.0323 ± 0.0117, n = 3 | >20.0 |
| 10 | 0.0978 ± 0.0431, n = 3 | >20.0 |
| 11 | 0.0321 ± 0.0108, n = 3 | >20.0 |
| 12 | 0.120 ± 0.020, n = 4 | >20.0 |
| 13 | 0.128 ± 0.009, n = 2 | >20.0 |
| 14 | 0.0898 ± 0.0552, n = 4 | >20.0 |
| 15 | 0.0278 ± 0.00623, n = 3 | >20.0 |
| 16 | 0.0349 ± 0.0171, n = 4 | >20.0 |
| 17 | 0.0990 ± 0.0351, n = 4 | >20.0 |
| 18 | 0.380 ± 0.130, n = 2 | >20.0 |
| 19 | 0.208, ± 0.091, n = 3 | >20.0 |
| 20 | 0.0955 ± 0.0249, n = 3 | >20.0 |
| 21 | 0.408 | >20.0 |
| 22 | 0.04310 ± 0.04400, n = 2 | >20.0 |
| 23 | 0.0321 ± 0.0136, n = 4 | >20 |

Mean ± standard deviation of the mean.

U87MG/IDH1R132H Cell Assay

Cells are plated in poly-D-lys coated 96 well plates (12,000 cells/well) 18-24 hours previous to treatment with compounds. Four hours prior to compound treatment, cells are glutamine-starved by removing normal media and replacing with glutamine-free media. Following starvation, cells are then treated with different concentrations of test compounds (20 µM to 1 nM) dissolved in glutamine free media containing DMSO at a final concentration of 0.2%. The initial compound incubation is for 1 hour at 37° C./5% $CO_2$. After 1 hour, glutamine is added to a final 2 mM concentration and the treated cells are then incubated for a further 18 hours at 37° C./5% $CO_2$. Intracellular 2HG is analyzed in cell lysates obtained after media removal and treatment with lysis buffer (25 mM Tris-HCl pH 7.5, 150 mM NaCl, 1 mM EDTA, 1 mM EGTA/1% Triton-X 100). Cell lysates are conserved at −80° C. until processing. For analyte extraction, an aliquot of thawed lysate is transferred to a deep 96-well plate and treated with cold MeOH containing $d_5$-3HG as an internal standard followed by chloroform and $H_2O$ (1:4:3:2). The upper phase is collected after separation and injected in HPLC to separate 2HG (and internal standard) using hydrophilic interaction (HILIC) chromatography coupled to MS/MS detection in a 6460 triple quadrupole mass spectrometer. Percent inhibition for each individual sample is obtained after normalizing calculated 2HG concentration to maximum and minimum references obtained in the presence and in the absence of glutamine during cell treatment with compounds. $IC_{50}$ values are obtained from individual % inhibition using a sigmoidal dose-response 4-parameter equation. These calculations are carried out automatically using Activity Base (IDBS) or Screener (Genedata) data analysis programs.

The following Examples are tested essentially as described above and exhibit inhibition activity against mutant IDH1/R132H in U87MG cells in this assay as shown in Table 22 below.

TABLE 22

| Example # | U87MG (IDH1/R132H 2-hydroxyglutarate $IC_{50}$ (µM) |
|---|---|
| 1 | 0.00265 ± 0.00007, n = 2 |
| 2 | 0.00508 ± 0.00165, n = 3 |
| 3 | 0.0059 |
| 4 | 0.00298 ± 0.00258, n = 3 |
| 5 | 0.00984 ± 0.00810, n = 3 |
| 6 | 0.0174 ± 0.0013, n = 3 |
| 7 | 0.00564 ± 0.00035, n = 2 |
| 8 | 0.0189 ± 0.0051, n = 4 |
| 9 | 0.00368 ± 0.00057, n = 2 |
| 10 | 0.00714 ± 0.00127, n = 2 |
| 11 | 0.00735 ± 0.00007, n = 2 |
| 12 | 0.0135 ± 0.0011, n = 2 |
| 13 | 0.00750 ± 0.000283, n = 2 |
| 14 | 0.00975 ± 0.00241, n = 4 |
| 15 | 0.00390 ± 0.00000, n = 2 |
| 16 | 0.00579 ± 0.00057, n = 2 |
| 17 | 0.00675 ± 0.00113, n = 2 |
| 18 | 0.0707 |
| 19 | 0.0449 ± 0.0224, n = 4 |
| 20 | 0.0319 ± 0.0117, n = 2 |
| 21 | 0.0246 ± 0.0159, n = 2 |
| 22 | 0.0152 ± 0.0049, n = 4 |
| 23 | 0.00903 ± 0.00075, n = 4 |

Mean ± standard deviation of the mean.

In Vivo 2-Hydroxyglutarate Assay

For in vivo testing of IDH1 inhibitors, sub-cutaneous xenograft tumors are grown in athymic nude mice (20-22 g, Harlan Laboratories) following implantation of either HT1080 cells (fibrosarcoma carrying R132C mutant IDH1) or TB08 cells (secondary glioblastoma carrying R132H mutant IDH1). Mice are fed and watered ad libitum and are acclimatized for 1 week prior to implantation of cells. Tumor cells (HT1080) or tumor fragments (TB08) are implanted into the right rear flank. For HT1080, $5.0 \times 10^6$ cells are implanted in a 1:1 mixture with Matrigel in a final volume of 0.2 ml. For TB08, tumor fragments generated from ex-planted tumor samples are implanted directly into the hind flank. Tumor volumes are measured by caliper twice weekly and tumor volume is calculated using $0.536 \times L \times W^2$, where L=length and W=width. When tumor volumes reach 150-400 mm$^3$, animals are randomized, placed into groups (n=3-6 per group) and dosed with IDH1 inhibitors or vehicle control. For IDH1 inhibitors, compounds are formulated in vehicle containing either 1% hydroxyethylcellulose/0.25% Tween 80/0.05% Antifoam or 10% Acacia with 1.1 mol equivalent of HCl. Compounds are bath sonicated to obtain suspension. Compounds are dosed on a milligram per kilogram (mpk) basis via oral gavage in a final volume of 0.2 ml. To determine inhibition of 2HG, compounds are dosed twice daily (BID) for 3 days (total number of doses=6). Following compound treatment, mice are euthanized with isofluorane anesthesia and cervical dislocation. Tumors are excised, put into labeled tubes, and immediately frozen in liquid nitrogen. Tumors are stored at −80° C. for processing.

Preparation of Tumor Lysates

XY Lite buffer is prepared in molecular grade water and contains the following components: 25 mM Tris, pH 7.5, 150 mM NaCl, 1% Triton X-100, 1 mM EDTA, 1 mM EGTA. To XY Lite (40 ml), 800 µl of Halt Protease and Phosphatase Inhibitors cocktail (Halt™ Protease and Phosphatase Inhibitor Cocktail, EDTA-Free Thermo Scientific, Cat#78441) is added. Samples are vortexed and then chilled on ice. Orange cap lysing-A tubes are labeled and placed in a rack on ice. A ceramic mortar and pestle is placed in dry ice to cool. A 2×2 inch square of aluminum foil is placed in the bottom of the mortar. A tumor sample is transferred to the pre-chilled mortar on the foil square. Liquid nitrogen (about 5 ml) is added and allowed to evaporate, super-freezing the tumor. Another piece of foil is placed over the tumor and the tumor smashed to small pieces with the ceramic pestle. The crushed tumor is quickly transferred to the lysing tube. Ice-cold XY Lite (500 µL) is added to each tube and capped. Tumors are then processed on the FastPrep-24 MP Biomedicals by spinning twice for 35 seconds each at speed setting 5. Samples are then centrifuged in Beckman Microfuge R at 4° C. at 14,000 rpm for 30 minutes. Supernatant is transferred to a pre-chilled 96 deep well plate. The pellet is discarded.

Protein Assay

A protein assay dilution plate is first generated by adding XY buffer (145 µl) to a non-sterile 96 well round bottom Corning plate. To this, tumor lysate (5 µL) is added and gently mixed. The plate is kept on ice. Serial dilutions of BSA standard (Thermo Scientific cat. 23209 2 mg/mL) are set-up as follows: Five 0.5 mL tubes are placed in a rack and XY buffer (60 µL) is added to each. Stock BSA (60 µl) is added to first tube and vortexed. 60 µl from the first tube is transferred to the next tube, vortexed, and so forth, until the dilution series is complete as follows: Tube 1=stock BSA, Tubes 2-5 are 1:2 serial dilutions, Tube 6=XY buffer alone. Thermo BCA Protein Assay reagents are mixed according to manufacturer instructions. Mixed BCA Reagent (200 µl) is added to each sample and incubated for 15 minutes. The protein assay results are read on SOFTmax Pro Plate Reader. Based on protein assay results, the appropriate amount of XY buffer is added to each tumor lysate to generate a final protein concentration of 5 mg/mL. All samples are labeled and stored at −80° C.

Metabolite Analysis in Tumor Lysates

The in vivo effects of DH1 inhibition on the concentrations of total 2HG and αKG is determined by liquid chromatography-mass spectrometry (LC-MS) analysis of tumor xenografts. The method utilizes derivatization with O-benzylhydroxylamine prior to analysis by LC-MS. Ten microliters of each tumor lysate is placed into a deep-well 96-well plate and combined with 100 µL of internal standard solution containing 10 µM $d_5$-3HG and 10 µM d6-αKG. 50 µL of 1 M O-benzylhydroxylamine in pyridine buffer (8.6% pyridine, pH 5) and 50 µL of 1 M N-(3-dimethylaminopropyl)-N-ethylcarbodiimide hydrochloride (EDC) in pyridine buffer is added to each sample. The derivatization reaction proceeds at room temperature for one hour. Using a Beckman Biomek FX liquid handler 600 μL of EtOAc is added to each sample. Plates are sealed and vortexed for 5 minutes, then they are centrifuged for 5 minutes at 4000 rpm in Eppendorf 5810R centrifuge. 400 μL of the upper layer is transferred to a new 96-well plate. Samples are dried under heated nitrogen at 50° C. and reconstituted with 100 μL of MeOH/water (1:1). One microliter of derivatized sample is injected onto an LC-MS system consisting of a Shimadzu Prominence 20A HPLC system and a Thermo Quantum Ultra™ triple quadrupole mass spectrometer. Analytes are separated on a Water XBridge™ C18 column (2.1×50 mm, 3.5 μm) with a flow rate of 0.6 ml/minute. Mobile phase A is 0.1% formic acid in water and mobile phase B is MeOH. The gradient profile is: 0 minutes, 5% B; 3 minutes, 100% B; 4.00 minutes, 100% B; 4.1 minutes, 5% B; 5.50 minutes, stop. The mass spectrometer utilizes a HESI-II probe operated in positive ion selected reaction monitoring mode. Calibration curves are constructed by plotting analyte concentrations vs. analyte/internal standard peak area ratios and performing a quadratic fit of the data using a 1/concentration weighting with Xcalibur™ software. Analyte concentrations for the unknowns are back-calculated from the calibration curves. Metabolite data from the LCMS assay is expressed in nmol/mg protein. The average 2HG level in the vehicle treated group is used to determine the 0% inhibition control. The % inhibition in each inhibitor treated animal is then determined relative to the vehicle control. Data are analyzed in JMP software to determine the average % inhibition in each dose group, the standard deviation, and the standard error.

Data demonstrating in vivo inhibition of 2-hydroxyglutarate in IDH1 mutant xenograft mice by exemplified and tested compounds is shown in Table 23 below.

TABLE 23

| Xenograft Model | Treatment or Ex No. | Dose | Mice (n) | 2HG, Mean % Inhibition | Std Dev | Std Err Mean |
|---|---|---|---|---|---|---|
| TB08 (R132H) | Vehicle | 0.00 mpk | 5 | 0.00 | 32.96 | 14.74 |
| TB08 (R132H) | 1 | 1.88 mpk | 4 | 29.61 | 5.09 | 2.55 |
| TB08 (R132H) | 1 | 3.75 mpk | 4 | 56.48 | 14.28 | 7.14 |
| TB08 (R132H) | 1 | 7.50 mpk | 4 | 77.38 | 2.22 | 1.11 |
| TB08 (R132H) | 1 | 15.0 mpk | 4 | 87.60 | 1.78 | 0.89 |
| TB08 (R132H) | 1 | 30.0 mpk | 3 | 93.03 | 1.00 | 0.58 |
| TB08 (R132H) | 1 | 60.0 mpk | 3 | 93.56 | 0.99 | 0.57 |
| | | | Number Mice | | | |
| TB08 (R132H) | Vehicle | 0.00 mpk | 6 | 0.00 | 32.29 | 13.18 |
| TB08 (R132H) | 2 | 1.88 mpk | 6 | −13.99 | 29.70 | 12.13 |
| TB08 (R132H) | 2 | 3.75 mpk | 6 | 30.26 | 29.64 | 12.10 |
| TB08 (R132H) | 2 | 7.50 mpk | 6 | 67.44 | 15.50 | 6.33 |
| TB08 (R132H) | 2 | 15.0 mpk | 6 | 85.71 | 3.55 | 1.45 |

TABLE 23-continued

| Xenograft Model | Treatment or Ex No. | Dose | | 2HG, Mean % Inhibition | Std Dev | Std Err Mean |
|---|---|---|---|---|---|---|
| TB08 (R132H) | 2 | 30.0 mpk | 6 | 87.80 | 6.19 | 2.53 |
| TB08 (R132H) | 2 | 60.0 mpk | 6 | 88.13 | 3.07 | 1.25 |
| HT1080 (R132C) | Vehicle | 0.00 mpk | 6 | 0.00 | 9.62 | 3.93 |
| HT1080 (R132C) | 1 | 1.88 mpk | 6 | −11.62 | 15.43 | 6.30 |
| HT1080 (R132C) | 1 | 3.75 mpk | 6 | 28.89 | 12.39 | 5.06 |
| HT1080 (R132C) | 1 | 7.50 mpk | 6 | 50.91 | 7.77 | 3.17 |
| HT1080 (R132C) | 1 | 15.0 mpk | 6 | 69.59 | 11.76 | 4.80 |
| HT1080 (R132C) | 1 | 30.0 mpk | 6 | 87.43 | 1.82 | 0.74 |
| HT1080 (R132C) | 1 | 60.0 mpk | 6 | 95.19 | 1.79 | 0.73 |
| HT1080 (R132C) | Vehicle | 0.00 mpk | 6 | 0.00 | 18.96 | 7.74 |
| HT1080 (R132C) | 2 | 1.88 mpk | 6 | 22.48 | 9.07 | 3.70 |
| HT1080 (R132C) | 2 | 3.75 mpk | 6 | 27.94 | 9.58 | 3.91 |
| HT1080 (R132C) | 2 | 7.50 mpk | 6 | 38.71 | 7.63 | 3.11 |
| HT1080 (R132C) | 2 | 15.0 mpk | 6 | 71.19 | 4.90 | 2.00 |
| HT1080 (R132C) | 2 | 30.0 mpk | 6 | 86.71 | 4.76 | 1.94 |
| HT1080 (R132C) | 2 | 60.0 mpk | 6 | 96.03 | 0.70 | 0.29 |

We claim:

1. A compound of the formula:

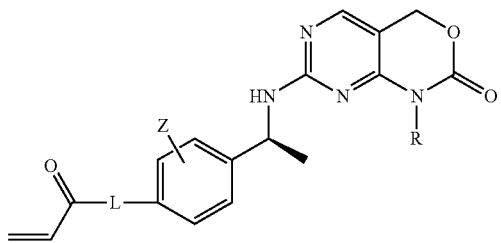

I wherein
L is a linker selected from the group consisting of —N-azetidine-3-$CH_2$—O—, —N-azetidine-3-O—($CH_2$)—, —N-2,6-diazaspiro[3.3]heptane-6-($CH_2$)—, —N-piperazine-4-($CH_2$)—, —N-piperazine-, —N-azetidine-3-($CH_2CH_2$)—, -7-N-(2,7-diazaspiro[3.5]nonane)-2-($CH_2$), —N-azetidine-3-(NMe)$CH_2$—, —N-piperidine-4-(NMe)$CH_2$—, N-2,5-dihydropyrrol-3-($CH_2$)—O—;
Z is selected from the group consisting of H or F;
R is selected from the group consisting of $C_1$-$C_4$ alkyl, —CH($CH_3$)$CH_2$—OH, —$CH_2CH_2$F, —$CH_2CHF_2$;
or a pharmaceutically acceptable salt thereof.

2. A compound of claim 1 wherein: L is a linker selected from the group consisting of —N-piperazine-4-($CH_2$)—, —N-piperazine-, —N-azetidine-3-(NMe)$CH_2$—, —N-azetidine-3-$CH_2$—O—, —N-azetidine-3-O—($CH_2$)—, —N-azetidine-3-($CH_2CH_2$)—, and —N-piperidine-4-(NMe)$CH_2$—;
Z is H;

R is C$_1$-C$_4$ alkyl;
or a pharmaceutically acceptable salt thereof.

3. A compound of claim 2 wherein:

L is a linker selected from the group consisting of —N-piperazine-4-(CH$_2$)—, —N-piperazine-, —N-azetidine-3-(NMe)CH$_2$—, —N-azetidine-3-O—(CH$_2$)—, —N-azetidine-3-(CH$_2$CH$_2$)—, and —N-piperidine-4-(NMe)CH$_2$—;

Z is H;

R is selected from CH$_2$CH$_3$, CH(CH$_3$)$_2$;

or a pharmaceutically acceptable salt thereof.

4. A compound of claim 3 which is 1-isopropyl-7-[[(1S)-1-[4-[(4-prop-2-enoylpiperazin-1-yl)methyl]phenyl]ethyl]amino]-4H-pyrimido[4,5-d][1,3]oxazin-2-one, or a pharmaceutically acceptable salt thereof.

5. A compound of claim 3 which is 1-ethyl-7-[[(1S)-1-[4-[(4-prop-2-enoylpiperazin-1-yl)methyl]phenyl]ethyl]amino]-4H-pyrimido[4,5-d][1,3]oxazin-2-one, or a pharmaceutically acceptable salt thereof.

6. A compound of claim 3 which is:

1-isopropyl-7-[[(1S)-1-[4-(4-prop-2-enoylpiperazin-1-yl)phenyl]ethyl]amino]-4H-pyrimido[4,5-d][1,3]oxazin-2-one, or a pharmaceutically acceptable salt thereof;

1-ethyl-7-[[(1S)-1-[4-(4-prop-2-enoylpiperazin-1-yl)phenyl]ethyl]amino]-4H-pyrimido[4,5-d][1,3]oxazin-2-one, or a pharmaceutically acceptable salt thereof;

1-ethyl-7-[[(1S)-1-[4-[(1-prop-2-enoylazetidin-3-yl)oxymethyl]phenyl]ethyl]amino]-4H-pyrimido[4,5-d][1,3]oxazin-2-one, or a pharmaceutically acceptable salt thereof;

1-ethyl-7-[[(1S)-1-[4-[2-(1-prop-2-enoylazetidin-3-yl)ethyl]phenyl]ethyl]amino]-4H-pyrimido[4,5-d][1,3]oxazin-2-one, or a pharmaceutically acceptable salt thereof;

or 1-ethyl-7-[[(1S)-1-[4-[[methyl-(1-prop-2-enoylazetidin-3-yl)amino]methyl]-phenyl]ethyl]amino]-4H-pyrimido[4,5-d][1,3]oxazin-2-one, or a pharmaceutically acceptable salt thereof.

7. A pharmaceutical composition comprising a compound of claim 1 or a pharmaceutically acceptable salt thereof, and a pharmaceutically acceptable carrier.

8. A method of treating a cancer expressing mutant IDH1 which is glioma, glioblastoma, glioblastoma multiforme, astrocytoma, oligodendroglioma, paraganglioma, fibrosarcoma, angioimmunoblastic T-cell lymphoma, myelodysplastic syndrome, B cell acute lymphoblastic leukemia, thyroid cancer, colorectal cancer, acute myeloid leukemia, melanoma, prostate cancer, chondrosarcoma or cholangiocarcinoma in a patient comprising administering to a patient in need thereof a therapeutically effective amount of a compound of claim 1, or a pharmaceutically acceptable salt thereof.

9. The method of claim 8 wherein the cancer expressing mutant IDH1 is glioma, glioblastoma, acute myeloid leukemia, or fibrosarcoma.

10. A compound of claim 2, which is 1-isopropyl-7-[[(1S)-1-[4-[(1-prop-2-enoylazetidin-3-yl)methoxy]phenyl]ethyl]amino]-4H-pyrimido[4,5-d][1,3]oxazin-2-one, or a pharmaceutically acceptable salt thereof.

* * * * *

UNITED STATES PATENT AND TRADEMARK OFFICE
CERTIFICATE OF CORRECTION

PATENT NO.        : 10,253,041 B2
APPLICATION NO.   : 15/570759
DATED             : April 9, 2019
INVENTOR(S)       : Renato A. Bauer et al.

It is certified that error appears in the above-identified patent and that said Letters Patent is hereby corrected as shown below:

In the Claims

Column 78, Line 61, in Claim 2, please delete "claim_1" and insert --claim 1--, therefor.

Signed and Sealed this
Twenty-seventh Day of August, 2019

Andrei Iancu
*Director of the United States Patent and Trademark Office*